US011439622B2

(12) United States Patent
Brem et al.

(10) Patent No.: US 11,439,622 B2
(45) Date of Patent: Sep. 13, 2022

(54) INHIBITORS OF METALLO-BETA-LACTAMASES

(71) Applicant: OXFORD UNIVERSITY INNOVATION LIMITED, Oxford (GB)

(72) Inventors: Jürgen Brem, Oxford (GB); Anna M. Rydzik, Oxford (GB); Michael A. McDonough, Oxford (GB); Christopher J. Schofield, Oxford (GB); Angus Morrison, Newhouse (GB); Joanne Hewitt, Newhouse (GB); Andrew Pannifer, Newhouse (GB); Philip Jones, Newhouse (GB)

(73) Assignee: Oxford University Innovation Limited, Oxford (GB)

( * ) Notice: Subject to any disclaimer, the term of this patent is extended or adjusted under 35 U.S.C. 154(b) by 85 days.

(21) Appl. No.: 15/779,775

(22) PCT Filed: Nov. 30, 2016

(86) PCT No.: PCT/GB2016/053761
§ 371 (c)(1),
(2) Date: May 29, 2018

(87) PCT Pub. No.: WO2017/093727
PCT Pub. Date: Jun. 8, 2017

(65) Prior Publication Data
US 2020/0375946 A1 Dec. 3, 2020

(30) Foreign Application Priority Data
Nov. 30, 2015 (GB) .................. 1521059.4

(51) Int. Cl.
| | | |
|---|---|---|
| A61K 31/404 | (2006.01) |
| C07D 209/42 | (2006.01) |
| C07D 401/04 | (2006.01) |
| A61K 31/4439 | (2006.01) |
| A61K 45/06 | (2006.01) |
| C07D 413/10 | (2006.01) |
| A61K 31/5377 | (2006.01) |
| C07D 403/10 | (2006.01) |
| A61K 31/4155 | (2006.01) |
| A61K 31/4375 | (2006.01) |
| C07D 471/04 | (2006.01) |
| C07D 403/04 | (2006.01) |
| A61K 31/506 | (2006.01) |
| A61K 31/4196 | (2006.01) |
| A61K 31/4025 | (2006.01) |
| C07D 409/04 | (2006.01) |
| C07D 413/14 | (2006.01) |
| C07D 417/12 | (2006.01) |
| A61K 31/427 | (2006.01) |
| A61P 31/04 | (2006.01) |

(52) U.S. Cl.
CPC ........ *A61K 31/404* (2013.01); *A61K 31/4025* (2013.01); *A61K 31/4155* (2013.01); *A61K 31/4196* (2013.01); *A61K 31/427* (2013.01); *A61K 31/4375* (2013.01); *A61K 31/4439* (2013.01); *A61K 31/506* (2013.01); *A61K 31/5377* (2013.01); *A61K 45/06* (2013.01); *A61P 31/04* (2018.01); *C07D 209/42* (2013.01); *C07D 401/04* (2013.01); *C07D 403/04* (2013.01); *C07D 403/10* (2013.01); *C07D 409/04* (2013.01); *C07D 413/10* (2013.01); *C07D 413/14* (2013.01); *C07D 417/12* (2013.01); *C07D 471/04* (2013.01)

(58) Field of Classification Search
CPC .............. A61K 31/404; A61K 31/4025; A61K 31/4155; A61K 31/4196; A61K 31/427; A61K 31/4375; A61K 31/4439; A61K 31/506; A61K 31/5377; A61K 45/06; A61P 31/04; C07D 209/42; C07D 401/04; C07D 403/04; C07D 403/10; C07D 409/04; C07D 413/10; C07D 413/14; C07D 417/12; C07D 471/04
USPC ..................................................... 514/235.2
See application file for complete search history.

(56) References Cited

U.S. PATENT DOCUMENTS

| | | | |
|---|---|---|---|
| 2002/0091148 A1 | 7/2002 | BaMaung et al. | |
| 2007/0015813 A1* | 1/2007 | Carter ..................... A61P 25/28 | 514/414 |

FOREIGN PATENT DOCUMENTS

| | | |
|---|---|---|
| CN | 104138594 A | 11/2014 |
| EP | 0613894 A1 | 9/1994 |
| JP | H04211651 A | 8/1992 |
| JP | H06145150 A | 5/1994 |
| WO | WO-97/006141 A1 | 2/1997 |

(Continued)

OTHER PUBLICATIONS

Friberg et al., Discovery of Potent Myeloid Cell Leukemia 1 (Mcl-1) Structure-Based Design, 2013, Journal of Medicinal Chemistry, 56(1), 15-30 (Year: 2013).*

(Continued)

*Primary Examiner* — Kristin A Vajda
(74) *Attorney, Agent, or Firm* — Foley Hoag LLP; David P. Halstead; Lawrence P. Tardibono

(57) ABSTRACT

The present invention relates to certain compounds, in particular, indole derivatives that function as inhibitors of bacterial metallo-beta-lactamases. The present invention also relates to processes for the preparation of these compounds, to pharmaceutical compositions comprising them, and to their use in the treatment of a bacterial infection.

9 Claims, No Drawings

(56) References Cited

FOREIGN PATENT DOCUMENTS

| WO | WO-2005105213 A2 | 11/2005 |
|---|---|---|
| WO | WO-2006112549 A1 | 10/2006 |
| WO | WO-2007048847 A2 | 5/2007 |
| WO | WO-2008/068184 A1 | 6/2008 |
| WO | WO-2008/131000 A2 | 10/2008 |
| WO | WO-2009/023179 A2 | 2/2009 |
| WO | WO-2009158375 A1 | 12/2009 |
| WO | WO-2011/006158 A2 | 1/2011 |
| WO | WO-2015/112441 A1 | 7/2015 |

OTHER PUBLICATIONS

Walser et al., Synthesis and transformations of some 3-chloro-and 3-nitroindolenines, 1973, Journal of Organic Chemistry, 38(18), 3077-84 (Year: 1973).*

Hughes et al., Indoles. IV. The utilization of the Japp-Klingemann reaction for the preparation of substituted indolecarboxylic acids, 1938, Journal and Proceedings of the Royal Society of New South Wales, 71, 475-85 (Year: 1938).*

Basanagoudar et al., "Synthesis of 10-phenyl-1,2,3,4-tetrahydropyrazino[1,2-a]indoles and ethyl 1-(2-aminoethyl)-3-phenylindole-2-carboxylates," Indian J. Chem B. 30b(11):1014-1017 (1991).

Frank et al., "Discovery of a Potent Inhibitor of Replication Protein A Protein-Protein Interactions Using a Fragment-Linking Approach," J. Med. Chem. 56(22):9242-9250 (2013).

International Search Report and Written Opinion for International Application No. PCT/GB2016/053761 dated Feb. 21, 2017.

Leete et al., "The Biogenesis of Alkaloids: XIV. A Study of the Biosynthesis of Damascenine and Trigonelline," Can. J. Chem. 33(2):405-410 (1955).

Andersen et al., "Selective, centrally acting serotonin 5-HT2 antagonists. 2. Substituted 3-(4-fluorophenyl)-1H-indoles," J. Med. Chem., 35: 4823-4831 (1992).

Hiremath et al., "Synthesis of biheterocycles containing indole nucleus," Proceedings of the National Academy of Sciences, India, Section A: Physical Science, 62: 161-166 (1992).

Hussein et al., "Synthesis and Kinetic Testing of Tetrahydropyrimidine-2-thione and Pyrrole Derivatives as Inhibitors of the Metallo-blactamase from Klebsiella pneumonia and Pseudomonas aeruginosa," Chem. Biol. Drug. Des., 80: 500-515 (2012).

Maddirala et al., "Fischer indolisation of 2,6-dialkyl and 2,4,6-trialkylphenylhydrazones of diketones and ketoesters," Tetrahedron Letters, 44: 5665-5668 (2003).

Mohamed et al., "Synthesis and kinetic testing of new inhibitors for a metallo-β-lactamase from Klebsiella pneumonia and Pseudomonas aeruginosa," European Journal of Medicinal Chemistry, 46: 6075-6082 (2011).

Borsche et al., "Über vielkernige kondensierte Systeme mit heterocyclischen Ringen. XI. Ringschlußversuche mit 2,3-Phenyl-pyrrol-carbonsäuren und mit 2,3-Phenyl-indol-carbonsäuren," EuroJoc, 548(1): 64-74 (1941).

CAS Registry No. 1027903-08-7 dated Oct. 8, 2018.
CAS Registry No. 1158264-18-6 dated Oct. 8, 2018.
CAS Registry No. 1158638-99-3 dated Oct. 8, 2018.
CAS Registry No. 1551869-36-3 dated Feb. 14, 2014.
CAS Registry No. 1554297-45-8 dated Feb. 24, 2014.
CAS Registry No. 1781341-91-0 dated Jun. 17, 2015.
Manske et al., "I.-Harmine and harmaline. Part IX. A synthesis of harmaline," Journal of The Chemical Society: 1-14 (1927).

Bie et al., "Design, synthesis and biological evaluation of 7-nitro-1H-indole-2-carboxylic acid derivatives as allosteric inhibitors of fructose-1,6-bisphosphatase," Bioorganic & Medicinal Chemistry, 22(6): 1850-1862 (2014).

Biradar et al., "Microwave Assisted Synthesis of Novel Imidazolopyridinyl Indoles as Potent Antioxidant and Antimicrobial Agents," Journal of Chemistry, 2014: Article ID 579612, 8 pages (2014).

International Search Report in United Kingdom Application No. GB1521059.4, dated Sep. 27, 2016, pp. 1-8.

Jansen et al., "Variations of acidic functions at position 2 and substituents at positions 4, 5 and 6 of the indole moiety and their effect on NMDA-glycine site affinity," European Journal of Medicinal Chemistry, 38(10): 855-865 (2003).

Buynak et al., "β-Lactamase inhibitors: a review of the patent literature (2010-2013)," Expert Opinion on Therapeutic Patents, 23(11): 1469-1481 (2013).

CAS Registry No. 1158191-72-0 dated Jun. 16, 2009.
CAS Registry No. 1158594-83-2 dated Jun. 16, 2009.
CAS Registry No. 1215909-65-1 dated Apr. 4, 2010.
CAS Registry No. 1216169-15-1 dated Apr. 4, 2010.
CAS Registry No. 1216225-20-5 dated Apr. 4, 2010.
CAS Registry No. 1216319-18-4 dated Apr. 4, 2010.
CAS Registry No. 1225058-93-4 dated May 25, 2010.
CAS Registry No. 1347412-60-5 dated Dec. 2, 2011.
CAS Registry No. 1546171-29-2 dated Feb. 17, 2014.
CAS Registry No. 1552269-48-3 dated Feb. 21, 2014.
CAS Registry No. 1553656-57-7 dated Feb. 24, 2014.
CAS Registry No. 1553914-92-3 dated Feb. 24, 2014.
CAS Registry No. 1554595-86-6 dated Feb. 24, 2014.
CAS Registry No. 1555991-47-3 dated Feb. 25, 2014.
CAS Registry No. 1556296-17-3 dated Feb. 26, 2014.
CAS Registry No. 1557846-51-1 dated Feb. 27, 2014.
CAS Registry No. 1558373-59-3 dated Feb. 28, 2014.
CAS Registry No. 1779899-57-8 dated Jun. 14, 2015.
CAS Registry No. 1780366-75-7 dated Jun. 14, 2015.
CAS Registry No. 1780721-15-4 dated Jun. 15, 2015.
CAS Registry No. 1780878-23-0 dated Jun. 15, 2015.
CAS Registry No. 1785349-89-4 dated Jun. 21, 2015.
CAS Registry No. 18474-60-7 dated Nov. 16, 1984.
CAS Registry No. 933731-79-4 dated Apr. 30, 2007.

Chalmers et al., "Binuclear Isomerism of Diphenyl Type, Part II.," Royal Society of New South Wales: 178-199 (1933).

Engelhardt et al., "Detailed structure-activity relationship of indolecarboxamides as H4 receptor ligands," European Journal of Medicinal Chemistry, 54: 660-668 (2012).

EPO Communication pursuant to Article 94(3) EPC for EP Application No. 16808753.4 dated Mar. 21, 2022.

Hiremath et al., "Synthesis of Substituted 7,12-Dehydroindolo[3,2-b][1,4]-benzodiazepin-5(6H)-ones & 1,2,3,4,5,6-Hexahydro[1,3]-diazepino[5,6-b]indole-1,5-diones," Indian Journal of Chemistry, 23B, 1058-1063 (1984).

Japanese Office Action for JP Application No. 2018-546774 dated Nov. 8, 2021 w/English Translation.

Karymova et al., "Bis(indolyl-3-)phthalides and their spectral properties," Chemistry of Heterocyclic Compounds, 25: 761-764 (1989).

Konyukhova et al., Rossiiskii Khmicheskii Zhurnal: Zhurnal Rossiiskogo Khimicheskogo Obshchestva im. D.l. Mendeleeva, vol. 29, No. 4: 467-468 (1984).

Laufer et al., "Investigations of SCIO-469-like compounds for the inhibition of p38 MAP kinase," Bioorganic & Medicinal Chemistry Letters, 19: 1461-1464 (2009).

* cited by examiner

INHIBITORS OF METALLO-BETA-LACTAMASES

RELATED APPLICATIONS

This application is a § 371 national-stage application based on International Application Number PCT/GB2016/053761, filed Nov. 30, 2016, which claims the benefit of GB 1521059.4, filed Nov. 30, 2015.

The work leading to this invention has received support from the Innovative Medicines Initiative Joint Undertaking under grant agreement no 115489, resources of which are composed of financial contribution from the European Union's Seventh Framework Programme (FP7/2007-2013) and EFPIA companies' in kind contribution.

INTRODUCTION

The present invention relates to compounds that function as inhibitors of metallo-beta-lactamases. The present invention also relates to processes for the preparation of these compounds, to pharmaceutical compositions comprising them, and to their use in the treatment of bacterial infections.

BACKGROUND OF THE INVENTION

Infections caused by pathogenic bacteria are common worldwide, and thus antibacterial medicines to treat such infections are highly sought. Currently, β-lactam antibacterials (BLAs) are amongst the most widely used antibacterial treatments.[1] However, the efficacy of BLAs is increasingly threatened by bacterial resistance, most importantly by the widespread dissemination of β-lactamases, which catalyse the hydrolysis and inactivation of BLA.[2]

In combination with a suitable penicillin, Class A β-lactamase inhibitors (BLIs) have been components of highly successful medicines (e.g. as in Augmentin). However, the zinc ion dependent Class B metallo-β-lactamases (MBLs, or carbapenemases), are structurally and mechanistically distinct from Class A, C and D serine β-lactamases (SBLs).[3] There is therefore a need for effective inhibitors of MBLs.

MBLs are particularly concerning because they hydrolyse most known BLAs, including the so called 'last resort' BLAs, such as some carbapenems, and confer resistance to BLAs in many pathogens. No clinically useful MBL inhibitors (MBLIs) are presently available.[4]

Though the problem of BLA resistance is most pronounced in developing countries, the number of cases of antimicrobial resistance (AMR) including Carbapenem-resistant Enterobacteriaceae (CRE) is substantially increasing worldwide.[5] It is notable that the estimates in these reports may under-represent the actual problem of BLA resistance, due to a lack of broad surveillance programs in some countries (many countries have not allocated, or do not have the resources for surveillance programs). A recent report shows NDM-1 is the most relevant MBL in the United Kingdom.[6] Similar reports are also appearing worldwide.

Thus, there remains a need for new treatments to combat MBL mediated antibacterial resistance.

The present invention was devised with the foregoing in mind.

SUMMARY OF THE INVENTION

In one aspect, the present invention provides a compound as defined herein, or a pharmaceutically acceptable salt or solvate thereof.

In another aspect, the present invention provides a compound as defined herein, or a pharmaceutically acceptable salt or solvate thereof, for use in the treatment of a bacterial infection.

In another aspect, the present invention provides a compound as defined herein, or a pharmaceutically acceptable salt or solvate thereof, in combination with a suitable antibacterial agent, for use in the treatment of a bacterial infection.

In another aspect, the present invention provides a pharmaceutical composition as defined herein which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in the treatment of bacterial infections.

In another aspect, the present invention provides a compound as defined herein, or a pharmaceutically acceptable salt or solvate thereof, or a pharmaceutical composition as defined herein, for use in the production of a metallo-beta-lactamase inhibitory effect.

In another aspect, the present invention provides a method of inhibiting a bacterial metallo-beta-lactamase in vitro or in vivo, said method comprising contacting a cell with an effective amount of a compound as defined herein, or a pharmaceutically acceptable salt or solvate thereof.

In another aspect, the present invention provides a method of treating a bacterial infection in a patient in need of such treatment, said method comprising administering to said patient a therapeutically effective amount of a compound as defined herein, or a pharmaceutically acceptable salt or solvate thereof, or a pharmaceutical composition as defined herein, in combination with a suitable antibacterial agent.

In another aspect, the present invention provides the use of a compound, as defined herein, in combination with a suitable antibacterial agent, for the treatment of a bacterial infection.

In another aspect, the present invention provides the use of a compound, as defined herein, for the inhibition of a metallo-beta-lactamase Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups and analogues thereof. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems.

Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a benzene ring fused to a 5- or 6-membered ring containing 1, 2 or 3 ring heteroatoms;
a pyridine ring fused to a 5- or 6-membered ring containing 1, 2 or 3 ring heteroatoms;
a pyrimidine ring fused to a 5- or 6-membered ring containing 1 or 2 ring heteroatoms;
a pyrrole ring fused to a 5- or 6-membered ring containing 1, 2 or 3 ring heteroatoms;
a pyrazole ring fused to a 5- or 6-membered ring containing 1 or 2 ring heteroatoms;
a pyrazine ring fused to a 5- or 6-membered ring containing 1 or 2 ring heteroatoms;
an imidazole ring fused to a 5- or 6-membered ring containing 1 or 2 ring heteroatoms;
an oxazole ring fused to a 5- or 6-membered ring containing 1 or 2 ring heteroatoms;
an isoxazole ring fused to a 5- or 6-membered ring containing 1 or 2 ring heteroatoms;
a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, CH$_2$, CH$_3$ group or heteroatom (i.e. NH) within a R$^1$ group is optionally substituted" suitably means that (any) one of the hydrogen radicals of the R$^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to a compound of formula I, or a pharmaceutically acceptable salt or solvate thereof, as shown below:

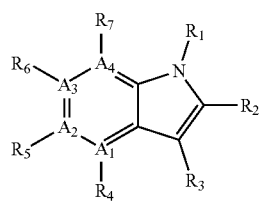

I wherein

A₁, A₂, A₃ or A₄ are selected from C or N, with the proviso that only one or two of A₁, A₂, A₃ or A₄ can be N;

R₁ is selected from hydrogen, (1-4C)alkyl or aryl, wherein each (1-4C)alkyl or aryl is optionally substituted by one or more substituent groups selected from oxo, halo, cyano, nitro, hydroxy, carboxy, $NR^{1A}R^{1B}$ or (1-4C)alkoxy, wherein $R^{1A}$ and $R^{1B}$ are each independently selected from hydrogen or (1-2C)alkyl;

R₂ is selected from:
(i) —C(O)OH;
(ii) —C(O)OR$_{2A}$, wherein R$_{2A}$ is selected from (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
(iii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
(iv) —C(O)NR$_{2D}$NR$_{2B}$R$_{2E}$; wherein R$_{2D}$ is selected from hydrogen or (1-6C)alkyl and R$_{2B}$ and R$_{2C}$ are as defined above;
(v) tetrazolyl;
(vi) triazolyl;
(vii) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl;
(viii) trifluoromethylketone;
and wherein $R^A$ is selected from halo, cyano, nitro or a group of the formula:

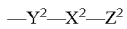

wherein
Y² is absent or a linker group of the formula —[CR$^{A1}$R$^{A2}$]$_m$— in which m is an integer selected from 1, 2, 3 or 4, and R$^{A1}$ and R$^{A2}$ are each independently selected from hydrogen or (1-2C)alkyl;
X² is absent or —O—, —C(O)—, —C(O)O—, —OC(O)—, —CH(OR$^{A3}$)—, —N(R$^{A3}$)—, —N(R$^{A3}$)—C(O)—, —N(R$^{A3}$)—C(O)O—, —C(O)—N(R$^{A3}$)—, —N(R$^{A3}$)C(O)N(R$^{A3}$)—, —SO—, —SO$_2$—, —S(O)$_2$N(R$^{A3}$)—, or —N(R$^{A3}$)SO$_2$— wherein R$^{A3}$ is selected from hydrogen or methyl; and
Z² is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z² is optionally further substituted by one or more substituent groups independently selected from oxo, halo, cyano, nitro, hydroxy, carboxy, NR$^{A4}$R$^{A5}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^{A4}$R$^{A5}$, NR$^{A4}$C(O)R$^{A5}$, NR$^{A4}$S(O)$_2$R$^{A5}$ and S(O)$_2$NR$^{A4}$R$^{A5}$; wherein R$^{A4}$ and R$^{A5}$ are each independently selected from hydrogen, (1-4C)alkyl or (3-6C)cycloalkyl or (3-6C)cycloalkyl(1-2C)alkyl; or R$^{A4}$ and R$^{A5}$ can be linked such that, together with the nitrogen atom to which they are attached, they form a 4-6 membered heterocyclic ring;

and wherein any alkyl, aryl, heterocyclyl or heteroaryl group present in a substituent group on Z² is optionally further substituted by halo, cyano, nitro, hydroxy, caboxy, NR$^{A6}$R$^{A7}$, (1-2C)alkoxy, or (1-2C)alkyl; wherein R$^{A6}$ and R$^{A7}$ are selected from hydrogen or (1-2C)alkyl;

R₃ is selected from hydrogen, halo, cyano, hydroxyl, aryl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more $R^B$;

$R^B$ is halo, cyano, nitro, hydroxy or a group:

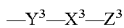

wherein
Y³ is absent or a linker group of the formula —[CR$^{B1}$R$^{B2}$]$_n$— in which n is an integer selected from 1, 2, 3 or 4, and R$^{B1}$ and R$^{B2}$ are each independently selected from hydrogen or (1-2C)alkyl;
X³ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$)—, —S—, —SO—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
Z³ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z³ is optionally further substituted by one or more substituent groups independently selected from oxo, halo, cyano, nitro, hydroxy, carboxy, NR$^{B5}$R$^{B6}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$; wherein R$^{B5}$ and R$^{B6}$ are each independently selected from hydrogen, (1-4C)alkyl or (3-6C)cycloalkyl or (3-6C)cycloalkyl(1-2C)alkyl; or R$^{B5}$ and R$^{B6}$ can be linked such that, together with the nitrogen atom to which they are attached, they form a 4-7 membered heterocyclic ring;
and wherein any alkyl, aryl, heterocyclyl or heteroaryl group present in a substituent group on Z³ is optionally further substituted by halo, cyano, nitro, hydroxy, caboxy, NR$^{B7}$R$^{B8}$, (1-2C)alkoxy, or (1-2C)alkyl; wherein R$^{B7}$ and R$^{B8}$ are selected from hydrogen or (1-2C)alkyl;
or R$^{B3}$ and Z³ can be linked such that, together with the nitrogen atom to which they are attached, they form a 4-7 membered heterocyclic ring, which is optionally substituted by oxo, halo, cyano, nitro, hydroxy, carboxy, NR$^{B5}$R$^{B6}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$;

R₄ is selected from hydrogen, halo, cyano, nitro, hydroxy or a group

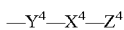

wherein
- $Y^4$ is absent or a linker group of the formula —[CR$^{4A}$R$^{4B}$]$_p$— in which p is an integer selected from 1 or 2, 3 or 4, and R$^{4A}$ and R$^{4B}$ are each independently selected from hydrogen or (1-2C)alkyl;
- $X^4$ is absent or —O—, —C(O)—, —C(O)O—, —OC(O)—, —CH(OR$^{4C}$)—, —N(R$^{4C}$)—N(R$^{4D}$)—C(O)—, —N(R$^{4D}$)—C(O)O—, —C(O)—N(R$^{4C}$)—, —N(R$^{4D}$)C(O)N(R$^{4C}$)—S—, —SO—, —SO$_2$—, —S(O)$_2$N(R$^{4C}$)—, or —N(R$^{4D}$)SO$_2$— wherein R$^{4C}$ and R$^{4D}$ are each independently selected from hydrogen or methyl; and
- $Z^4$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
  - and wherein $Z^4$ is optionally further substituted by one or more substituent groups independently selected from oxo, halo, cyano, nitro, hydroxy, carboxy, NR$^{4E}$R$^{4F}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{4E}$R$^{4F}$NR$^{4E}$C(O)R$^{4F}$, NR$^{4E}$S(O)$_2$R$^{4F}$ and S(O)$_2$ NR$^{4E}$R$^{4F}$; wherein R$^{4E}$ and R$^{4F}$ are each independently selected from hydrogen, (1-4C)alkyl or (3-6C)cycloalkyl or (3-6C)cycloalkyl(1-2C)alkyl; or R$^{4E}$ and R$^{4F}$ can be linked such that, together with the nitrogen atom to which they are attached, they form a 4-7 membered heterocyclic ring;
  - and wherein any alkyl, aryl, heterocyclyl or heteroaryl group present in a substituent group on $Z^4$ is optionally further substituted by halo, cyano, nitro, hydroxy, caboxy, NR$^{4G}$R$^{4H}$, (1-2C)alkoxy, or (1-2C)alkyl; wherein R$^{4G}$ and R$^{4H}$ are selected from hydrogen or (1-2C)alkyl;
- or R$^{4C}$ and $Z^4$ can be linked such that, together with the nitrogen atom to which they are attached, they form a 4-7 membered heterocyclic ring, which is optionally substituted by oxo, halo, cyano, nitro, hydroxy, carboxy, NR$^{4E}$R$^{4F}$ (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, or C(O)NR$^{4E}$R$^{4F}$, NR$^{4E}$C(O)R$^{4F}$, NR$^{4E}$S(O)$_2$R$^{4F}$ and S(O)$_2$ NR$^{4E}$R$^{4F}$;
- with the proviso that $R_4$ is only a group containing four or more non-hydrogen atoms when $R_3$ is a group comprising less than four non-hydrogen atoms;

$R_5$ is selected from hydrogen, halo, cyano, nitro, hydroxy or a group

—Y$^5$—X$^5$—Z$^5$ wherein:
- $Y^5$ is absent or a linker group of the formula —[CR$^{5A}$R$^{5B}$]$_q$— in which q is an integer selected from 1 or 2 and R$^{5A}$ and R$^{5B}$ are each independently selected from hydrogen or methyl;
- $X^5$ is absent or —O—, —C(O)—, —C(O)O—, —OC(O)—, —CH(OR$^{5C}$)—, —N(R$^{5C}$)—N(R$^{5D}$)—C(O)—, —N(R$^{5D}$)—C(O)O—, —C(O)—N(R$^{5C}$)—, —S—, —SO—, —SO$_2$—, —S(O)$_2$N(R$^{5C}$)—, or —N(R5$^{4D}$)SO$_2$— wherein R$^{4C}$ and R$^{4D}$ are each independently selected from hydrogen or methyl; and
- $Z^5$ is hydrogen or (1-4C)alkyl which is optionally further substituted by one or more substituent groups independently selected from oxo, halo, cyano, nitro, hydroxy, carboxy, NR$^{5E}$R$^{5F}$ or (1-2C)alkoxy; wherein R$^{5E}$ and R$^{5F}$ are each independently selected from hydrogen or (1-2C)alkyl;

$R_6$ is selected from hydrogen, halo, cyano, nitro, hydroxy or a group

—Y$^6$—X$^6$—Z$^6$ wherein:
- $Y^6$ is absent or a linker group of the formula —[CR$^{6A}$R$^{6B}$]$_q$— in which q is an integer selected from 1, 2, 3 or 4, and R$^{6A}$ and R$^{6B}$ are each independently selected from hydrogen or (1-2C)alkyl;
- $X^6$ is absent or —O—, —C(O)—, —C(O)O—, —OC(O)—, —CH(OR$^{6C}$)—, —N(R$^{6C}$)—, —N(R$^{6D}$)—C(O)—, —N(R$^{6D}$)—C(O)O—, —C(O)—N(R$^{6C}$)—, —N(R$^{6D}$)C(O)N(R$^{6C}$)—, —S—, —SO—, —SO$_2$—, —S(O)$_2$N(R$^{6C}$)—, or —N(R$^{6D}$)SO$_2$— wherein R$^{6C}$ and R$^{6D}$ are each independently selected from hydrogen or methyl; and
- $Z^6$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
  - and wherein $Z^6$ is optionally further substituted by one or more substituent groups independently selected from oxo, halo, cyano, nitro, hydroxy, carboxy, NR$^{6E}$R$^{6F}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{6E}$R$^{6F}$NR$^{6E}$C(O)R$^{6F}$, NR$^{6E}$S(O)$_2$R$^{6F}$ and S(O)$_2$ NR$^{6E}$R$^{6F}$; wherein R$^{6E}$ and R$^{6F}$ are each independently selected from hydrogen, (1-4C)alkyl or (3-6C)cycloalkyl or (3-6C)cycloalkyl(1-2C)alkyl; or R$^{6E}$ and R$^{6F}$ can be linked such that, together with the nitrogen atom to which they are attached, they form a 4-7 membered heterocyclic ring;
  - and wherein any alkyl, aryl, heterocyclyl or heteroaryl group present in a substituent group on $Z^6$ is optionally further substituted by halo, cyano, nitro, hydroxy, caboxy, NR$^{6G}$R$^{6H}$, (1-2C)alkoxy, or (1-2C)alkyl; wherein R$^{6G}$ and R$^{6H}$ are selected from hydrogen or (1-2C)alkyl;
- or R$^{6C}$ and $Z^6$ can be linked such that, together with the nitrogen atom to which they are attached, they form a 4-7 membered heterocyclic ring, which is optionally substituted by oxo, halo, cyano, nitro, hydroxy, carboxy, NR$^{6E}$R$^{6F}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, or C(O)NR$^{6E}$R$^{6F}$, NR$^{6E}$C(O)R$^{6F}$NR$^{6E}$S(O)$_2$R$^{6F}$ and S(O)$_2$ NR$^{6E}$R$^{6F}$;

$R_7$ is selected from hydrogen, halo, cyano, nitro, hydroxy or a group

—Y$^7$—X$^7$—Z$^7$ wherein:
- $Y^7$ is absent or a linker group of the formula —[CR$^{7A}$R$^{7B}$]$_q$— in which q is an integer selected from 1, 2, 3 or 4, and R$^{7A}$ and R$^{7B}$ are each independently selected from hydrogen or (1-2C)alkyl;

$X^7$ is absent or —O—, —C(O)—, —C(O)O—, —OC(O)—, —CH(OR$^{7C}$)—, —N(R$^{7C}$)—, —N(R$^{7D}$)—C(O)—, —N(R$^{7D}$)—C(O)O—, —C(O)—N(R$^{7C}$)—, —N(R$^{7D}$)C(O)N(R$^{7C}$)—, —S—, —SO—, —SO$_2$—, —S(O)$_2$N(R$^{7C}$)—, or —N(R$^{7D}$)SO$_2$— wherein R$^{7C}$ and R$^{7D}$ are each independently selected from hydrogen or methyl; and $Z^7$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^7$ is optionally further substituted by one or more substituent groups independently selected from oxo, halo, cyano, nitro, hydroxy, carboxy, NR$^{7E}$R$^{7F}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{7E}$R$^{7F}$, NR$^{7E}$C(O)R$^{7F}$, NR$^{7E}$S(O)$_2$R$^{7F}$ and S(O)$_2$NR$^{7E}$R$^{7F}$; wherein R$^{7E}$ and R$^{7F}$ are each independently selected from hydrogen, (1-4C)alkyl or (3-6C)cycloalkyl or (3-6C)cycloalkyl(1-2C)alkyl; or R$^{7E}$ and R$^{7F}$ can be linked such that, together with the nitrogen atom to which they are attached, they form a 4-7 membered heterocyclic ring;

and wherein any alkyl, aryl, heterocyclyl or heteroaryl group present in a substituent group on $Z^7$ is optionally further substituted by halo, cyano, nitro, hydroxy, caboxy, NR$^{7G}$R$^{7H}$, (1-2C)alkoxy, or (1-2C)alkyl; wherein R$^{7G}$ and R$^{7H}$ are selected from hydrogen or (1-2C)alkyl;

or R$^{7C}$ and $Z^7$ can be linked such that, together with the nitrogen atom to which they are attached, they form a 4-7 membered heterocyclic ring, which is optionally substituted by oxo, halo, cyano, nitro, hydroxy, carboxy, NR$^{7E}$R$^{7F}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, or C(O)NR$^{7E}$R$^{7F}$, NR$^{7E}$C(O)R$^{7F}$, NR$^{7E}$S(O)$_2$R$^{7F}$ and S(O)$_2$NR$^{7E}$R$^{7F}$.

In the compounds of formula I defined above, $R_4$ is only a group containing four or more non-hydrogen atoms when $R_3$ is a group comprising less than four non-hydrogen atoms. This means that when $R_4$ is only a group selected from the listed options that comprises four or more non-hydrogen atoms (i.e. typically four or more atoms selected C, N, O or S), when $R_3$ is a small substituent group comprising less than four non-hydrogen atoms (i.e. typically C, N, O or S).

Particular compounds of the invention include, for example, compounds of the formula I, or pharmaceutically acceptable salts and/or solvates thereof, wherein, unless otherwise stated, each of $A_1$, $A_2$, $A_3$, $A_4$, $R_1$, $R_2$, $R_3$, $R_4$, $R_5$, $R_6$ and $R_7$ and any associated substituent groups has any of the meanings defined hereinbefore or in any of paragraphs (1) to (76) hereinafter:—

(1) $A_1$, $A_2$, $A_3$ or $A_4$ are selected from C or N, with the proviso that only one of $A_1$, $A_2$, $A_3$ or $A_4$ can be N;
(2) $A_1$, $A_2$ or $A_4$ are selected from C or N and $A_3$ is C, with the proviso that only one of $A_1$, $A_2$ or $A_4$ can be N;
(3) $A_1$, $A_2$, $A_3$ or $A_4$ are C;
(4) $R_1$ is selected from hydrogen or (1-4C)alkyl which is optionally substituted by one or more substituent groups selected from oxo, halo, cyano, nitro, hydroxy, carboxy, NR$^{1A}$R$^{1B}$ or (1-4C)alkoxy, wherein R$^{1A}$ and R$^{1B}$ are each independently selected from hydrogen or (1-2C)alkyl;
(5) $R_1$ is selected from hydrogen or (1-4C)alkyl which is optionally substituted by one or more substituent groups selected from oxo, halo, cyano, carboxy, NR$^{1A}$R$^{1B}$ or (1-4C)alkoxy, wherein R$^{1A}$ and R$^{1B}$ are each independently selected from hydrogen or (1-2C)alkyl;
(6) $R_1$ is selected from hydrogen, (1-4C)alkyl or phenyl, wherein each (1-4C)alkyl or phenyl is optionally substituted by one or more substituent groups selected from oxo, halo, cyano, NR$^{1A}$R$^{1B}$ or (1-2C)alkoxy, wherein R$^{1A}$ and R$^{1B}$ are each independently selected from hydrogen or methyl;
(7) $R_1$ is selected from hydrogen or (1-4C)alkyl which is optionally substituted by one or more substituent groups selected from oxo, halo, cyano, NR$^{1A}$R$^{1B}$ or (1-2C)alkoxy, wherein R$^{1A}$ and R$^{1B}$ are each independently selected from hydrogen or methyl;
(8) $R_1$ is selected from hydrogen, (1-4C)alkyl or phenyl, wherein each (1-4C)alkyl or phenyl is optionally substituted by one or more substituent groups selected from oxo, halo, or (1-2C)alkoxy;
(9) $R_1$ is selected from hydrogen or (1-4C)alkyl which is optionally substituted by one or more substituent groups selected from oxo, halo, or (1-2C)alkoxy;
(10) $R_1$ is selected from hydrogen or (1-4C)alkyl which is optionally substituted by one or more substituent groups selected from oxo, fluoro or chloro;
(11) $R_1$ is selected from hydrogen or (1-4C)alkyl which is optionally substituted by one or more fluoro groups;
(12) $R_1$ is selected from hydrogen or (1-2C)alkyl;
(13) $R_1$ is hydrogen;
(14) $R_2$ is selected from:
  (i) —C(O)OH;
  (ii) —C(O)OR$_{2A}$, wherein R$_{2A}$ is selected from (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^4$;
  (iii) —C(O) NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^4$;
  (iv) —C(O)NR$_{2D}$NR$_{2B}$R$_{2C}$; wherein R$_{2D}$ is selected from hydrogen or (1-6C)alkyl and R$_{2B}$ and R$_{2C}$ are as defined above;
  (v) tetrazolyl;
  (vi) triazolyl;
  (vii) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl;
  (viii) trifluoromethylketone;
  and wherein R$^4$ is selected from halo, cyano, nitro or a group of the formula:

—Y$^2$—X$^2$—X$^2$ wherein
- $Y^2$ is absent or a linker group of the formula $-[CR^{41}R^{42}]_m-$ in which m is an integer selected from 1 or 2, and $R^{41}$ and $R^{42}$ are each independently selected from hydrogen or (1-2C)alkyl;
- $X^2$ is absent or $-O-$, $-C(O)-$, $-C(O)O-$, $-OC(O)-$, $-N(R^{43})-$, $-N(R^{43})C(O)$, $-N(R^{43})-C(O)O-$, $-C(O)-N(R^{43})-$, $-N(R^{43})C(O)N(R^{43})$, $-SO_2-$, $-S(O)_2N(R^{43})-$, or $-N(R^{43})SO_2-$ wherein $R^{43}$ is selected from hydrogen or methyl; and
- $Z^2$ is hydrogen, (1-6C)alkyl, aryl, (3-6C)cycloalkyl, (3-6C)cycloalkenyl, heteroaryl or heterocyclyl;
  - and wherein $Z^2$ is optionally further substituted by one or more substituent groups independently selected from oxo, halo, cyano, nitro, hydroxy, carboxy, $NR^{44}R^{45}$, (1-4C)alkoxy, (1-4C)alkyl, (3-8C)cycloalkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, $C(O)NR^{44}R^{45}$, $NR^{44}C(O)R^{45}$, $NR^{44}S(O)_2R^{45}$ and $S(O)_2NR^{44}R^{45}$; wherein $R^{44}$ and $R^{45}$ are each independently selected from hydrogen, or (1-4C)alkyl; or $R^{44}$ and $R^{45}$ can be linked such that, together with the nitrogen atom to which they are attached, they form a 4-6 membered heterocyclic ring;
  - and wherein any alkyl, aryl, heterocyclyl or heteroaryl group present in a substituent group on $Z^2$ is optionally further substituted by halo, cyano, hydroxy, $NR^{46}R^{47}$, (1-2C)alkoxy, or (1-2C)alkyl; wherein $R^{46}$ and $R^{47}$ are selected from hydrogen or (1-2C)alkyl;

(15) $R_2$ is selected from:
- (i) $-C(O)OH$;
- (ii) $-C(O)OR_{2A}$, wherein $R_{2A}$ is selected from (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^4$;
- (iii) $-C(O)NR_{2B}R_{2C}$; wherein $R_{2B}$ and $R_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^4$;
- (iv) $-C(O)NR_{2D}NR_{2B}R_{2C}$; wherein $R_{2D}$ is selected from hydrogen or (1-6C)alkyl and $R_{2B}$ and $R_{2C}$ are as defined above;
- (v) tetrazolyl;
- (vi) triazolyl;
- (vii) $-B(OR_{2F})(OR_{2G})$, wherein $R_{2F}$ and $R_{2G}$ are each independently selected from hydrogen, (1-6C)alkyl or $R_{2F}$ and $R_{2G}$ are linked such that, together with the B and O atoms, they form a 5 or 6-membered heterocyclic ring, which is optionally substituted by (1-2C)alkyl;
- (viii) trifluoromethylketone;

and wherein $R^4$ is selected from halo, cyano, nitro or a group of the formula:

$-Y^2-X^2-Z^2$ wherein
- $Y^2$ is absent or a linker group of the formula $-[CR^{41}R^{42}]_m-$ in which m is an integer selected from 1 or 2, and $R^{41}$ and $R^{42}$ are each independently selected from hydrogen or (1-2C)alkyl;
- $X^2$ is absent or $-O-$, $-C(O)-$, $-C(O)O-$, $-OC(O)-$, $-N(R^{43})-$, $-N(R^{43})C(O)-$, $-N(R^{43})-C(O)O-$, $-C(O)-N(R^{43})-$, $-SO_2-$, wherein $R^{43}$ is selected from hydrogen or methyl; and
- $Z^2$ is hydrogen, (1-6C)alkyl, aryl, (3-6C)cycloalkyl, (3-6C)cycloalkenyl, heteroaryl or heterocyclyl;
  - and wherein $Z^2$ is optionally further substituted by one or more substituent groups independently selected from oxo, halo, cyano, nitro, hydroxy, carboxy, $NR^{44}R^{45}$, (1-4C)alkoxy, (1-4C)alkyl, (3-8C)cycloalkyl, (1-4C)alkanoyl, aryl, heterocyclyl, heteroaryl, $C(O)NR^{44}R^{45}$ or $NR^{44}C(O)R^{45}$; wherein $R^{44}$ and $R^{45}$ are each independently selected from hydrogen, or (1-2C)alkyl; or $R^{44}$ and $R^{45}$ can be linked such that, together with the nitrogen atom to which they are attached, they form a 4-6 membered heterocyclic ring;
  - and wherein any alkyl, aryl, heterocyclyl or heteroaryl group present in a substituent group on $Z^2$ is optionally further substituted by halo, hydroxy, $NR^{46}R^{47}$, (1-2C)alkoxy, or (1-2C)alkyl; wherein $R^{46}$ and $R^{47}$ are selected from hydrogen or (1-2C)alkyl;

(16) $R_2$ is selected from:
- (i) $-C(O)OH$;
- (ii) $-C(O)OR_{2A}$, wherein $R_{2A}$ is selected from (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^4$;
- (iii) $-C(O)NR_{2B}R_{2C}$; wherein $R_{2B}$ and $R_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^4$;
- (iv) $-C(O)NR_{2D}NR_{2B}R_{2C}$; wherein $R_{2D}$ is selected from hydrogen or (1-6C)alkyl and $R_{2B}$ and $R_{2C}$ are as defined above;
- (v) tetrazolyl;
- (vi) triazolyl;
- (vii) $-B(OR_{2F})(OR_{2G})$, wherein $R_{2F}$ and $R_{2G}$ are each independently selected from hydrogen, (1-6C)alkyl or $R_{2F}$ and $R_{2G}$ are linked such that, together with the B and O atoms, they form a 5 or 6-membered heterocyclic ring, which is optionally substituted by (1-2C)alkyl;
- (viii) trifluoromethylketone;

and wherein $R^4$ is selected from halo, cyano, nitro or a group of the formula:

$-Y^2-X^2-Z^2$ wherein
- $Y^2$ is absent or a linker group of the formula $-[CR^{41}R^{42}]_m-$ in which m is an integer selected from 1 or 2, and $R^{41}$ and $R^{42}$ are each independently selected from hydrogen or methyl;
- $X^2$ is absent or $-C(O)-$, $-N(R^{43})-C(O)-$, $-C(O)-N(R^{43})-$, $-SO_2-$, wherein $R^{43}$ is selected from hydrogen or methyl; and $Z^2$ is hydrogen, (1-6C)alkyl, aryl, (3-6C)cycloalkyl, heteroaryl or heterocyclyl;

and wherein $Z^2$ is optionally further substituted by one or more substituent groups independently selected from oxo, halo, cyano, nitro, hydroxy, carboxy, $NR^{A4}R^{A5}$, (1-4C)alkoxy, (1-4C)alkyl, aryl, heterocyclyl, heteroaryl, $C(O)NR^{A4}R^{A5}$ or $NR^{A4}C(O)R^{A5}$; wherein $R^{A4}$ and $R^{A5}$ are each independently selected from hydrogen, or (1-2C)alkyl;

and wherein any alkyl, aryl, heterocyclyl or heteroaryl group present in a substituent group on $Z^2$ is optionally further substituted by halo, hydroxy, $NR^{A6}R^{A7}$, (1-2C)alkoxy, or (1-2C) alkyl; wherein $R^{A6}$ and $R^{A7}$ are selected from hydrogen or (1-2C)alkyl;

(17) $R_2$ is selected from:
  (i) —C(O)OH;
  (ii) —C(O)OR$_{2A}$, wherein R$_{2A}$ is selected from (1-6C) alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
  (iii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C) alkyl, heterocyclyl or heterocyclyl-(1-2C)alkyl, each of which is optionally substituted by one or more substituent groups $R^A$;
  (iv) —C(O)NR$_{2D}$NR$_{2B}$R$_{2C}$; wherein R$_{2D}$ is selected from hydrogen or (1-6C)alkyl and R$_{2B}$ and R$_{2C}$ are as defined above;
  (v) tetrazolyl;
  (vi) triazolyl;
  (vii) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl;
  (viii) trifluoromethylketone;

and wherein $R^A$ is selected from halo, cyano, nitro or a group of the formula:

—$X^2$—$Z^2$ wherein
  $X^2$ is absent or —C(O)—, —N(R$^{A3}$)—C(O)—, —C(O)—N(R$^{A3}$)—, —SO$_2$—, wherein $R^{A3}$ is selected from hydrogen or methyl; and
  $Z^2$ is hydrogen, (1-6C)alkyl, aryl, (3-6C)cycloalkyl, heteroaryl or heterocyclyl;
    and wherein $Z^2$ is optionally further substituted by one or more substituent groups independently selected from oxo, halo, cyano, hydroxy, carboxy, $NR^{A4}R^{A5}$, (1-4C)alkoxy, (1-4C)alkyl, aryl, C(O)NR$^{A4}$R$^{A5}$ or NR$^{A4}$C(O)R$^{A5}$; wherein $R^{A4}$ and $R^{A5}$ are each independently selected from hydrogen, or (1-2C)alkyl;
    and wherein any alkyl, aryl, heterocyclyl or heteroaryl group present in a substituent group on $Z^2$ is optionally further substituted by halo, hydroxy, or (1-2C)alkyl;

(18) $R_2$ is selected from:
  (i) —C(O)OH;
  (ii) —C(O)OR$_{2A}$, wherein R$_{2A}$ is selected from (1-6C) alkyl, (3-8C)cycloalkyl, aryl, heteroaryl or heterocyclyl, each of which is optionally substituted by one or more substituent groups $R^A$;
  (iii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C) alkyl, heterocyclyl or heterocyclyl-(1-2C)alkyl, each of which is optionally substituted by one or more substituent groups $R^A$;
  (iv) —C(O)NR$_{2D}$NR$_{2B}$R$_{2C}$; wherein R$_{2D}$ is selected from hydrogen or (1-2C)alkyl and R$_{2B}$ and R$_{2C}$ are as defined above;
  (v) tetrazolyl;
  (vi) triazolyl;
  (vii) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl;
  (viii) trifluoromethylketone;

and wherein $R^A$ is selected from halo, cyano, nitro or a group of the formula:

—$X^2$—$Z^2$ wherein
  $X^2$ is absent or —C(O)—, —N(R$^{A3}$)—C(O)—, —C(O)—N(R$^{A3}$)—, —SO$_2$—, wherein $R^{A3}$ is selected from hydrogen or methyl; and
  $Z^2$ is hydrogen, (1-6C)alkyl, aryl, (3-6C)cycloalkyl, heteroaryl or heterocyclyl;
    and wherein $Z^2$ is optionally further substituted by one or more substituent groups independently selected from oxo, halo, cyano, hydroxy, carboxy, $NR^{A4}R^{A5}$, (1-4C)alkoxy, (1-4C)alkyl, aryl, C(O)NR$^{A4}$R$^{A5}$ or NR$^{A4}$C(O)R$^{A5}$; wherein $R^{A4}$ and $R^{A5}$ are each independently selected from hydrogen, or (1-2C)alkyl;

(19) $R_2$ is selected from:
  (i) —C(O)OH;
  (ii) —C(O)OR$_{2A}$, wherein R$_{2A}$ is selected from (1-6C) alkyl, (3-8C)cycloalkyl, aryl, heteroaryl or heterocyclyl, each of which is optionally substituted by one or more substituent groups $R^A$;
  (iii) —C(O)NR$_{2B}$R$_{2C}$; wherein R$_{2B}$ and R$_{2C}$ are each independently selected from hydrogen, (1-6C)alkyl, (3-8C)cycloalkyl, aryl, heteroaryl or heterocyclyl, each of which is optionally substituted by one or more substituent groups $R^A$;
  (iv) —C(O)NR$_{2D}$NR$_{2B}$R$_{2C}$; wherein R$_{2D}$ is selected from hydrogen or (1-2C)alkyl and R$_{2B}$ and R$_{2C}$ are as defined above;
  (v) tetrazolyl;
  (vi) triazolyl;
  (vii) —B(OR$_{2F}$)(OR$_{2G}$), wherein R$_{2F}$ and R$_{2G}$ are each independently selected from hydrogen, (1-4C)alkyl or R$_{2F}$ and R$_{2G}$ are linked such that, together with the B and O atoms, they form a 5 or 6-membered heterocyclic ring, which is optionally substituted by (1-2C)alkyl;
  (viii) trifluoromethylketone;

and wherein $R^A$ is selected from halo, cyano, nitro or a group of the formula:

—$X^2$—$Z^2$ wherein
X² is absent or —C(O)—, —N(R^{A3})—C(O)—, —C(O)—N(R^{A3})—, —SO₂—, wherein R^{A3} is selected from hydrogen or methyl; and
Z² is hydrogen, (1-6C)alkyl, aryl, (3-6C)cycloalkyl, heteroaryl or heterocyclyl;
and wherein Z² is optionally further substituted by one or more substituent groups independently selected from oxo, halo, cyano, hydroxy, NR^{44}R^{45}, (1-4C)alkoxy or (1-4C)alkyl, wherein R^{44} and R^{45} are each independently selected from hydrogen, or (1-2C)alkyl;

(20) R₂ is selected from:
(i) —C(O)OH;
(ii) —C(O)OR_{2A}, wherein R_{2A} is selected from (1-6C) alkyl, (3-8C)cycloalkyl, aryl, heteroaryl or heterocyclyl, each of which is optionally substituted by one or more substituent groups R^{A};
(iii) —C(O)NR_{2B}R_{2C}; wherein R_{2B} and R_{2C} are each independently selected from hydrogen, (1-6C)alkyl, (3-8C)cycloalkyl, aryl, heteroaryl or heterocyclyl, each of which is optionally substituted by one or more substituent groups R^{A};
(iv) —C(O)NR_{2D}NR_{2B}R_{2C}; wherein R_{2D} is selected from hydrogen or (1-2C)alkyl and R_{2B} and R_{2C} are as defined above;
(v) tetrazolyl;
(vi) triazolyl;
(vii) —B(OR_{2F})(OR_{2G}), wherein R_{2F} and R_{2G} are each independently selected from hydrogen, (1-4C)alkyl or R_{2F} and R_{2G} are linked such that, together with the B and O atoms, they form a 5 or 6-membered heterocyclic ring, which is optionally substituted by (1-2C)alkyl;
(viii) trifluoromethylketone;
and wherein R^{A} is selected from halo, cyano, nitro or a group of the formula:

—X²—Z² wherein
X² is absent or —C(O)—, —SO₂—; and
Z² is hydrogen, (1-6C)alkyl, aryl, or heteroaryl;
and wherein Z² is optionally further substituted by one or more substituent groups independently selected from halo, hydroxy, NR^{44}R^{45}, (1-4C) alkoxy or (1-4C)alkyl, wherein R^{44} and R^{45} are each independently selected from hydrogen, or (1-2C)alkyl;

(21) R₂ is selected from:
(i) —C(O)OH;
(ii) —C(O)OR_{2A}, wherein R_{2A} is selected from (1-6C) alkyl, (3-8C)cycloalkyl, aryl, heteroaryl or heterocyclyl, each of which is optionally substituted by one or more substituent groups R^{A};
(iii) —C(O)NR_{2B}R_{2C}; wherein R_{2B} and R_{2C} are each independently selected from hydrogen, (1-6C)alkyl, (3-8C)cycloalkyl, aryl or heteroaryl, each of which is optionally substituted by one or more substituent groups R^{A};
(iv) —C(O)NR_{2D}NR_{2B}R_{2C}; wherein R_{2D} is selected from hydrogen or (1-2C)alkyl and R_{2B} and R_{2C} are as defined above;
(v) tetrazolyl;
(vi) triazolyl;
(vii) —B(OR_{2F})(OR_{2G}), wherein R_{2F} and R_{2G} are each independently selected from hydrogen, (1-4C)alkyl or R_{2F} and R_{2G} are linked such that, together with the B and O atoms, they form a 5 or 6-membered heterocyclic ring, which is optionally substituted by (1-2C)alkyl;
(viii) trifluoromethylketone;
and wherein R^{A} is selected from halo, cyano, nitro or a group of the formula:

—X²—Z² wherein
X² is absent or —C(O)—, —SO₂—; and
Z² is hydrogen, (1-6C)alkyl, aryl, or heteroaryl;
and wherein Z² is optionally further substituted by one or more substituent groups independently selected from halo, hydroxy, NR^{44}R^{45}, (1-4C) alkoxy or (1-4C)alkyl, wherein R^{44} and R^{45} are each independently selected from hydrogen, or (1-2C)alkyl;

(22) R₂ is selected from:
(i) —C(O)OH;
(ii) —C(O)NR_{2B}R_{2C}; wherein R_{2B} and R_{2C} are each independently selected from hydrogen, (1-6C)alkyl, (3-8C)cycloalkyl, aryl, heteroaryl or heterocyclyl, each of which is optionally substituted by one or more substituent groups R^{A};
(iii) —C(O)NR_{2D}NR_{2B}R_{2C}; wherein R_{2D} is selected from hydrogen or (1-2C)alkyl and R_{2B} and R_{2C} are as defined above;
(iv) tetrazolyl;
(v) —B(OR_{2F})(OR_{2G}), wherein R_{2F} and R_{2G} are each independently selected from hydrogen, (1-4C)alkyl or R_{2F} and R_{2G} are linked such that, together with the B and O atoms, they form a 5 or 6-membered heterocyclic ring, which is optionally substituted by (1-2C)alkyl;
and wherein R^{A} is selected from halo, cyano, or a group of the formula:

—X²—Z² wherein
X² is absent or —C(O)—, —SO₂—; and
Z² is hydrogen, (1-6C)alkyl, aryl, or heteroaryl;
and wherein Z² is optionally further substituted by one or more substituent groups independently selected from halo, hydroxy, NR^{44}R^{45} (1-4C) alkoxy or (1-4C)alkyl, wherein R^{44} and R^{45} are each independently selected from hydrogen, or (1-2C)alkyl;

(23) R₂ is selected from:
(i) —C(O)OH;
(ii) —C(O)NR_{2B}R_{2C}; wherein R_{2B} and R_{2C} are each independently selected from hydrogen, (1-6C)alkyl, (3-8C)cycloalkyl, aryl or heteroaryl, each of which is optionally substituted by one or more substituent groups R^{A};
(iii) —C(O)NR_{2D}NR_{2B}R_{2C}; wherein R_{2D} is selected from hydrogen or (1-2C)alkyl and R_{2B} and R_{2C} are as defined above;
(iv) tetrazolyl;
(v) —B(OR_{2F})(OR_{2G}), wherein R_{2F} and R_{2G} are each independently selected from hydrogen, (1-4C)alkyl or R_{2F} and R_{2G} are linked such that, together with the B and O atoms, they form a 5 or 6-membered heterocyclic ring, which is optionally substituted by (1-2C)alkyl;
and wherein R^{A} is selected from halo, cyano, or a group of the formula:

—X²—Z² wherein
X$^2$ is absent or —C(O)—, —SO$_2$—; and
Z$^2$ is hydrogen, (1-6C)alkyl, aryl, or heteroaryl;
and wherein Z$^2$ is optionally further substituted by one or more substituent groups independently selected from halo, hydroxy, NR$^{A4}$R$^{A5}$, (1-4C)alkoxy or (1-4C)alkyl, wherein R$^{A4}$ and R$^{A5}$ are each independently selected from hydrogen, or (1-2C)alkyl;

(24) R$_2$ is selected from:
(i) —C(O)OH;
(ii) —C(O)NR$_{2B}$R$_{2C}$; wherein R$_{2B}$ and R$_{2C}$ are each independently selected from hydrogen, (1-6C)alkyl, aryl or heteroaryl, each of which is optionally substituted by one or more substituent groups R$^A$;
(iii) —C(O)NR$_{2D}$NR$_{2B}$R$_{2C}$; wherein R$_{2D}$ is selected from hydrogen or methyl and R$_{2B}$ and R$_{2C}$ are as defined above;
(iv) tetrazolyl;
and wherein R$^A$ is selected from halo, cyano, or a group of the formula:

—X$^2$—Z$^2$ wherein
X$^2$ is absent or —C(O)—, —SO$_2$—; and
Z$^2$ is hydrogen, (1-4C)alkyl, phenyl, or a 5- or 6-membered heteroaryl; and wherein Z$^2$ is optionally further substituted by one or more substituent groups independently selected from halo, hydroxyl or (1-4C)alkyl;

(25) R$_2$ is selected from:
(i) —C(O)OH;
(ii) —C(O)NR$_{2B}$R$_{2C}$; wherein R$_{2B}$ and R$_{2C}$ are each independently selected from hydrogen, (1-6C)alkyl, aryl or heteroaryl, each of which is optionally substituted by one or more substituent groups R$^A$;
(iii) —C(O)NR$_{2D}$NR$_{2B}$R$_{2C}$; wherein R$_{2D}$ is selected from hydrogen or methyl and R$_{2B}$ and R$_{2C}$ are as defined above;
(iv) tetrazolyl;
and wherein R$^A$ is selected from halo, cyano or SO$_2$CH$_3$;

(26) R$_2$ is —C(O)OH;

(27) R$_3$ is selected from hydrogen, halo, cyano, hydroxyl, aryl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more R$^B$;
R$^B$ is halo, cyano, nitro, hydroxy or a group:

—Y$^3$—X$^3$—Z$^3$ wherein
Y$^3$ is absent or a linker group of the formula —[CR$^{B1}$R$^{B2}$]$_n$— in which n is an integer selected from 1 or 2 and R$^{B1}$ and R$^{B2}$ are each independently selected from hydrogen or (1-2C)alkyl;
X$^3$ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$)—, —S—, —SO—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
Z$^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein Z$^3$ is optionally further substituted by one or more substituent groups independently selected from oxo, halo, cyano, nitro, hydroxy, carboxy, NR$^{B5}$R$^{B6}$, (1-4C)alkoxy, (1-4C)alkyl, (3-8C)cycloalkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, C(O) NR$^{B5}$R$^{B6}$, NR$^{5B}$C(O)R$^{B6}$; wherein R$^{B5}$ and R$^{B6}$ are each independently selected from hydrogen or (1-4C)alkyl; or R$^{B5}$ and R$^{B6}$ can be linked such that, together with the nitrogen atom to which they are attached, they form a 4-7 membered heterocyclic ring;
and wherein any alkyl, aryl, heterocyclyl or heteroaryl group present in a substituent group on Z$^3$ is optionally further substituted by halo, cyano, nitro, hydroxy, caboxy, NR$^{B7}$R$^{B8}$, (1-2C)alkoxy, or (1-2C)alkyl; wherein R$^{B7}$ and R$^{B8}$ are selected from hydrogen or (1-2C)alkyl;
or R$^{B3}$ and Z$^3$ can be linked such that, together with the nitrogen atom to which they are attached, they form a 4-7 membered heterocyclic ring, which is optionally substituted by oxo, halo, cyano, nitro, hydroxy, carboxy, NR$^{B5}$R$^{B6}$, (1-4C)alkoxy, (1-4C) alkyl;

(28) R$_3$ is selected from hydrogen, halo, cyano, hydroxyl, aryl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more R$^B$;
R$^B$ is halo, cyano, nitro, hydroxy or a group:

—Y$^3$—X$^3$—Z$^3$ wherein
Y$^3$ is absent or a linker group of the formula —[CR$^{B1}$R$^{B2}$]$_n$— in which n is an integer selected from 1 or 2 and R$^{B1}$ and R$^{B2}$ are each independently selected from hydrogen or (1-2C)alkyl;
X$^3$ is absent or —O—, —C(O)—, —C(O)O—, —OC(O)—, —N(R$^{B3}$)—, —N(R$^{B4}$)—C(O), —N(R$^{B4}$)—C(O)O—, —C(O)—N(R$^{B3}$)—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
Z$^3$ is hydrogen, (1-6C)alkyl, (2-6C)alkenyl, (2-6C) alkynyl, aryl, (3-6C)cycloalkyl, (3-6C)cycloalkenyl, heteroaryl or heterocyclyl;
and wherein Z$^3$ is optionally further substituted by one or more substituent groups independently selected from oxo, halo, cyano, nitro, hydroxy, carboxy, NR$^{B5}$R$^{B6}$, (1-4C)alkoxy, (1-4C)alkyl, (3-8C)cycloalkyl, aryl, heterocyclyl, heteroaryl, C(O)NR$^{B5}$R$^{B6}$, NR$^{B5}$C(O)R$^{B6}$; wherein R$^{B5}$ and R$^{B6}$ are each independently selected from hydrogen or (1-4C)alkyl; or R$^{B5}$ and R$^{B6}$ can be linked such that, together with the nitrogen atom to which they are attached, they form a 4-6 membered heterocyclic ring;
and wherein any alkyl, aryl, heterocyclyl or heteroaryl group present in a substituent group on Z$^3$ is optionally further substituted by halo, hydroxy, NR$^{B7}$R$^{B8}$, (1-2C)alkoxy, or (1-2C) alkyl; wherein R$^{B7}$ and R$^{B8}$ are selected from hydrogen or (1-2C)alkyl;
or R$^{B3}$ and Z$^3$ can be linked such that, together with the nitrogen atom to which they are attached, they form a 4-6 membered heterocyclic ring, which is optionally substituted by oxo, halo, hydroxy, $NR^{B5}R^{B6}$, (1-4C)alkoxy or (1-4C)alkyl;

(29) $R_3$ is selected from hydrogen, halo, cyano, hydroxyl, aryl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more $R^B$;

$R^B$ is halo, cyano, nitro, hydroxy or a group:

—$Y^3$—$X^3$—$Z^3$ wherein
  $Y^3$ is absent or a linker group of the formula —$[CR^{B1}R^{B2}]_n$— in which n is an integer selected from 1 or 2 and $R^{B1}$ and $R^{B2}$ are each independently selected from hydrogen or (1-2C)alkyl;
  $X^3$ is absent or —O—, —C(O)—, —C(O)O—, —OC(O)—, —N($R^{B3}$)—, —N($R^{B4}$)—C(O), —N($R^{B4}$)—C(O)O—, —C(O)—N($R^{B3}$)—, —SO$_2$—, —S(O)$_2$N($R^{B3}$)—, or —N($R^{B4}$)SO$_2$— wherein $R^{B3}$ and $R^{B4}$ are each independently selected from hydrogen or methyl; and
  $Z^3$ is hydrogen, (1-6C)alkyl, aryl, (3-6C)cycloalkyl, (3-6C)cycloalkenyl, heteroaryl or heterocyclyl;
  and wherein $Z^3$ is optionally further substituted by one or more substituent groups independently selected from oxo, halo, cyano, nitro, hydroxy, carboxy, $NR^{B5}R^{B6}$, (1-4C)alkoxy, (1-4C)alkyl, aryl, C(O)$NR^{B5}R^{B6}$, $NR^{B5}$(O)$R^{B6}$; wherein $R^{B5}$ and $R^{B6}$ are each independently selected from hydrogen or (1-4C)alkyl;
  and wherein any alkyl or aryl group present in a substituent group on $Z^3$ is optionally further substituted by halo, hydroxy, $NR^{B7}R^{B8}$, (1-2C)alkoxy, or (1-2C)alkyl; wherein $R^{B7}$ and $R^{B8}$ are selected from hydrogen or (1-2C)alkyl;
  or $R^{B3}$ and $Z^3$ can be linked such that, together with the nitrogen atom to which they are attached, they form a 4-6 membered heterocyclic ring, which is optionally substituted by oxo, halo, hydroxy, $NR^{B5}R^{B6}$, (1-4C)alkoxy or (1-4C)alkyl;

(30) $R_3$ is selected from hydrogen, halo, cyano, hydroxy, aryl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more $R^B$;

$R^B$ is halo, cyano, nitro, hydroxy or a group:

—$Y^3$—$X^3$—$Z^3$ wherein
  $Y^3$ is absent or a linker group of the formula —$[CR^{B1}R^{B2}]_n$— in which n is an integer selected from 1 or 2 and $R^{B1}$ and $R^{B2}$ are each independently selected from hydrogen or methyl;
  $X^3$ is absent or —O—, —C(O)—, —C(O)O—, —OC(O)—, —N($R^{B3}$)—, —N($R^{B4}$)—C(O), —N($R^{B4}$)—C(O)O—, —C(O)—N($R^{B3}$)—, —SO$_2$—, —S(O)$_2$N($R^{B3}$)—, or —N($R^{B4}$)SO$_2$— wherein $R^{B3}$ and $R^{B4}$ are each independently selected from hydrogen or methyl; and
  $Z^3$ is hydrogen, (1-6C)alkyl, aryl, heteroaryl or heterocyclyl;
  and wherein $Z^3$ is optionally further substituted by one or more substituent groups independently selected from oxo, halo, cyano, hydroxy, carboxy, $NR^{B5}R^{B6}$, (1-4C)alkoxy or (1-4C)alkyl; wherein $R^{B5}$ and $R^{B6}$ are each independently selected from hydrogen or (1-2C)alkyl;
  and wherein any alkyl group present in a substituent group on $Z^3$ is optionally further substituted by halo, hydroxy or $NR^{B7}R^{B8}$, wherein $R^{B7}$ and $R^{B8}$ are selected from hydrogen or (1-2C)alkyl;
  or $R^{B3}$ and $Z^3$ can be linked such that, together with the nitrogen atom to which they are attached, they form a 4-6 membered heterocyclic ring, which is optionally substituted by oxo, halo, hydroxy, $NR^{B5}R^{B6}$, (1-4C)alkoxy or (1-4C)alkyl;

(31) $R_3$ is selected from halo, cyano, hydroxy, aryl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more $R^B$;

$R^B$ is halo, cyano, nitro, hydroxy or a group:

—$Y^3$—$X^3$—$Z^3$ wherein
  $Y^3$ is absent or a linker group of the formula —$[CR^{B1}R^{B2}]_n$— in which n is an integer selected from 1 or 2 and $R^{B1}$ and $R^{B2}$ are each independently selected from hydrogen or methyl;
  $X^3$ is absent or —O—, —C(O)—, —C(O)O—, —OC(O)—, —N($R^{B3}$)—, —N($R^{B4}$)—C(O), —N($R^{B4}$)—C(O)O—, —C(O)—N($R^{B3}$)—, —SO$_2$—, —S(O)$_2$N($R^{B3}$)—, or —N($R^{B4}$)SO$_2$— wherein $R^{B3}$ and $R^{B4}$ are each independently selected from hydrogen or methyl; and
  $Z^3$ is hydrogen, (1-6C)alkyl, aryl, heteroaryl or heterocyclyl;
  and wherein $Z^3$ is optionally further substituted by one or more substituent groups independently selected from oxo, halo, cyano, hydroxy, carboxy, $NR^{B5}R^{B6}$, (1-4C)alkoxy or (1-4C)alkyl; wherein $R^{B5}$ and $R^{B6}$ are each independently selected from hydrogen or (1-2C)alkyl;
  and wherein any alkyl group present in a substituent group on $Z^3$ is optionally further substituted by halo, hydroxy or $NR^{B7}R^{B8}$, wherein $R^{B7}$ and $R^{B8}$ are selected from hydrogen or (1-2C)alkyl;
  or $R^{B3}$ and $Z^3$ can be linked such that, together with the nitrogen atom to which they are attached, they form a 4-6 membered heterocyclic ring, which is optionally substituted by oxo, halo, hydroxy, $NR^{B5}R^{B6}$, (1-4C)alkoxy or (1-4C)alkyl;

(32) $R_3$ is selected from hydrogen, halo, aryl, (3-8C)cycloalkyl, heteroaryl or heterocyclyl, wherein said aryl, (3-8C)cycloalkyl, heteroaryl or heterocyclyl is optionally substituted by one or more $R^B$;

$R^B$ is halo, cyano, nitro, hydroxy or a group:

—$Y^3$—$X^3$—$Z^3$ wherein
  $Y^3$ is absent or a linker group of the formula —$[CR^{B1}R^{B2}]_n$— in which n is an integer selected from 1 or 2 and $R^{B1}$ and $R^{B2}$ are each independently selected from hydrogen or methyl;
  $X^3$ is absent or —O—, —C(O)—, —C(O)O—, —OC(O)—, —N($R^{B3}$)—, —N($R^{B4}$)—C(O), —N($R^{B4}$)—C(O)O—, —C(O)—N($R^{B3}$)—, —SO$_2$—, —S(O)$_2$N($R^{B3}$)—, or —N($R^{B4}$)SO$_2$— wherein $R^{B3}$ and $R^{B4}$ are each independently selected from hydrogen or methyl; and
  $Z^3$ is hydrogen, (1-6C)alkyl, aryl, heteroaryl or heterocyclyl;

and wherein $Z^3$ is optionally further substituted by one or more substituent groups independently selected from oxo, halo, cyano, hydroxy, carboxy, $NR^{B5}R^{B6}$, (1-4C)alkoxy or (1-4C)alkyl;

(33) $R_3$ is selected halo, aryl, (3-8C)cycloalkyl, heteroaryl or heterocyclyl, wherein said aryl, (3-8C)cycloalkyl, heteroaryl or heterocyclyl is optionally substituted by one or more $R^B$;
$R^B$ is halo, cyano, nitro, hydroxy or a group:

—$Y^3$—$X^3$—$Z^3$ wherein
$Y^3$ is absent or a linker group of the formula —$[CR^{B1}R^{B2}]_n$— in which n is an integer selected from 1 or 2 and $R^{B1}$ and $R^{B2}$ are each independently selected from hydrogen or methyl;
$X^3$ is absent or —O—, —C(O)—, —C(O)O—, —OC(O)—, —N($R^{B3}$)—, —N($R^{B4}$)—C(O), —N($R^{B4}$)—C(O)O—, —C(O)—N($R^{B3}$)—, —$SO_2$—, —S(O)$_2$N($R^{B3}$)—, or —N($R^{B4}$)$SO_2$— wherein $R^{B3}$ and $R^{B4}$ are each independently selected from hydrogen or methyl; and
$Z^3$ is hydrogen, (1-6C)alkyl, aryl, heteroaryl or heterocyclyl;
and wherein $Z^3$ is optionally further substituted by one or more substituent groups independently selected from oxo, halo, cyano, hydroxy, carboxy, $NR^{B5}R^{B6}$, (1-4C)alkoxy or (1-4C)alkyl;

(34) $R_3$ is selected from hydrogen, halo, aryl, (3-8C)cycloalkyl, heteroaryl or heterocyclyl, wherein said aryl, (3-8C)cycloalkyl, heteroaryl or heterocyclyl is optionally substituted by one or more $R^B$;
$R^B$ is halo, cyano, nitro, hydroxy or a group:

—$Y^3$—$X^3$—$Z^3$ wherein
$Y^3$ is absent or a linker group of the formula —$[CR^{B1}R^{B2}]_n$— in which n is an integer selected from 1 or 2 and $R^{B1}$ and $R^{B2}$ are each independently selected from hydrogen or methyl;
$X^3$ is absent or —O—, —C(O)O—, —N($R^{B3}$)—, —N($R^{B4}$)—C(O), —C(O)—N($R^{B3}$)—, —$SO_2$— or —S(O)$_2$N($R^{B3}$)—, wherein $R^{B3}$ and $R^{B4}$ are each independently selected from hydrogen or methyl; and
$Z^3$ is hydrogen, (1-6C)alkyl, aryl, heteroaryl or heterocyclyl;
and wherein $Z^3$ is optionally further substituted by one or more substituent groups independently selected from oxo, halo, cyano, hydroxy, $NR^{B5}R^{B6}$, (1-4C)alkoxy or (1-4C)alkyl; wherein $R^{B5}$ and $R^{B6}$ are each independently selected from hydrogen or (1-2C)alkyl;

(35) $R_3$ is selected from halo, aryl, (3-8C)cycloalkyl, heteroaryl or heterocyclyl, wherein said aryl, (3-8C) cycloalkyl, heteroaryl or heterocyclyl is optionally substituted by one or more $R^B$;
$R^B$ is halo, cyano, nitro, hydroxy or a group:

—$Y^3$—$X^3$—$Z^3$ wherein
$Y^3$ is absent or a linker group of the formula —$[CR^{B1}R^{B2}]_n$— in which n is an integer selected from 1 or 2 and $R^{B1}$ and $R^{B2}$ are each independently selected from hydrogen or methyl;
$X^3$ is absent or —O—, —C(O)O—, —N($R^{B3}$)—, —N($R^{B4}$)—C(O), —C(O)—N($R^{B3}$)—, —$SO_2$— or —S(O)$_2$N($R^{B3}$)—, wherein $R^{B3}$ and $R^{B4}$ are each independently selected from hydrogen or methyl; and
$Z^3$ is hydrogen, (1-6C)alkyl, aryl, heteroaryl or heterocyclyl;
and wherein $Z^3$ is optionally further substituted by one or more substituent groups independently selected from oxo, halo, cyano, hydroxy, $NR^{B5}R^{B6}$, (1-4C)alkoxy or (1-4C)alkyl; wherein $R^{B5}$ and $R^{B6}$ are each independently selected from hydrogen or (1-2C)alkyl;

(36) $R_3$ is selected from hydrogen, halo, aryl, (3-8C)cycloalkyl, heteroaryl or heterocyclyl, wherein said aryl, (3-8C)cycloalkyl, heteroaryl or heterocyclyl is optionally substituted by one or more $R^B$;
$R^B$ is halo, cyano, nitro, or a group:

—$Y^3$—$X^3$—$Z^3$ wherein
$Y^3$ is absent or a linker group of the formula —$[CR^{B1}R^{B2}]_n$— in which n is 1 and $R^{B1}$ and $R^{B2}$ are hydrogen;
$X^3$ is absent or —O—, —C(O)O—, —N($R^{B3}$)—, —N($R^{B4}$)—C(O), —C(O)—N($R^{B3}$)—, —$SO_2$— or —S(O)$_2$N($R^{B3}$)—, wherein $R^{B3}$ and $R^{B4}$ are each independently selected from hydrogen or methyl; and
$Z^3$ is hydrogen, (1-6C)alkyl, aryl, heteroaryl or heterocyclyl;
and wherein $Z^3$ is optionally further substituted by one or more substituent groups independently selected from oxo, halo or (1-4C)alkyl;

(37) $R_3$ is selected from halo, aryl, (3-8C)cycloalkyl, heteroaryl or heterocyclyl, wherein said aryl, (3-8C) cycloalkyl, heteroaryl or heterocyclyl is optionally substituted by one or more $R^B$;
$R^B$ is halo, cyano, nitro, or a group:

—$Y^3$—$X^3$—$Z^3$ wherein
$Y^3$ is absent or a linker group of the formula —$[CR^{B1}R^{B2}]_n$— in which n is 1 and $R^{B1}$ and $R^{B2}$ are hydrogen;
$X^3$ is absent or —O—, —C(O)O—, —N($R^{B3}$)—, —N($R^{B4}$)—C(O), —C(O)—N($R^{B3}$)—, —$SO_2$— or —S(O)$_2$N($R^{B3}$)—, wherein $R^{B3}$ and $R^{B4}$ are each independently selected from hydrogen or methyl; and
$Z^3$ is hydrogen, (1-6C)alkyl, aryl, heteroaryl or heterocyclyl;
and wherein $Z^3$ is optionally further substituted by one or more substituent groups independently selected from oxo, halo or (1-4C)alkyl;

(38) $R_4$ is selected from hydrogen, halo, cyano, nitro, hydroxy or a group

—$Y^4$—$X^4$—$Z^4$ wherein
$Y^4$ is absent or a linker group of the formula —$[CR^{4A}R^{4B}]_p$— in which p is an integer selected from 1 or 2, and $R^{4A}$ and $R^{4B}$ are each independently selected from hydrogen or (1-2C)alkyl;
$X^4$ is absent or —O—, —C(O)—, —C(O)O—, —OC(O)—, —CH(O$R^{4C}$)—, —N($R^{4C}$)—, —N($R^{4D}$)—C(O)—, —N($R^{4D}$)—C(O)O—, —C(O)—N($R^{4C}$)—, —$SO_2$—, —S(O)$_2$N ($R^{4C}$)—, or —N($R^{4D}$)SO$_2$— wherein $R^{4C}$ and $R^{4D}$ are each independently selected from hydrogen or methyl; and $Z^4$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^4$ is optionally further substituted by one or more substituent groups independently selected from oxo, halo, cyano, nitro, hydroxy, carboxy, NR$^{4E}$R$^{4F}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{4E}$R$^{4F}$, NR$^{4E}$C(O)R$^{4F}$, NR$^{4E}$S(O)$_2$R$^{4F}$ and S(O)$_2$NR$^{4E}$R$^{4F}$; wherein R$^{4E}$ and R$^{4F}$ are each independently selected from hydrogen, (1-4C)alkyl or R$^{4E}$ and R$^{4F}$ can be linked such that, together with the nitrogen atom to which they are attached, they form a 4-6 membered heterocyclic ring;

and wherein any alkyl, aryl, heterocyclyl or heteroaryl group present in a substituent group on $Z^4$ is optionally further substituted by halo, cyano, nitro, hydroxy, caboxy, NR$^{4G}$R$^{4H}$, (1-2C)alkoxy, or (1-2C)alkyl; wherein R$^{4G}$ and R$^{4H}$ are selected from hydrogen or (1-2C)alkyl;

or R$^{4C}$ and Z$^4$ can be linked such that, together with the nitrogen atom to which they are attached, they form a 4-7 membered heterocyclic ring, which is optionally substituted by oxo, halo, cyano, nitro, hydroxy, carboxy, NR$^{4E}$R$^{4F}$, (1-4C)alkyl, (3-8C)cycloalkyl, C(O)NR$^{4E}$R$^{4F}$ or NR$^{4E}$C(O)R$^{4F}$;

with the proviso that R$_4$ is only a group containing four or more non-hydrogen atoms when R$_3$ is a group comprising four or less non-hydrogen atoms;

(39) R$_4$ is selected from hydrogen, halo, cyano, nitro, hydroxy or a group

—Y$^4$—X$^4$—Z$^4$ wherein

Y$^4$ is absent or a linker group of the formula —[CR$^{4A}$R$^{4B}$]$_p$— in which p is an integer selected from 1 or 2, and R$^{4A}$ and R$^{4B}$ are each independently selected from hydrogen or (1-2C)alkyl;

X$^4$ is absent or —C(O)—, —C(O)O, —OC(O)—, —N(R$^{4D}$)—C(O)—, —C(O)—N(R$^{4C}$), —SO$_2$—, —S(O)$_2$N(R$^{4C}$)—, or —N(R$^{4D}$)SO$_2$— wherein R$^{4C}$ and R$^{4D}$ are each independently selected from hydrogen or methyl; and Z$^4$ is hydrogen, (1-6C)alkyl, aryl, (3-6C)cycloalkyl, (3-6C)cycloalkenyl, heteroaryl or heterocyclyl;

and wherein Z$^4$ is optionally further substituted by one or more substituent groups independently selected from oxo, halo, cyano, nitro, hydroxy, carboxy, NR$^{4E}$R$^{4F}$, (1-4C)alkoxy, (1-4C)alkyl, (3-8C)cycloalkyl, aryl, heterocyclyl, heteroaryl, C(O)NR$^{4E}$R$^{4F}$ or NR$^{4E}$C(O)R$^{4F}$; wherein R$^{4E}$ and R$^{4F}$ are each independently selected from hydrogen or (1-2C)alkyl;

and wherein any alkyl, aryl, heterocyclyl or heteroaryl group present in a substituent group on Z$^4$ is optionally further substituted by halo, cyano, nitro, hydroxy, caboxy, NR$^{4G}$R$^{4H}$, (1-2C)alkoxy, or (1-2C)alkyl; wherein R$^{4G}$ and R$^{4H}$ are selected from hydrogen or (1-2C)alkyl;

or R$^{4C}$ and Z$^4$ can be linked such that, together with the nitrogen atom to which they are attached, they form a 4-7 membered heterocyclic ring, which is optionally substituted by oxo, halo, cyano, nitro, hydroxy, carboxy, NR$^{4E}$R$^{4F}$, (1-4C)alkoxy or (1-4C)alkyl;

with the proviso that R$_4$ is only a group containing four or more non-hydrogen atoms when R$_3$ is a group comprising four or less non-hydrogen atoms;

(40) R$_4$ is selected from hydrogen, halo, cyano, nitro, hydroxy or a group

—Y$^4$—X$^4$—Z$^4$ wherein

Y$^4$ is absent or a linker group of the formula —[CR$^{4A}$R$^{4B}$]$_p$— in which p is an integer selected from 1 or 2, and R$^{4A}$ and R$^{4B}$ are each independently selected from hydrogen or (1-2C)alkyl;

X$^4$ is absent or —C(O)—, —C(O)O—, —OC(O)—, —N(R$^{4D}$)—C(O)—, —C(O)—N(R$^{4C}$), —SO$_2$—, —S(O)$_2$N(R$^{4C}$)—, or —N(R$^{4D}$)SO$_2$— wherein R$^{4C}$ and R$^{4D}$ are each independently selected from hydrogen or methyl; and Z$^4$ is hydrogen, (1-6C)alkyl, aryl, (3-6C)cycloalkyl, heteroaryl or heterocyclyl;

and wherein Z$^4$ is optionally further substituted by one or more substituent groups independently selected from oxo, halo, cyano, hydroxy, NR$^{4E}$R$^{4F}$, (1-4C)alkoxy, (1-4C)alkyl, aryl, heterocyclyl, heteroaryl, C(O)NR$^{4E}$R$^{4F}$ or NR$^{4E}$C(O)R$^{4F}$; wherein R$^{4E}$ and R$^{4F}$ are each independently selected from hydrogen or (1-2C)alkyl;

and wherein any alkyl, aryl, heterocyclyl or heteroaryl group present in a substituent group on Z$^4$ is optionally further substituted by halo, hydroxy, NR$^{4G}$R$^{4H}$, (1-2C)alkoxy, or (1-2C)alkyl; wherein R$^{4G}$ and R$^{4H}$ are selected from hydrogen or (1-2C)alkyl;

with the proviso that R$_4$ is only a group containing four or more non-hydrogen atoms when R$_3$ is a group comprising four or less non-hydrogen atoms;

(41) R$_4$ is selected from hydrogen, halo, cyano, nitro, hydroxy or a group

—Y$^4$—X$^4$—Z$^4$ wherein

Y$^4$ is absent or a linker group of the formula —[CR$^{4A}$R$^{4B}$]$_p$— in which p is an integer selected from 1 or 2, and R$^{4A}$ and R$^{4B}$ are each independently selected from hydrogen or (1-2C)alkyl;

X$^4$ is absent or —C(O)—, —C(O)O—, —OC(O)—, —N(R$^{4D}$)—C(O)— or —C(O)—N(R$^{4C}$), wherein R$^{4C}$ and R$^{4D}$ are each independently selected from hydrogen or methyl; and Z$^4$ is hydrogen, (1-4C)alkyl, phenyl, (3-6C)cycloalkyl, 5- or 6-membered heteroaryl or a 5- or 6-membered heterocyclyl;

and wherein Z$^4$ is optionally further substituted by one or more substituent groups independently selected from oxo, halo, cyano, hydroxy, NR$^{4E}$R$^{4F}$, (1-4C)alkoxy or (1-4C)alkyl; wherein $R^{4E}$ and $R^{4F}$ are each independently selected from hydrogen or (1-2C)alkyl;
with the proviso that $R_4$ is only a group containing four or more non-hydrogen atoms when $R_3$ is a group comprising four or less non-hydrogen atoms;

(42) $R_4$ is selected from hydrogen, halo, cyano, nitro, hydroxy or a group $$-X^4-Z^4$$

wherein
$X^4$ is absent or $-C(O)-$, $-C(O)O-$, $-OC(O)-$, $-N(R^{4D})-C(O)-$ or $-C(O)-N(R^{4C})$, wherein $R^{4C}$ and $R^{4D}$ are each independently selected from hydrogen or methyl; and
$Z^4$ is hydrogen, (1-4C)alkyl, phenyl, 5- or 6-membered heteroaryl or a 5- or 6-membered heterocyclyl;
and wherein $Z^4$ is optionally further substituted by one or more substituent groups independently selected from oxo, halo, cyano, hydroxy, $NR^{4E}R^{4F}$, (1-4C)alkoxy or (1-4C)alkyl; wherein $R^{4E}$ and $R^{4F}$ are each independently selected from hydrogen or methyl;
with the proviso that $R_4$ is only a group containing four or more non-hydrogen atoms when $R_3$ is a group comprising four or less non-hydrogen atoms;

(43) $R_4$ is selected from hydrogen, halo, cyano, nitro, hydroxy or a group $$-Z^4$$

wherein
$Z^4$ is (1-4C)alkyl, phenyl, 5- or 6-membered heteroaryl or a 5- or 6-membered heterocyclyl;
and wherein $Z^4$ is optionally further substituted by one or more substituent groups independently selected from oxo, halo, cyano, hydroxy, $NR^{4E}R^{4F}$, (1-4C)alkoxy or (1-4C)alkyl; wherein $R^{4E}$ and $R^{4F}$ are each independently selected from hydrogen or methyl;
with the proviso that $R_4$ is only a group containing four or more non-hydrogen atoms when $R_3$ is a group comprising four or less non-hydrogen atoms;

(44) $R_4$ is selected from hydrogen, halo, cyano, nitro, hydroxy or a group $$-Z^4$$

wherein
$Z^4$ is (1-4C)alkyl or phenyl;
and wherein $Z^4$ is optionally further substituted by one or more substituent groups independently selected from oxo, halo, hydroxy, or (1-4C)alkyl;
with the proviso that $R_4$ is only a group containing four or more non-hydrogen atoms when $R_3$ is a group comprising four or less non-hydrogen atoms;

(45) $R_4$ is selected from hydrogen, halo, cyano, nitro or hydroxy;

(46) $R_4$ is selected from hydrogen or halo;

(47) $R_4$ is hydrogen;

(48) $R_5$ is selected from hydrogen, halo, cyano, nitro, hydroxy or a group $$-Y^5-X^5-Z^5$$

wherein:
$Y^5$ is absent or a linker group of the formula $-[CR^{5A}R^{5B}]_q-$ in which q is an integer selected from 1 or 2 and $R^{5A}$ and $R^{5B}$ are each independently selected from hydrogen or methyl;
$X^5$ is absent or $-O-$, $-C(O)-$, $-C(O)O-$, $-OC(O)-$, $-N(R^{5C})-$, $-N(R^{5D})-C(O)$, $-N(R^{5D})-C(O)O-$, $-C(O)-N(R^{5C})-$, $-SO_2-$, $-S(O)_2N(R^{5C})-$, or $-N(R5^{4D})SO_2-$ wherein $R^{4C}$ and $R^{4D}$ are each independently selected from hydrogen or methyl; and
$Z^5$ is hydrogen or (1-4C)alkyl which is optionally further substituted by one or more substituent groups independently selected from oxo, halo, cyano, hydroxy, carboxy, $NR^{5E}R^{5F}$ or (1-2C)alkoxy; wherein $R^{5E}$ and $R^{5F}$ are each independently selected from hydrogen or (1-2C)alkyl;

(49) $R_5$ is selected from hydrogen, halo, cyano, nitro, hydroxy or a group $$-Y^5-X^5-Z^5$$

wherein:
$Y^5$ is absent or a linker group of the formula $-[CR^{5A}R^{5B}]_q-$ in which q is 1 and $R^{5A}$ and $R^{5B}$ are each independently selected from hydrogen or methyl;
$X^5$ is absent or $-O-$, $-C(O)-$, $-C(O)O-$, $-OC(O)-$, $-N(R^{5D})-C(O)$, $-C(O)-N(R^{5C})$, $-SO_2-$, $-S(O)_2N(R^{5C})-$, or $-N(R5^{4D})SO_2-$ wherein $R^{4C}$ and $R^{4D}$ are each independently selected from hydrogen or methyl; and
$Z^5$ is hydrogen or (1-4C)alkyl which is optionally further substituted by one or more substituent groups independently selected from oxo, halo, cyano, hydroxy, carboxy, $NR^{5E}R^{5F}$ or (1-2C)alkoxy; wherein $R^{5E}$ and $R^{5F}$ are each independently selected from hydrogen or methyl;

(50) $R_5$ is selected from hydrogen, halo, cyano, nitro, hydroxy or a group $$-Y^5-X^5-Z^5$$

wherein:
$Y^5$ is absent or a linker group of the formula $-[CR^{5A}R^{5B}]_q-$ in which q is 1 and $R^{5A}$ and $R^{5B}$ are each independently selected from hydrogen or methyl;
$X^5$ is absent or $-O-$, $-C(O)-$, $-C(O)O-$, $-OC(O)-$, $-N(R^{5D})-C(O)$, $-C(O)-N(R^{5C})$, wherein $R^{4C}$ and $R^{4D}$ are each independently selected from hydrogen or methyl; and
$Z^5$ is hydrogen or (1-4C)alkyl which is optionally further substituted by one or more substituent groups independently selected from oxo, halo, cyano, hydroxy, carboxy, $NR^{5E}R^{5F}$ or (1-2C)alkoxy; wherein $R^{5E}$ and $R^{5F}$ are each independently selected from hydrogen or methyl;

(51) $R_5$ is selected from hydrogen, halo, cyano, nitro, hydroxy or a group $$-X^5-Z^5$$

wherein:
$X^5$ is absent or $-O-$; and
$Z^5$ is (1-4C)alkyl which is optionally further substituted by one or more substituent groups independently selected from oxo, halo, cyano, hydroxy, carboxy, $NR^{5E}R^{5F}$ or (1-2C)alkoxy; wherein $R^{5E}$ and $R^{5F}$ are each independently selected from hydrogen or methyl;

(52) $R_5$ is selected from hydrogen, halo, (1-4C)alkyl, (1-2C)alkoxy, cyano or hydroxy;

(53) $R_5$ is selected from hydrogen, halo, (1-2C)alkyl or (1-2C)alkoxy;

(54) $R_5$ is selected from hydrogen or halo or (1-2C)alkoxy;

(55) $R_6$ is selected from hydrogen, halo, cyano, nitro, hydroxy or a group $$-Y^6-X^6-Z^6$$

wherein:
  $Y^6$ is absent or a linker group of the formula $-[CR^{6A}R^{6B}]_q-$ in which q is an integer selected from 1 or 2, and $R^{6A}$ and $R^{6B}$ are each independently selected from hydrogen or (1-2C)alkyl;
  $X^6$ is absent or $-O-$, $-C(O)-$, $-C(O)O-$, $-OC(O)-$, $-N(R^{6C})-$, $-N(R^{6D})-C(O)$, $-N(R^{6D})-C(O)O-$, $-C(O)-N(R^{6C})-$, $-S-$, $-SO-$, $-SO_2-$, $-S(O)_2N(R^{6C})-$, or $-N(R^{6D})SO_2-$ wherein $R^{6C}$ and $R^{6D}$ are each independently selected from hydrogen or methyl; and
  $Z^6$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
    and wherein $Z^6$ is optionally further substituted by one or more substituent groups independently selected from oxo, halo, cyano, nitro, hydroxy, carboxy, $NR^{6E}R^{6F}$, (1-4C)alkoxy, (1-4C)alkyl, (3-8C)cycloalkyl, (3-8C)cycloalkyl-(1-3C)alkyl, aryl, aryl-(1-2C)alkyl, heterocyclyl, heterocyclyloxy, heterocyclyl-(1-2C)alkyl, heteroaryl, heteroaryl-(1-2C)alkyl, $C(O)NR^{6E}R^{6F}$, $NR^{6E}C(O)R^{6F}$, $NR^{6E}S(O)_2R^{6F}$ and $S(O)_2NR^{6E}R^{6F}$; wherein $R^{6E}$ and $R^{6F}$ are each independently selected from hydrogen or (1-4C)alkyl; or $R^{6E}$ and $R^{6F}$ can be linked such that, together with the nitrogen atom to which they are attached, they form a 4-6 membered heterocyclic ring;
    and wherein any alkyl, aryl, heterocyclyl or heteroaryl group present in a substituent group on $Z^6$ is optionally further substituted by halo, cyano, nitro, hydroxy, caboxy, $NR^{6G}R^{6H}$ (1-2C)alkoxy, or (1-2C)alkyl; wherein $R^{6G}$ and $R^{6H}$ are selected from hydrogen or (1-2C)alkyl;
    or $R^{6C}$ and $Z^6$ can be linked such that, together with the nitrogen atom to which they are attached, they form a 4-6 membered heterocyclic ring, which is optionally substituted by oxo, halo, cyano, nitro, hydroxy, carboxy, $NR^{6E}R^{6F}$, (1-4C)alkoxy, (1-4C)alkyl, (3-8C)cycloalkyl, or $C(O)NR^{6E}R^{6F}$, $NR^{6E}C(O)R^{6F}$, $NR^{6E}S(O)_2R^{6F}$ and $S(O)_2NR^{6E}R^{6F}$;

(56) $R_6$ is selected from hydrogen, halo, cyano, nitro, hydroxy or a group $$-Y^6-X^6-Z^6$$

wherein:
  $Y^6$ is absent or a linker group of the formula $-[CR^{6A}R^{6B}]_q-$ in which q is an integer selected from 1 or 2, and $R^{6A}$ and $R^{6B}$ are each independently selected from hydrogen or (1-2C)alkyl;
  $X^6$ is absent or $-O-$, $-C(O)-$, $-C(O)O-$, $-OC(O)-$, $-N(R^{6C})-$, $-N(R^{6D})-C(O)$, $-N(R^{6D})-C(O)O-$, $-C(O)-N(R^{6C})-$, $-S-$, $-SO-$, $-SO_2-$, $-S(O)_2N(R^{6C})-$, or $-N(R^{6D})SO_2-$ wherein $R^{6C}$ and $R^{6D}$ are each independently selected from hydrogen or methyl; and
  $Z^6$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
    and wherein $Z^6$ is optionally further substituted by one or more substituent groups independently selected from oxo, halo, cyano, nitro, hydroxy, carboxy, $NR^{6E}R^{6F}$, (1-4C)alkoxy, (1-4C)alkyl, (3-8C)cycloalkyl, aryl, heterocyclyl, heteroaryl, $C(O)NR^{6E}R^{6F}$ or $NR^{6E}C(O)R^{6F}$; wherein $R^{6E}$ and $R^{6F}$ are each independently selected from hydrogen or (1-2C)alkyl; or $R^{6E}$ and $R^{6F}$ can be linked such that, together with the nitrogen atom to which they are attached, they form a 4-6 membered heterocyclic ring;
    and wherein any alkyl, aryl, heterocyclyl or heteroaryl group present in a substituent group on $Z^6$ is optionally further substituted by halo, cyano, nitro, hydroxy, caboxy, $NR^{6G}R^{6H}$ (1-2C)alkoxy, or (1-2C)alkyl; wherein $R^{6G}$ and $R^{6H}$ are selected from hydrogen or (1-2C)alkyl;

(57) $R_6$ is selected from hydrogen, halo, cyano, nitro, hydroxy or a group $$-Y^6-X^6-Z^6$$

wherein:
  $Y^6$ is absent or a linker group of the formula $-[CR^{6A}R^{6B}]_q-$ in which q is an integer selected from 1 or 2, and $R^{6A}$ and $R^{6B}$ are each independently selected from hydrogen or (1-2C)alkyl;
  $X^6$ is absent or $-O-$, $-C(O)-$, $-C(O)O-$, $-OC(O)-$, $-N(R^{6D})-C(O)$, $-N(R^{6D})-C(O)O-$, $-C(O)-N(R^{6C})-$, $-SO_2-$, $-S(O)_2N(R^{6C})-$, or $-N(R^{6D})SO_2-$ wherein $R^{6C}$ and $R^{6D}$ are each independently selected from hydrogen or methyl; and
  $Z^6$ is hydrogen, (1-6C)alkyl, aryl, (3-6C)cycloalkyl, (3-6C)cycloalkenyl, heteroaryl or heterocyclyl;
    and wherein $Z^6$ is optionally further substituted by one or more substituent groups independently selected from oxo, halo, cyano, nitro, hydroxy, carboxy, $NR^{6E}R^{6F}$, (1-4C)alkoxy, (1-4C)alkyl, wherein $R^{6E}$ and $R^{6F}$ are each independently selected from hydrogen or (1-2C)alkyl;
    and wherein any alkyl group present in a substituent group on $Z^6$ is optionally further substituted by halo, hydroxy, $NR^{6G}R^{6H}$ (1-2C)alkoxy, or (1-2C)alkyl; wherein $R^{6G}$ and $R^{6H}$ are selected from hydrogen or (1-2C)alkyl;

(58) $R_6$ is selected from hydrogen, halo, cyano, nitro, hydroxy or a group $$-Y^6-X^6-Z^6$$

wherein:
  $Y^6$ is absent or a linker group of the formula $-[CR^{6A}R^{6B}]_q-$ in which q is an integer selected from 1 or 2, and $R^{6A}$ and $R^{6B}$ are each independently selected from hydrogen or (1-2C)alkyl;
  $X^6$ is absent or $-O-$, $-C(O)-$, $-C(O)O-$, $-OC(O)-$, $-N(R^{6D})-C(O)$ or $-C(O)-N(R^{6C})-$, wherein $R^{6C}$ and $R^{6D}$ are each independently selected from hydrogen or methyl; and
  $Z^6$ is hydrogen, (1-6C)alkyl, aryl, (3-6C)cycloalkyl, (3-6C)cycloalkenyl, heteroaryl or heterocyclyl;

and wherein $Z^6$ is optionally further substituted by one or more substituent groups independently selected from oxo, halo, cyano, nitro, hydroxy, $NR^{6E}R^{6F}$, (1-2C)alkoxy, (1-2C)alkyl, wherein $R^{6E}$ and $R^{6F}$ are each independently selected from hydrogen or methyl;

(59) $R_6$ is selected from hydrogen, halo, cyano, nitro, hydroxy or a group $$-X^6-Z^6$$

wherein:
$X^6$ is absent or —O—, —C(O)—, —C(O)O—, —OC(O)—, —N($R^{6D}$)—C(O) or —C(O)—N($R^{6C}$), wherein $R^{6C}$ and $R^{6D}$ are each independently selected from hydrogen or methyl; and
$Z^6$ is hydrogen, (1-6C)alkyl, aryl, heteroaryl or heterocyclyl;
and wherein $Z^6$ is optionally further substituted by one or more substituent groups independently selected from oxo, halo, cyano, hydroxy, $NR^{6E}R^{6F}$, (1-2C)alkoxy, (1-2C)alkyl, wherein $R^{6E}$ and $R^{6F}$ are each independently selected from hydrogen or methyl;

(60) $R_6$ is selected from hydrogen, halo, cyano, nitro, hydroxy or a group $$-X^6-Z^6$$

wherein:
$X^6$ is absent or —O—; and
$Z^6$ is (1-6C)alkyl, phenyl, 5- or 6-membered heteroaryl or a 5- or 6-membered heterocyclyl;
and wherein $Z^6$ is optionally further substituted by one or more substituent groups independently selected from oxo, halo, cyano, nitro, hydroxy, $NR^{6E}R^{6F}$, (1-2C)alkoxy, (1-2C)alkyl, wherein $R^{6E}$ and $R^{6F}$ are each independently selected from hydrogen or methyl;

(61) $R_6$ is selected from hydrogen, halo, cyano, nitro, hydroxy or a group $$-X^6-Z^6$$

wherein:
$X^6$ is absent or —O—; and
$Z^6$ is (1-4C)alkyl or phenyl;
and wherein $Z^6$ is optionally further substituted by one or more substituent groups independently selected from oxo, halo, or (1-2C)alkyl;

(62) $R_6$ is selected from hydrogen, halo, cyano, nitro, hydroxy, (1-4C)alkyl, (1-4C)alkoxy or OPh;

(63) $R_6$ is selected from hydrogen, halo, (1-2C)alkyl, (1-2C)alkoxy or OPh;

(64) $R_7$ is selected from hydrogen, halo, cyano, nitro, hydroxy or a group $$-Y^7-X^7-Z^7$$

wherein:
$Y^7$ is absent or a linker group of the formula —[$CR^{7A}R^{7B}$]$_q$— in which q is an integer selected from 1, 2 or 3, and $R^{7A}$ and $R^{7B}$ are each independently selected from hydrogen or (1-2C)alkyl;
$X^7$ is absent or —O—, —C(O)—, —C(O)O—, —OC(O)—, —N($R^{7C}$)—, —N($R^{7D}$)—C(O), —N($R^{7D}$)—C(O)O—, —C(O)—N($R^{7C}$)—, —S—, —SO—, —SO$_2$—, —S(O)$_2$N($R^{7C}$)—, or —N($R^{7D}$)SO$_2$— wherein $R^{7C}$ and $R^{7D}$ are each independently selected from hydrogen or methyl; and
$Z^7$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein $Z^7$ is optionally further substituted by one or more substituent groups independently selected from oxo, halo, cyano, nitro, hydroxy, carboxy, $NR^{7E}R^{7F}$, (1-4C)alkoxy, (1-4C)alkyl, (3-8C)cycloalkyl, (3-8C)cycloalkyl-(1-3C)alkyl, aryl, aryl-(1-2C)alkyl, heterocyclyl, =heterocyclyl-(1-2C)alkyl, heteroaryl, heteroaryl-(1-2C)alkyl, C(O)NR$^{7E}$R$^{7F}$, NR$^{7E}$C(O)R$^{7F}$, NR$^{7E}$S(O)$_2$R$^{7F}$ and S(O)$_2$NR$^{7E}$R$^{7F}$; wherein $R^{7E}$ and $R^{7F}$ are each independently selected from hydrogen or (1-4C)alkyl; or $R^{7E}$ and $R^{7F}$ can be linked such that, together with the nitrogen atom to which they are attached, they form a 4-7 membered heterocyclic ring;
and wherein any alkyl, aryl, heterocyclyl or heteroaryl group present in a substituent group on $Z^7$ is optionally further substituted by halo, cyano, nitro, hydroxy, caboxy, NR$^{7G}$R$^{7H}$, (1-2C)alkoxy, or (1-2C)alkyl; wherein $R^{7G}$ and $R^{7H}$ are selected from hydrogen or (1-2C)alkyl;
or $R^{7C}$ and $Z^7$ can be linked such that, together with the nitrogen atom to which they are attached, they form a 4-7 membered heterocyclic ring, which is optionally substituted by oxo, halo, cyano, nitro, hydroxy, carboxy, NR$^{7E}$R$^{7F}$, (1-4C)alkoxy or (1-4C)alkyl;

(65) $R_7$ is selected from hydrogen, halo, cyano, nitro, hydroxy or a group $$-Y^7-X^7-Z^7$$

wherein:
$Y^7$ is absent or a linker group of the formula —[$CR^{7A}R^{7B}$]$_q$— in which q is an integer selected from 1, 2 or 3, and $R^{7A}$ and $R^{7B}$ are each independently selected from hydrogen or (1-2C)alkyl;
$X^7$ is absent or —O—, —C(O)—, —C(O)O—, —OC(O)—, —N($R^{7C}$)—, —N($R^{7D}$)—C(O)—, —C(O)—N($R^{7C}$)—, —SO$_2$—, —S(O)$_2$N($R^{7C}$)—, or —N($R^{7D}$)SO$_2$— wherein $R^{7C}$ and $R^{7D}$ are each independently selected from hydrogen or methyl; and
$Z^7$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein $Z^7$ is optionally further substituted by one or more substituent groups independently selected from oxo, halo, cyano, nitro, hydroxy, carboxy, NR$^{7E}$R$^{7F}$, (1-4C)alkoxy, (1-4C)alkyl, (3-8C)cycloalkyl, aryl, heterocyclyl, heteroaryl, C(O)NR$^{7E}$R$^{7F}$ or NR$^{7E}$C(O)R$^{7F}$; wherein $R^{7E}$ and $R^{7F}$ are each independently selected from hydrogen or (1-4C)alkyl; or $R^{7E}$ and $R^{7F}$ can be linked such that, together with the nitrogen atom to which they are attached, they form a 4-6 membered heterocyclic ring;
and wherein any alkyl, aryl, heterocyclyl or heteroaryl group present in a substituent group on $Z^7$ is optionally further substituted by halo, cyano, nitro, hydroxy, caboxy, NR$^{7G}$R$^{7H}$, (1-2C)alkoxy, or (1-2C)alkyl; wherein $R^{7G}$ and $R^{7H}$ are selected from hydrogen or (1-2C)alkyl;

(66) $R_7$ is selected from hydrogen, halo, cyano, nitro, hydroxy or a group $$-Y^7-X^7-Z^7$$

wherein:
Y$^7$ is absent or a linker group of the formula —[CR$^{7A}$R$^{7B}$]$_q$— in which q is an integer selected from 1, 2 or 3, and R$^{7A}$ and R$^{7B}$ are each independently selected from hydrogen or (1-2C)alkyl;
X$^7$ is absent or —O—, —C(O)—, —C(O)O—, —OC(O)—, —N(R$^{7C}$)—, —N(R$^{7D}$)—C(O), —C(O)—N(R$^{7C}$)—, —SO$_2$— or —S(O)$_2$N(R$^{7C}$)—, wherein R$^{7C}$ and R$^{7D}$ are each independently selected from hydrogen or methyl; and
Z$^7$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^7$ is optionally further substituted by one or more substituent groups independently selected from oxo, halo, cyano, hydroxy, carboxy, NR$^{7E}$R$^{7F}$, (1-4C)alkoxy, (1-4C)alkyl, (3-8C)cycloalkyl, aryl, heterocyclyl, heteroaryl, C(O)NR$^{7E}$R$^{7F}$ or NR$^{7E}$C(O)R$^{7F}$; wherein R$^{7E}$ and R$^{7F}$ are each independently selected from hydrogen or (1-4C)alkyl; or R$^{7E}$ and R$^{7F}$ can be linked such that, together with the nitrogen atom to which they are attached, they form a 4-6 membered heterocyclic ring;
and wherein any alkyl, aryl, heterocyclyl or heteroaryl group present in a substituent group on Z$^7$ is optionally further substituted by halo, cyano, nitro, hydroxy, caboxy, NR$^{7G}$R$^{7H}$, (1-2C)alkoxy, or (1-2C)alkyl; wherein R$^{7G}$ and R$^{7H}$ are selected from hydrogen or (1-2C)alkyl;

(67) R$_7$ is selected from hydrogen, halo, cyano, nitro, hydroxy or a group

—Y$^7$—X$^7$—Z$^7$ wherein:
Y$^7$ is absent or a linker group of the formula —[CR$^{7A}$R$^{7B}$]$_q$— in which q is an integer selected from 1, 2 or 3, and R$^{7A}$ and R$^{7B}$ are each independently selected from hydrogen or (1-2C)alkyl;
X$^7$ is absent or —O—, —C(O)—, —C(O)O—, —OC(O)—, —N(R$^{7D}$)—C(O)—, —C(O)—N(R$^{7C}$)—, wherein R$^{7C}$ and R$^{7D}$ are each independently selected from hydrogen or methyl; and
Z$^7$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^7$ is optionally further substituted by one or more substituent groups independently selected from oxo, halo, cyano, nitro, hydroxy, carboxy, NR$^{7E}$R$^{7F}$, (1-4C)alkoxy, (1-4C)alkyl, C(O)NR$^{7E}$R$^{7F}$ or NR$^{7E}$C(O)R$^{7F}$; wherein R$^{7E}$ and R$^{7F}$ are each independently selected from hydrogen or (1-4C)alkyl;
and wherein any alkyl group present in a substituent group on Z$^7$ is optionally further substituted by halo, cyano, hydroxy, NR$^{7G}$R$^{7H}$, (1-2C)alkoxy, or (1-2C)alkyl; wherein R$^{7G}$ and R$^{7H}$ are selected from hydrogen or (1-2C)alkyl;

(68) R$_7$ is selected from hydrogen, halo, cyano, nitro, hydroxy or a group

—Y$^7$—X$^7$—Z$^7$ wherein:
Y$^7$ is absent or a linker group of the formula —[CR$^{7A}$R$^{7B}$]$_q$— in which q is an integer selected from 1 or 2, and R$^{7A}$ and R$^{7B}$ are each independently selected from hydrogen or (1-2C)alkyl;
X$^7$ is absent or —O—; and Z$^7$ is hydrogen, (1-6C)alkyl, aryl, (3-6C)cycloalkyl, (3-6C)cycloalkenyl, heteroaryl or heterocyclyl;
and wherein Z$^7$ is optionally further substituted by one or more substituent groups independently selected from oxo, halo, cyano, nitro, hydroxy, carboxy, NR$^{7E}$R$^{7F}$, (1-4C)alkoxy or (1-4C)alkyl; wherein R$^{7E}$ and R$^{7F}$ are each independently selected from hydrogen or (1-2C)alkyl;

(69) R$_7$ is selected from hydrogen, halo, cyano, hydroxy or a group

—Y$^7$—X$^7$—Z$^7$ wherein:
Y$^7$ is absent or a linker group of the formula —[CR$^{7A}$R$^{7B}$]$_q$— in which q is an integer selected from 1 or 2, and R$^{7A}$ and R$^{7B}$ are each independently selected from hydrogen or (1-2C)alkyl;
X$^7$ is absent or —O—; and
Z$^7$ is hydrogen, (1-6C)alkyl, aryl, (3-6C)cycloalkyl, (3-6C)cycloalkenyl, heteroaryl or heterocyclyl;
and wherein Z$^7$ is optionally further substituted by one or more substituent groups independently selected from oxo, halo, cyano, nitro, hydroxy, carboxy, NR$^{7E}$R$^{7F}$, (1-4C)alkoxy or (1-4C)alkyl; wherein R$^{7E}$ and R$^{7F}$ are each independently selected from hydrogen or (1-2C)alkyl;

(70) R$_7$ is selected from hydrogen, halo, cyano, nitro, hydroxy or a group

—Y$^7$—X$^7$—Z$^7$ wherein:
Y$^7$ is absent or a linker group of the formula —[CR$^{7A}$R$^{7B}$]$_q$— in which q is an integer selected from 1 or 2, and R$^{7A}$ and R$^{7B}$ are each independently selected from hydrogen or (1-2C)alkyl;
X$^7$ is absent or —O—; and
Z$^7$ is hydrogen, (1-6C)alkyl, aryl, (3-6C)cycloalkyl, (3-6C)cycloalkenyl, 5- or 6-membered heteroaryl or a 5- or 6-membered heterocyclyl;
and wherein Z$^7$ is optionally further substituted by one or more substituent groups independently selected from oxo, halo, cyano, hydroxy, NR$^{7E}$R$^{7F}$, (1-2C)alkoxy or (1-2C)alkyl; wherein R$^{7E}$ and R$^{7F}$ are each independently selected from hydrogen or methyl;

(71) R$_7$ is selected from hydrogen, halo, cyano, hydroxy or a group

—Y$^7$—X$^7$—Z$^7$ wherein:
Y$^7$ is absent or a linker group of the formula —[CR$^{7A}$R$^{7B}$]$_q$— in which q is an integer selected from 1 or 2, and R$^{7A}$ and R$^{7B}$ are each independently selected from hydrogen or (1-2C)alkyl;
X$^7$ is absent or —O—; and
Z$^7$ is hydrogen, (1-6C)alkyl, aryl, (3-6C)cycloalkyl, (3-6C)cycloalkenyl, 5- or 6-membered heteroaryl or a 5- or 6-membered heterocyclyl;
and wherein Z$^7$ is optionally further substituted by one or more substituent groups independently selected from oxo, halo, cyano, hydroxy, NR$^{7E}$R$^{7F}$, (1-2C)alkoxy or (1-2C)alkyl; wherein R$^{7E}$ and R$^{7F}$ are each independently selected from hydrogen or methyl

(72) R$_7$ is selected from hydrogen, halo, cyano, nitro, hydroxy or a group

—Y$^7$—X$^7$—Z$^7$ wherein:
  $Y^7$ is absent or a linker group of the formula —$[CR^{7A}R^{7B}]_q$— in which q is an integer selected from 1 or 2, and $R^{7A}$ and $R^{7B}$ are each independently selected from hydrogen or methyl;
  $X^7$ is absent or —O—; and
  $Z^7$ is hydrogen, (1-6C)alkyl, aryl, (3-6C)cycloalkyl; and wherein $Z^7$ is optionally further substituted by one or more substituent groups independently selected from oxo, halo, hydroxy, N (1-2C)alkoxy or (1-2C)alkyl;

(73) $R_7$ is selected from hydrogen, halo, cyano, hydroxy or a group

—$Y^7$—$X^7$—$Z^7$ wherein:
  $Y^7$ is absent or a linker group of the formula —$[CR^{7A}R^{7B}]_q$— in which q is an integer selected from 1 or 2, and $R^{7A}$ and $R^{7B}$ are each independently selected from hydrogen or methyl;
  $X^7$ is absent or —O—; and
  $Z^7$ is hydrogen, (1-6C)alkyl, aryl, (3-6C)cycloalkyl; and wherein $Z^7$ is optionally further substituted by one or more substituent groups independently selected from oxo, halo, hydroxy, N (1-2C)alkoxy or (1-2C)alkyl;

(74) $R_7$ is selected from hydrogen, halo, cyano or a group

—$Y^7$—$X^7$—$Z^7$ wherein:
  $Y^7$ is absent or a linker group of the formula —$[CR^{7A}R^{7B}]_q$— in which q is an integer selected from 1 or 2, and $R^{7A}$ and $R^{7B}$ are each independently selected from hydrogen or methyl;
  $X^7$ is absent or —O—; and
  $Z^7$ is hydrogen, (1-6C)alkyl, phenyl, (3-6C)cycloalkyl; and wherein $Z^7$ is optionally further substituted by one or more substituent groups independently selected from halo, hydroxy or (1-2C)alkyl;

(75) $R_7$ is selected from halo, cyano or a group

—$Y^7$—$X^7$—$Z^7$ wherein:
  $Y^7$ is absent or a linker group of the formula —$[CR^{7A}R^{7B}]_q$— in which q is an integer selected from 1 or 2, and $R^{7A}$ and $R^{7B}$ are each independently selected from hydrogen or methyl;
  $X^7$ is absent or —O—; and
  $Z^7$ is hydrogen, (1-6C)alkyl, phenyl, (3-6C)cycloalkyl; and wherein $Z^7$ is optionally further substituted by one or more substituent groups independently selected from halo, hydroxy or (1-2C)alkyl;

(76) $R_7$ is selected from halo, (1-6C)alkyl, (1-2C)alkoxy or cyclopropyl.

In certain embodiments of the present invention, i.e. when $A_1$ to $A_4$ are carbon, one or more of the following provisos may apply:
  i) when $R_2$ is $CO_2H$ or C(O)OEt and $R_6$ is hydrogen, $R_7$ is not $NO_2$, $NH_2$, N(H)$CH_3$ or NHC(O)OC($CH_3$)$_3$;
  ii) when $R_2$ is —C(O)N$R_{2B}R_{2C}$, $R_1$ is hydrogen and one of $R_{2B}$ or $R_{2C}$ is hydrogen, the other of $R_{2b}$ or $R_{2C}$ is not pyrrolidin-3-yl, piperidin-3-yl, piperadin-4-yl, 1-methylpyrrolidin-3-yl, 1-methylpiperidin-3-yl, 1-benzylpyrrolindin-3-yl, azepan-3-yl, azetidin-3-yl or 1-methylazetidin-3-yl;
  iii) when $R_3$ is phenyl, $R_4$, $R_6$ and $R_7$ are hydrogen and $R_2$ is $CO_2H$ or C(O)OEt, $R_5$ is not F, Cl, Br, $CH_3$ or $OCH_3$;
  iv) $R_4$, $R_5$, $R_6$ and $R_7$ are all hydrogen only when $R_3$ is phenyl and $R_2$ is $CO_2H$;
  v) when $R_1$, $R_3$, $R_5$ and $R_7$ are hydrogen and $R_4$ and $R_6$ are chloro, $R_2$ is not C(O)OEt, COOH, $CONH_2$, tetrazole, $CONHNH_2$ or 2-amidotetrazole;
  vi) when $R_3$ is a phenyl substituted or a phenyl substituted with one or more groups selected from $OCH_3$, C, F, $CF_3$ or $CH_3$, and $R_4$ and $R_7$ are hydrogen, $R_5$ is not OMe, Cl or F when $R_6$ is hydrogen, nor is $R_5$ OMe when $R_6$ is OMe;
  vii) when $R_3$ is hydrogen or methyl, $R_7$ is not —N($R^{7D}$)$SO_2$—$Z^7$, wherein $Z^7$ is selected group methyl or a substituted or unsubstituted aryl or heteroaryl;
  viii) when $R_1$, $R_3$, $R_6$ and $R_7$ are hydrogen and $R_2$ is COOH or C(O)OMe, $R_4$ and $R_5$ are not methyl.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5-, 6- or 7-membered heterocyclyl ring comprising one, two or three heteroatoms selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably an aryl group is phenyl.

Suitably, $A_1$, $A_2$, $A_3$ and $A_4$ are as defined in paragraphs (1) to (3) above. In an embodiment, $A_1$, $A_2$, $A_3$ and $A_4$ as defined in paragraph (3).

Suitably, $R_1$ is as defined in any one of paragraphs (4) to (13) above. More suitably, $R_1$ is as defined in any one of paragraphs (11) to (13). Most suitably, $R_1$ is H.

Suitably, $R_2$ is as defined in any one of paragraphs (14) to (26) above. More suitably, $R_2$ is as defined in any one of paragraphs (19) to (26). Most suitably, $R_2$ is C(O)OH.

Suitably, $R_3$ is as defined in any one of paragraphs (27) to (37) above. More suitably, $R_3$ is as defined in any one of paragraphs (32) to (37). Most suitably, $R_3$ is as defined in paragraph (37).

Suitably, $R_4$ is as defined in any one of paragraphs (38) to (47) above. More suitably, $R_4$ is as defined in any one of paragraphs (44) to (47). Most suitably, $R_4$ is hydrogen.

Suitably, $R_5$ is as defined in any one of paragraphs (48) to (54) above. More suitably, $R_5$ is as defined in any one of paragraphs (51) to (54). Most suitably, $R_5$ is as defined in paragraph (54).

Suitably, $R_6$ is as defined in any one of paragraphs (55) to (63) above. More suitably $R_6$ is as defined in any one of paragraphs (61) to (63). Most suitably, $R_6$ is as defined in paragraph (63).

Suitably, $R_7$ is as defined in any one of paragraphs (64) to (76) above. More suitably, $R_7$ is as defined in any one of paragraphs (72) to (76). Most suitably, $R_7$ is as defined in paragraph (76).

In a particular group of compounds of the invention, $R_1$ is H, i.e. the compounds have the structural formula Ia (a sub-definition of formula I) shown below:

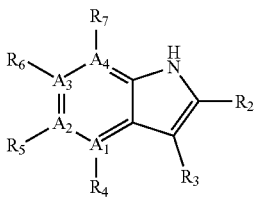

wherein $A_1, A_2, A_3, A_4, R_2, R_3, R_4, R_5, R_6$ and $R_7$ each have any one of the meanings defined herein; or a pharmaceutically acceptable salt, hydrate and/or solvate thereof.

In an embodiment of the compounds of formula Ia:
$A_1, A_2, A_3$ and $A_4$ are as defined in any one of paragraphs (1) to (3) above;
$R_2$ is as defined in any one of paragraphs (14) to (26) above;
$R_3$ is as defined in any one of paragraphs (27) to (37) above;
$R_4$ is as defined in any one of paragraphs (38) to (47) above;
$R_5$ is as defined in any one of paragraphs (48) to (54) above;
$R_6$ is as defined in any one of paragraphs (55) to (63) above; and
$R_7$ is as defined in any one of paragraphs (64) to (76) above.

In another embodiment of the compounds of formula Ia:
$A_1, A_2, A_3$ and $A_4$ are as defined in any one of paragraphs (1) to (3) above;
$R_2$ is as defined in any one of paragraphs (19) to (26) above;
$R_3$ is as defined in any one of paragraphs (29) to (37) above;
$R_4$ is as defined in any one of paragraphs (41) to (47) above;
$R_5$ is as defined in any one of paragraphs (50) to (54) above;
$R_6$ is as defined in any one of paragraphs (58) to (63) above; and
$R_7$ is as defined in any one of paragraphs (67) to (76) above.

In another embodiment of the compounds of formula Ia:
$A_1, A_2, A_3$ and $A_4$ are as defined in any one of paragraphs (1) to (3) above;
$R_2$ is as defined in any one of paragraphs (24) to (26) above;
$R_3$ is as defined in any one of paragraphs (32) to (37) above;
$R_4$ is as defined in any one of paragraphs (45) to (47) above;
$R_5$ is as defined in any one of paragraphs (52) to (54) above;
$R_6$ is as defined in any one of paragraphs (61) to (63) above; and
$R_7$ is as defined in any one of paragraphs (74) to (76) above.

In another embodiment of the compounds of formula Ia:
$A_1, A_2, A_3$ and $A_4$ are as defined in any one of paragraphs (1) to (3) above;
$R_2$ is as defined in paragraph (26) above;
$R_3$ is as defined in any one of paragraphs (34) to (37) above;
$R_4$ is as defined in paragraph (47) above;
$R_5$ is as defined in paragraph (54) above;
$R_6$ is as defined in paragraph (61) to (63) above; and
$R_7$ is as defined in any one of paragraphs (74) to (76) above.

In another embodiment of the compounds of formula Ia:
$A_1, A_2, A_3$ and $A_4$ are as defined in paragraph (3) above;
$R_2$ is as defined in paragraph (26) above;
$R_3$ is as defined in paragraph (37) above;
$R_4$ is as defined in paragraph (47) above;
$R_5$ is as defined in paragraph (54) above;
$R_6$ is as defined in paragraph (63) above; and
$R_7$ is as defined in paragraph (76) above.

In a particular group of compounds of the invention, $R_1$ is H and $R_2$ is C(O)OH, i.e. the compounds have the structural formula Ib (a sub-definition of formula I) shown below:

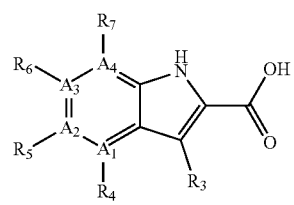

wherein $A_1, A_2, A_3, A_4, R_3, R_4, R_5, R_6$ and $R_7$ each have any one of the meanings defined herein; or a pharmaceutically acceptable salt, hydrate and/or solvate thereof.

In an embodiment of the compounds of formula Ib:
$A_1, A_2, A_3$ and $A_4$ are as defined in any one of paragraphs (1) to (3) above;
$R_3$ is as defined in any one of paragraphs (27) to (37) above;
$R_4$ is as defined in any one of paragraphs (38) to (47) above;
$R_5$ is as defined in any one of paragraphs (48) to (54) above;
$R_6$ is as defined in any one of paragraphs (55) to (63) above; and
$R_7$ is as defined in any one of paragraphs (64) to (76) above.

In another embodiment of the compounds of formula Ib:
$A_1, A_2, A_3$ and $A_4$ are as defined in any one of paragraphs (1) to (3) above;
$R_3$ is as defined in any one of paragraphs (29) to (37) above;
$R_4$ is as defined in any one of paragraphs (41) to (47) above;
$R_5$ is as defined in any one of paragraphs (50) to (54) above;
$R_6$ is as defined in any one of paragraphs (58) to (63) above; and
$R_7$ is as defined in any one of paragraphs (67) to (76) above.

In another embodiment of the compounds of formula Ib:
$A_1, A_2, A_3$ and $A_4$ are as defined in any one of paragraphs (1) to (3) above;
$R_3$ is as defined in any one of paragraphs (32) to 37) above;
$R_4$ is as defined in any one of paragraphs (45) to (47) above;
$R_5$ is as defined in any one of paragraphs (52) to (54) above;
$R_6$ is as defined in any one of paragraphs (61) to (63) above; and R<sub>7</sub> is as defined in any one of paragraphs (74) to (76) above.

In another embodiment of the compounds of formula Ib:
A<sub>1</sub>, A<sub>2</sub>, A<sub>3</sub> and A<sub>4</sub> are as defined in any one of paragraphs (1) to (3) above;
R<sub>3</sub> is as defined in any one of paragraphs (34) or (37) above;
R<sub>4</sub> is as defined in paragraph (47) above;
R<sub>5</sub> is as defined in paragraph (54) above;
R<sub>6</sub> is as defined in paragraph (61) to (63) above; and
R<sub>7</sub> is as defined in any one of paragraphs (74) to (76) above.

In another embodiment of the compounds of formula Ib:
A<sub>1</sub>, A<sub>2</sub>, A<sub>3</sub> and A<sub>4</sub> are as defined in paragraph (3) above;
R<sub>3</sub> is as defined in paragraph (37) above;
R<sub>4</sub> is as defined in paragraph (47) above;
R<sub>5</sub> is as defined in paragraph (54) above;
R<sub>6</sub> is as defined in paragraph (63) above; and
R<sub>7</sub> is as defined in paragraph (76) above.

In a particular group of compounds of the formula Ib, one of A<sub>1</sub>, A<sub>2</sub>, A<sub>3</sub> and A<sub>4</sub> is N.

In a particular group of compounds of the invention, R<sub>1</sub> is H, R<sub>2</sub> is C(O)OH and A<sub>1</sub>, A<sub>2</sub>, A<sub>3</sub> and A<sub>4</sub> are C, i.e. the compounds have the structural formula Ic (a sub-definition of formula I) shown below:

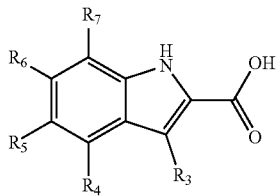

Ic wherein $R_3$, $R_4$, $R_5$, $R_6$ and $R_7$ each have any one of the meanings defined herein; or a pharmaceutically acceptable salt, hydrate and/or solvate thereof.

In an embodiment of the compounds of formula Ic:
R<sub>3</sub> is as defined in any one of paragraphs (27) to (37) above;
R<sub>4</sub> is as defined in any one of paragraphs (38) to (47) above;
R<sub>5</sub> is as defined in any one of paragraphs (48) to (54) above;
R<sub>6</sub> is as defined in any one of paragraphs (55) to (63) above; and
R<sub>7</sub> is as defined in any one of paragraphs (64) to (76) above.

In another embodiment of the compounds of formula Ic:
R<sub>3</sub> is as defined in any one of paragraphs (29) to (37) above;
R<sub>4</sub> is as defined in any one of paragraphs (41) to (47) above;
R<sub>5</sub> is as defined in any one of paragraphs (50) to (54) above;
R<sub>6</sub> is as defined in any one of paragraphs (58) to (63) above; and
R<sub>7</sub> is as defined in any one of paragraphs (67) to (76) above.

In another embodiment of the compounds of formula Ic:
R<sub>3</sub> is as defined in any one of paragraphs (32) to (37) above;
R<sub>4</sub> is as defined in any one of paragraphs (45) to (47) above;
R<sub>5</sub> is as defined in any one of paragraphs (52) to (54) above;
R<sub>6</sub> is as defined in any one of paragraphs (61) to (63) above; and
R<sub>7</sub> is as defined in any one of paragraphs (74) to (76) above.

In another embodiment of the compounds of formula Ic:
R<sub>3</sub> is as defined in any one of paragraphs (34) to (37) above;
R<sub>4</sub> is as defined in paragraph (47) above;
R<sub>5</sub> is as defined in paragraph (54) above;
R<sub>6</sub> is as defined paragraph (61) to (63) above; and
R<sub>7</sub> is as defined in any one of paragraphs (74) to (76) above.

In another embodiment of the compounds of formula Ic:
R<sub>3</sub> is as defined in paragraph (26) above;
R<sub>4</sub> is as defined in paragraph (47) above;
R<sub>5</sub> is as defined in paragraph (54) above;
R<sub>6</sub> is as defined in paragraph (63) above; and
R<sub>7</sub> is as defined in paragraph (76) above.

In a particular group of compounds of the invention, R<sub>1</sub> is H, R<sub>2</sub> is C(O)OH, R<sub>4</sub> is H and A<sub>1</sub>, A<sub>2</sub>, A<sub>3</sub> and A<sub>4</sub> are C, i.e. the compounds have the structural formula Id (a sub-definition of formula I) shown below:

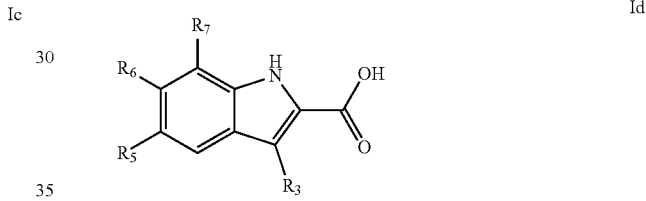

Id wherein $R_3$, $R_5$, $R_6$ and $R_7$ each have any one of the meanings defined herein; or a pharmaceutically acceptable salt, hydrate and/or solvate thereof.

In an embodiment of the compounds of formula Id:
R<sub>3</sub> is as defined in any one of paragraphs (27) to (37) above;
R<sub>5</sub> is as defined in any one of paragraphs (48) to (54) above;
R<sub>6</sub> is as defined in any one of paragraphs (55) to (63) above; and
R<sub>7</sub> is as defined in any one of paragraphs (64) to (76) above.

In another embodiment of the compounds of formula Id:
R<sub>3</sub> is as defined in any one of paragraphs (29) to (37) above;
R<sub>5</sub> is as defined in any one of paragraphs (50) to (54) above;
R<sub>6</sub> is as defined in any one of paragraphs (85) to (63) above; and
R<sub>7</sub> is as defined in any one of paragraphs (67) to (76) above.

In another embodiment of the compounds of formula Id:
R<sub>3</sub> is as defined in any one of paragraphs (32) to (37) above;
R<sub>5</sub> is as defined in any one of paragraphs (52) to (55) above;
R<sub>6</sub> is as defined in any one of paragraphs (61) to (63) above; and
R<sub>7</sub> is as defined in any one of paragraphs (74) to (76) above.

In another embodiment of the compounds of formula Id:

R$_3$ is as defined in any one of paragraphs (34) to (37) above;

R$_5$ is as defined in paragraph (55) above;

R$_6$ is as defined paragraph (31) to (63) above; and

R$_7$ is as defined in any one of paragraphs (74) to (76) above.

In another embodiment of the compounds of formula Id:

R$_3$ is as defined in paragraph (37) above;

R$_5$ is as defined in paragraph (55) above;

R$_6$ is as defined in paragraph (63) above; and

R$_7$ is as defined in paragraph (76) above.

Particular compounds of the present invention include any of the compounds exemplified in the present application, or a pharmaceutically acceptable salt or solvate thereof, and, in particular, any of the following:

Example 1:
3-(3-chlorophenyl)-7-methyl-1H-indole-2-carboxylic acid

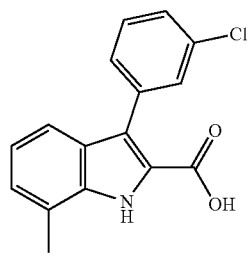 [SMILES: Cc1cccc2c(-c3cccc(Cl)c3)c(C(=O)O)[nH]c12]

Example 2: 7-methyl-3-(4-(trifluoromethoxy)phenyl)-1H-indole-2-carboxylic acid

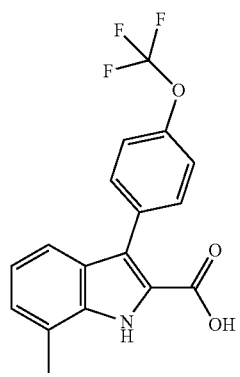 [SMILES: Cc1cccc2c(-c3ccc(OC(F)(F)F)cc3)c(C(=O)O)[nH]c12]

Example 3: 3-(3,5-dichlorophenyl)-7-methyl-1H-indole-2-carboxylicacid

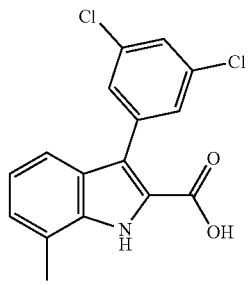 [SMILES: Cc1cccc2c(-c3cc(Cl)cc(Cl)c3)c(C(=O)O)[nH]c12]

Example 4: 7-methyl-3-(pyridin-4-yl)-1H-indole-2-carboxylic acid

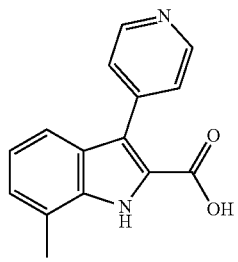 [SMILES: Cc1cccc2c(-c3ccncc3)c(C(=O)O)[nH]c12]

Example 5:3-(4-carbamoylphenyl)-7-methyl-1H-indole-2-carboxylic acid

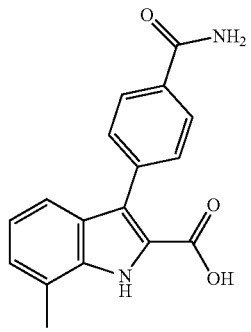 [SMILES: Cc1cccc2c(-c3ccc(C(N)=O)cc3)c(C(=O)O)[nH]c12]

Example 6: 7-methyl-3-(4-sulfamoylphenyl)-1H-indole-2-carboxylic acid

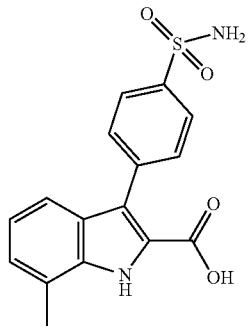 [SMILES: Cc1cccc2c(-c3ccc(S(N)(=O)=O)cc3)c(C(=O)O)[nH]c12]

Example 7:
3-(4-cyanophenyl)-7-methyl-1H-indole-2-carboxylic acid
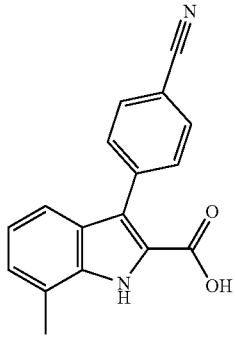 [SMILES: Cc1cccc2c(-c3ccc(C#N)cc3)c(C(=O)O)[nH]c12]
Example 8:
7-methyl-3-(4-nitrophenyl)-1H-indole-2-carboxylic acid
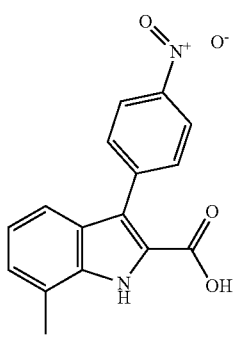
Example 9: 3-(4-methoxyphenyl)-7-methyl-1H-indole-2-carboxylic acid
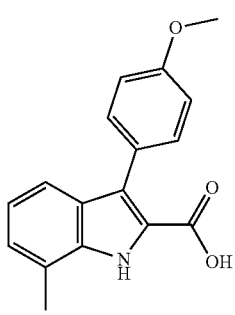 [SMILES: COc1ccc(-c2c(C(=O)O)[nH]c3c(C)cccc23)cc1]
Example 10:
3-(4-bromophenyl)-7-methyl-1H-indole-2-carboxylic acid
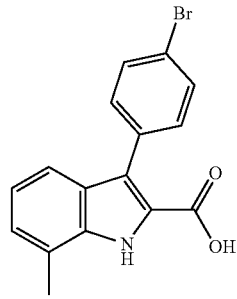 [SMILES: Cc1cccc2c(-c3ccc(Br)cc3)c(C(=O)O)[nH]c12]
Example 11: 7-methyl-3-(4-(trifluoromethyl)phenyl)-1H-indole-2-carboxylic acid
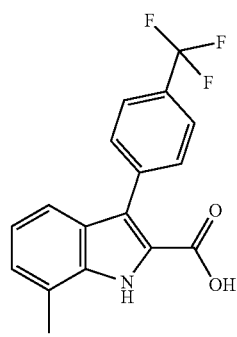 [SMILES: Cc1cccc2c(-c3ccc(C(F)(F)F)cc3)c(C(=O)O)[nH]c12]
Example 12: 7-methyl-3-(4-(methylsulfonyl)phenyl)-1H-indole-2-carboxylic acid
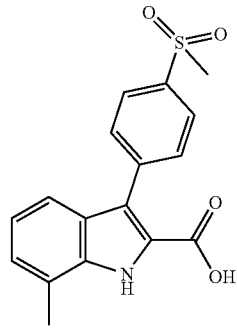 [SMILES: Cc1cccc2c(-c3ccc(S(C)(=O)=O)cc3)c(C(=O)O)[nH]c12]

Example 13: 7-methyl-3-(4-morpholinophenyl)-1H-indole-2-carboxylic acid
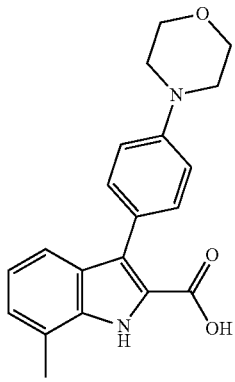 [SMILES: Cc1cccc2c(-c3ccc(N4CCOCC4)cc3)c(C(=O)O)[nH]c12]
Example 14: 7-methyl-3-(3-sulfamoylphenyl)-1H-indole-2-carboxylic acid
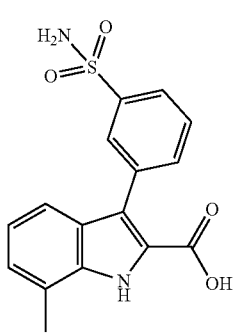 [SMILES: Cc1cccc2c(-c3cccc(S(N)(=O)=O)c3)c(C(=O)O)[nH]c12]
Example 15: 7-methyl-3-(3-nitrophenyl)-1H-indole-2-carboxylic acid
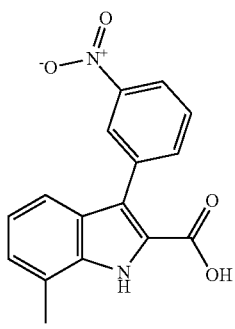
Example 16: 7-methyl-3-(3-(methylsulfonyl)phenyl)-1H-indole-2-carboxylic acid
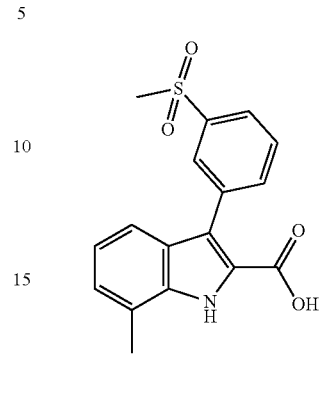
Example 17: 3-(3-(dimethylamino)phenyl)-7-methyl-1H-indole-2-carboxylic acid
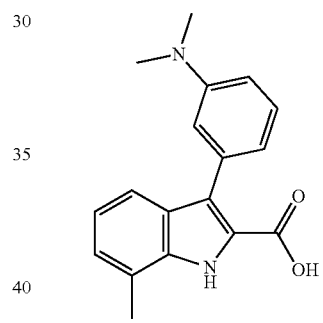
Example 18: 3-(3-bromophenyl)-7-methyl-1H-indole-2-carboxylic acid
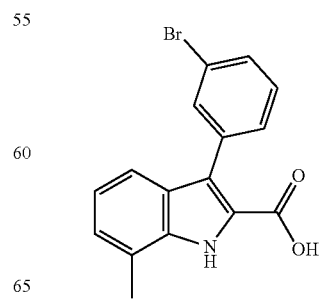

Example 19: 3-(1H-indazol-5-yl)-7-methyl-1H-indole-2-carboxylic acid

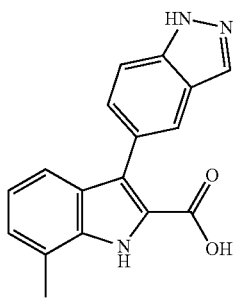 [SMILES: Cc1cccc2c(-c3ccc4[nH]ncc4c3)c(C(=O)O)[nH]c12]

Example 20 3-(2-methoxyphenyl)-7-methyl-1H-indole-2-carboxylic acid

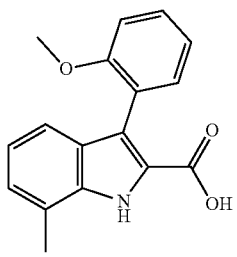 [SMILES: COc1ccccc1-c1c(C(=O)O)[nH]c2c(C)cccc12]

Example 21: 3-([1,2,4]triazolo[1,5-a]pyridin-7-yl)-7-methyl-1H-indole-2-carboxylic acid

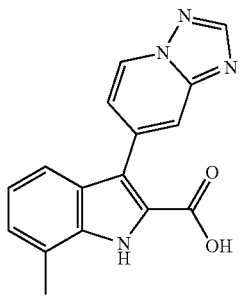 [SMILES: Cc1cccc2c(-c3ccn4ncnc4c3)c(C(=O)O)[nH]c12]

Example 22: 7-methyl-3-(pyrimidin-5-yl)-1H-indole-2-carboxylic acid

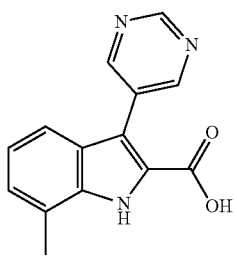 [SMILES: Cc1cccc2c(-c3cncnc3)c(C(=O)O)[nH]c12]

Example 23: 3-(4-aminophenyl)-7-methyl-1H-indole-2-carboxylic acid

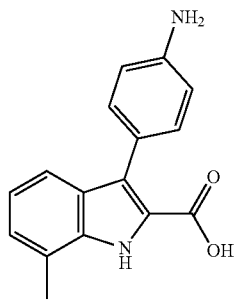 [SMILES: Cc1cccc2c(-c3ccc(N)cc3)c(C(=O)O)[nH]c12]

Example 24: 7-methyl-3-(pyridin-3-yl)-1H-indole-2-carboxylic acid

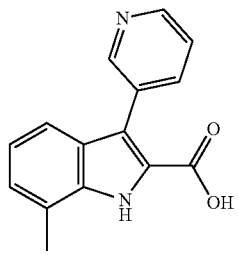 [SMILES: Cc1cccc2c(-c3cccnc3)c(C(=O)O)[nH]c12]

Example 25: 3-(1-(tert-butoxycarbonyl)-1,2,3,6-tetrahydropyridin-4-yl)-7-methyl-1H-indole-2-carboxylic acid

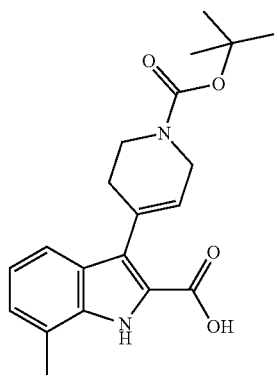 [SMILES: Cc1cccc2c(C3=CCN(C(=O)OC(C)(C)C)CC3)c(C(=O)O)[nH]c12]

Example 26: 7-methyl-3-(1-methyl-1H-pyrazol-4-yl)-1H-indole-2-carboxylic acid

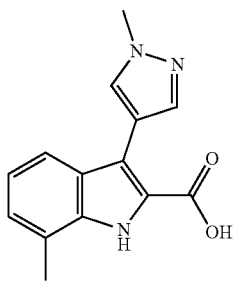 [SMILES: Cc1cccc2c(-c3cnn(C)c3)c(C(=O)O)[nH]c12]

Example 27: 3-(cyclopent-1-en-1-yl)-7-methyl-1H-indole-2-carboxylic acid

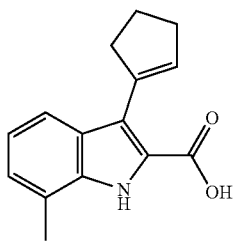 [SMILES: Cc1cccc2c(C3=CCCC3)c(C(=O)O)[nH]c12]

Example 28: 3-(2-cyanophenyl)-7-methyl-1H-indole-2-carboxylic acid

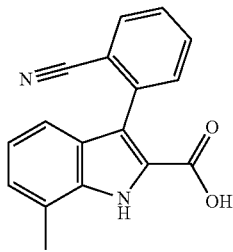 [SMILES: Cc1cccc2c(-c3ccccc3C#N)c(C(=O)O)[nH]c12]

Example 29: 3-(4-(N,N-dimethylsulfamoyl)phenyl)-7-methyl-1H-indole-2-carboxylic acid

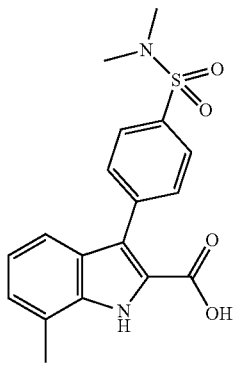 [SMILES: Cc1cccc2c(-c3ccc(S(=O)(=O)N(C)C)cc3)c(C(=O)O)[nH]c12]

Example 30: 3-(4-acetamidophenyl)-7-methyl-1H-indole-2-carboxylic acid

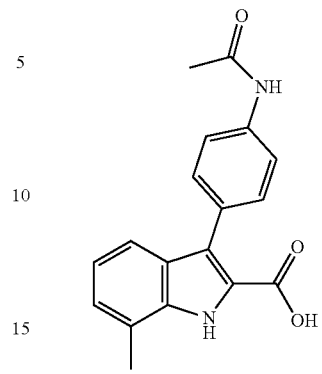

Example 31: 3-(1H-indazol-4-yl)-7-methyl-1H-indole-2-carboxylic acid

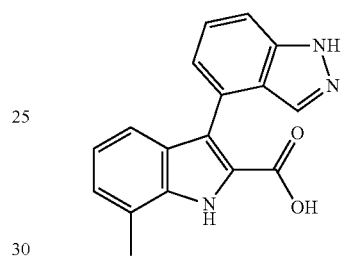

Example 32: 3-(1H-indazol-6-yl)-7-methyl-1H-indole-2-carboxylic acid

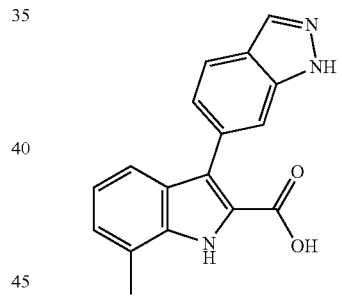

Example 33: 3-(4-((1H-1,2,4-triazol-1-yl)methyl)phenyl)-7-methyl-1H-indole-2-carboxylic acid

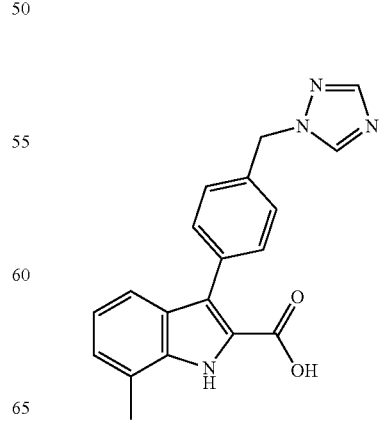

Example 34: 3-(4-((1H-pyrazol-1-yl)methyl)phenyl)-7-methyl-1H-indole-2-carboxylicacid

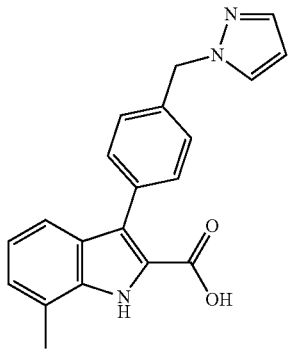 [SMILES: Cc1cccc2c(-c3ccc(Cn4cccn4)cc3)c(C(=O)O)[nH]c12]

Example 35: 3-(4-chlorophenyl)-1,7-dimethyl-1H-indole-2-carboxylic acid

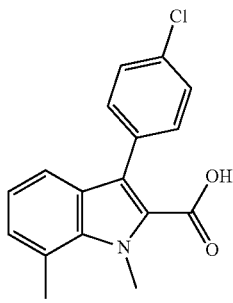 [SMILES: Cc1cccc2c(-c3ccc(Cl)cc3)c(C(=O)O)n(C)c12]

Example 36: 7-methyl-3-(1,2,3,6-tetrahydropyridin-4-yl)-1H-indole-2-carboxylic acid

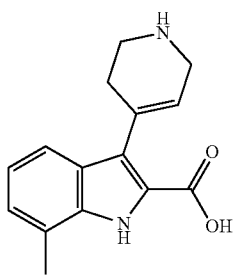

Example 37: 7-methyl-3-phenyl-1H-indole-2-carboxylic acid

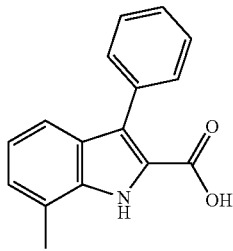 [SMILES: Cc1cccc2c(-c3ccccc3)c(C(=O)O)[nH]c12]

Example 38: 3-(3,5-dimethylphenyl)-7-methyl-1H-indole-2-carboxylic acid

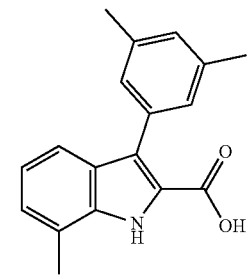 [SMILES: Cc1cc(C)cc(-c2c(C(=O)O)[nH]c3c(C)cccc23)c1]

Example 39: 3-(2-chlorophenyl)-7-methyl-1H-indole-2-carboxylic acid

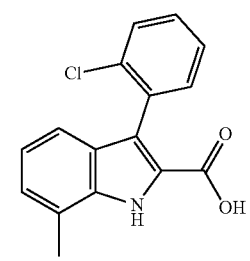 [SMILES: Cc1cccc2c(-c3ccccc3Cl)c(C(=O)O)[nH]c12]

Example 40: 3-([1,1'-biphenyl]-4-yl)-7-methyl-1H-indole-2-carboxylic acid

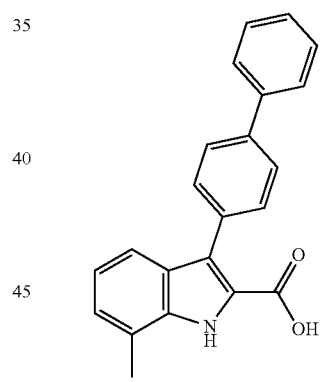

Example 41: 7-methyl-3-(o-tolyl)-1H-indole-2-carboxylic acid

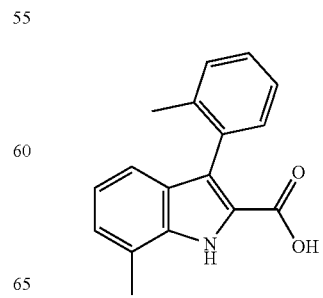

Example 42:
3-(4-chlorophenyl)-7-methyl-1H-indole-2-carboxylic acid

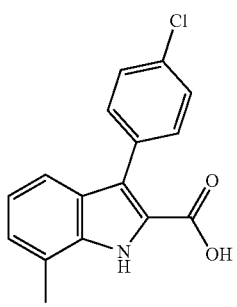

Example 43: 3-(4-chloro-3-(trifluoromethyl)phenyl)-7-methyl-1H-indole-2-carboxylic acid

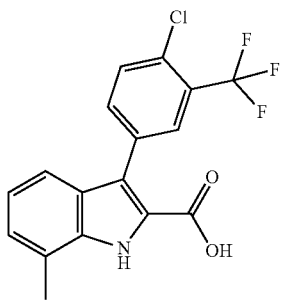 [SMILES: Cc1cccc2c(-c3ccc(Cl)c(C(F)(F)F)c3)c(C(=O)O)[nH]c12]

Example 44: 7-methyl-3-(3-(trifluoromethyl)phenyl)-1H-indole-2-carboxylic acid

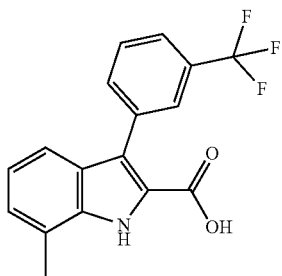 [SMILES: Cc1cccc2c(-c3cccc(C(F)(F)F)c3)c(C(=O)O)[nH]c12]

Example 45: 3-(4-cyclopropylphenyl)-7-methyl-1H-indole-2-carboxylic acid

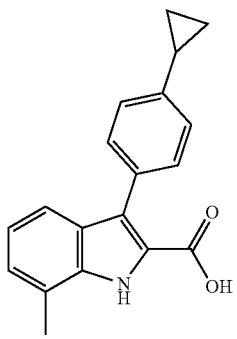 [SMILES: Cc1cccc2c(-c3ccc(C4CC4)cc3)c(C(=O)O)[nH]c12]

Example 46: 3-iodo-7-methyl-1H-indole-2-carboxylic acid

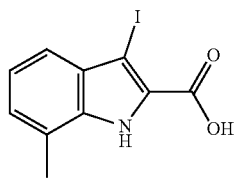

Example 47: 6-methyl-3-(4-sulfamoylphenyl)-1H-indole-2-carboxylic acid

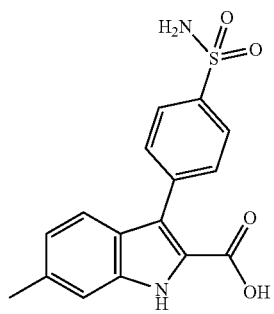 [SMILES: Cc1ccc2c(-c3ccc(S(N)(=O)=O)cc3)c(C(=O)O)[nH]c2c1]

Example 48: 3-(4-carbamoylphenyl)-6-methyl-1H-indole-2-carboxylic acid

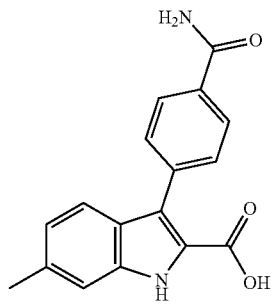 [SMILES: Cc1ccc2c(-c3ccc(C(N)=O)cc3)c(C(=O)O)[nH]c2c1]

Example 49: 3-(4-fluorophenyl)-7-methyl-1H-indole-2-carboxylic acid

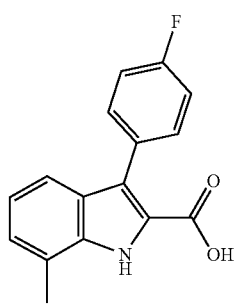 [SMILES: Cc1cccc2c(-c3ccc(F)cc3)c(C(=O)O)[nH]c12]

Example 50: 3-(4-fluorophenyl)-7-methoxy-1H-indole-2-carboxylic acid
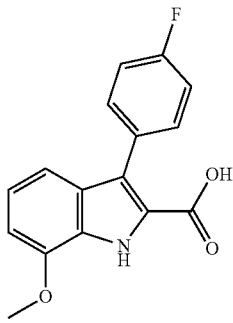 [SMILES: COc1cccc2c(-c3ccc(F)cc3)c(C(=O)O)[nH]c12]
Example 51: 3-(4-fluorophenyl)-7-(trifluoromethyl)-1H-indole-2-carboxylic acid
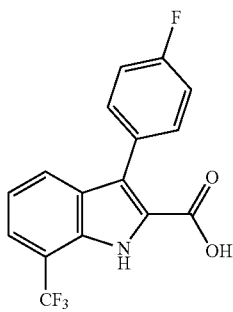 [SMILES: O=C(O)c1[nH]c2c(C(F)(F)F)cccc2c1-c1ccc(F)cc1]
Example 52: 3-(4-fluorophenyl)-7-propyl-1H-indole-2-carboxylic acid
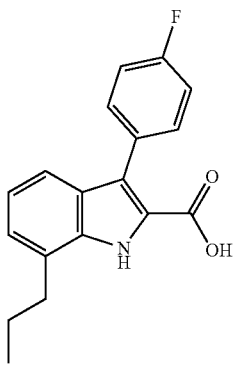 [SMILES: CCCc1cccc2c(-c3ccc(F)cc3)c(C(=O)O)[nH]c12]
Example 53: 3-(4-fluorophenyl)-7-isopropyl-1H-indole-2-carboxylic acid
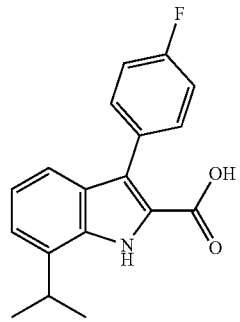 [SMILES: CC(C)c1cccc2c(-c3ccc(F)cc3)c(C(=O)O)[nH]c12]
Example 54: 7-chloro-3-(4-fluorophenyl)-1H-indole-2-carboxylic acid
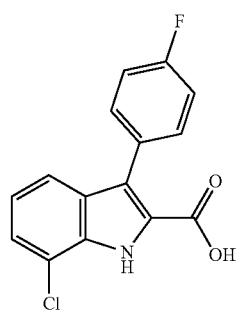
Example 55: 3-(4-fluorophenyl)-6-methoxy-7-methyl-1H-indole-2-carboxylicacid
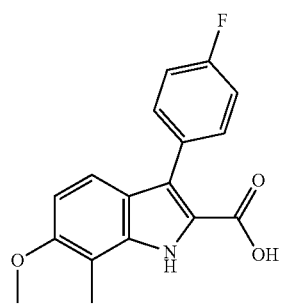 [SMILES: COc1ccc2c(-c3ccc(F)cc3)c(C(=O)O)[nH]c2c1C]

Example 56: 3-(4-fluorophenyl)-6,7-dimethyl-1H-indole-2-carboxylic acid

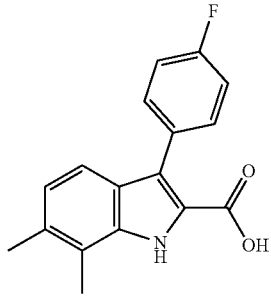 [SMILES: Cc1ccc2c(-c3ccc(F)cc3)c(C(=O)O)[nH]c2c1C]

Example 57: 7-(tert-butyl)-3-(4-fluorophenyl)-1H-indole-2-carboxylic acid

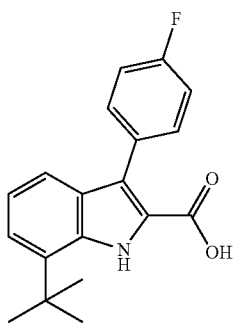 [SMILES: CC(C)(C)c1cccc2c(-c3ccc(F)cc3)c(C(=O)O)[nH]c12]

Example 58: 5-fluoro-3-(4-fluorophenyl)-7-methyl-1H-indole-2-carboxylic acid

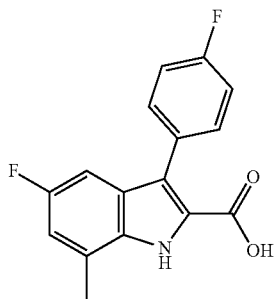

Example 59: 3-(4-fluorophenyl)-5,7-dimethyl-1H-indole-2-carboxylic acid

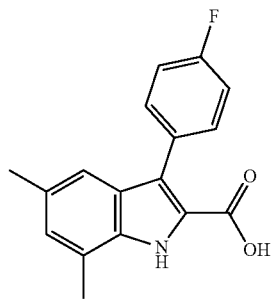 [SMILES: Cc1cc(C)c2[nH]c(C(=O)O)c(-c3ccc(F)cc3)c2c1]

Example 60: 3-(4-fluorophenyl)-5-methoxy-7-methyl-1H-indole-2-carboxylic acid

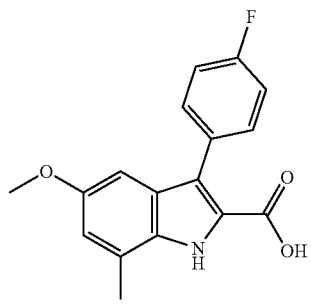 [SMILES: COc1cc(C)c2[nH]c(C(=O)O)c(-c3ccc(F)cc3)c2c1]

Example 61: 3-(4-fluorophenyl)-7-(2-methoxy-ethyl)-1H-indole-2-carboxylic acid

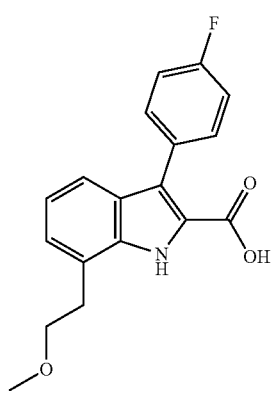 [SMILES: COCCc1cccc2c(-c3ccc(F)cc3)c(C(=O)O)[nH]c12]

Example 62: 3-(4-fluorophenyl)-7-(2-phenoxy-ethyl)-1H-indole-2-carboxylic acid

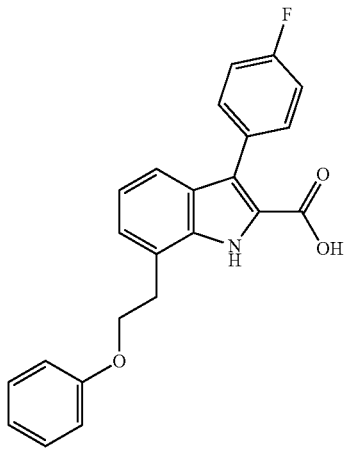 [SMILES: O=C(O)c1[nH]c2c(CCOc3ccccc3)cccc2c1-c1ccc(F)cc1]

Example 63: 7-methyl-3-(pyridin-2-yl)-1H-indole-2-carboxylic acid

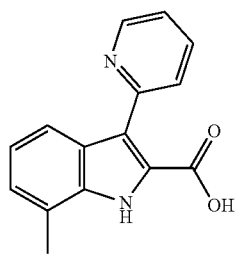 [SMILES: Cc1cccc2c(-c3ccccn3)c(C(=O)O)[nH]c12]

Example 64: 3-(4-fluorophenyl)-7-methyl-6-phenoxy-1H-indole-2-carboxylic acid

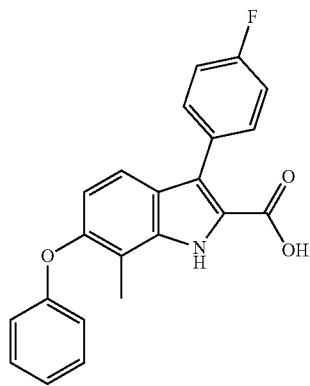 [SMILES: Cc1c(Oc2ccccc2)ccc2c(-c3ccc(F)cc3)c(C(=O)O)[nH]c12]

Example 65: 7-isopropyl-3-(4-sulfamoylphenyl)-1H-indole-2-carboxylic acid

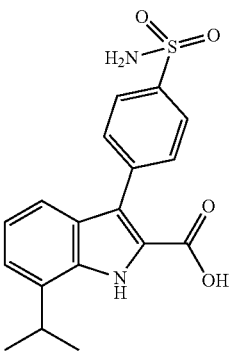 [SMILES: CC(C)c1cccc2c(-c3ccc(S(N)(=O)=O)cc3)c(C(=O)O)[nH]c12]

Example 66: 7-isopropyl-3-phenyl-1H-indole-2-carboxylic acid

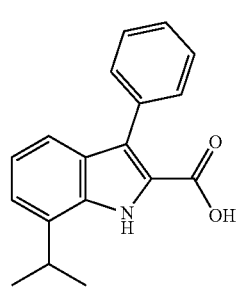

Example 67: 7-isopropyl-3-(4-(methylsulfonyl)phenyl)-1H-indole-2-carboxylic acid

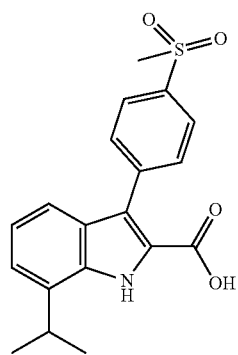 [SMILES: CC(C)c1cccc2c(-c3ccc(S(C)(=O)=O)cc3)c(C(=O)O)[nH]c12]

Example 68: 7-isopropyl-3-(pyridin-4-yl)-1H-indole-2-carboxylic acid

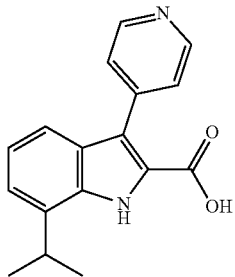 [SMILES: CC(C)c1cccc2c(-c3ccncc3)c(C(=O)O)[nH]c12]

Example 69: 3-(4-carbamoylphenyl)-7-isopropyl-1H-indole-2-carboxylic acid

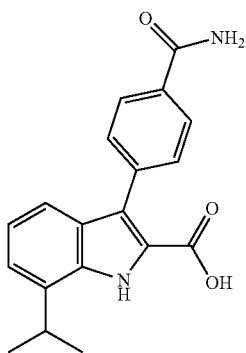 [SMILES: CC(C)c1cccc2c(-c3ccc(C(N)=O)cc3)c(C(=O)O)[nH]c12]

Example 70: 7-isopropyl-3-(4-morpholinophenyl)-1H-indole-2-carboxylic acid

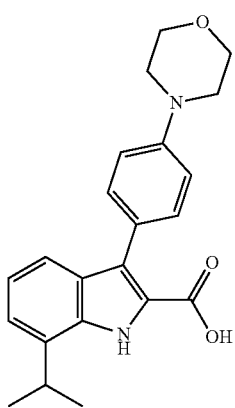 [SMILES: CC(C)c1cccc2c(-c3ccc(N4CCOCC4)cc3)c(C(=O)O)[nH]c12]

Example 71: 3-(4-chlorophenyl)-7-isopropyl-1H-indole-2-carboxylic acid

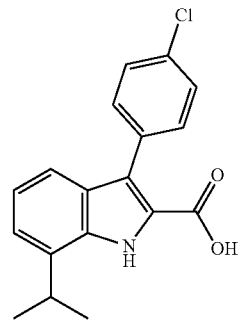 [SMILES: CC(C)c1cccc2c(-c3ccc(Cl)cc3)c(C(=O)O)[nH]c12]

Example 72: 3-(2-chlorophenyl)-7-isopropyl-1H-indole-2-carboxylic acid

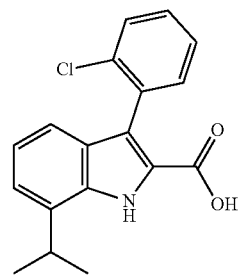 [SMILES: CC(C)c1cccc2c(-c3ccccc3Cl)c(C(=O)O)[nH]c12]

Example 73: 3-(4-(N,N-dimethylsulfamoyl)phenyl)-7-isopropyl-1H-indole-2-carboxylic acid

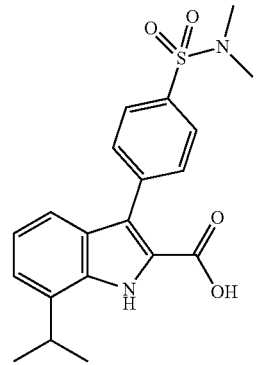 [SMILES: CC(C)c1cccc2c(-c3ccc(S(=O)(=O)N(C)C)cc3)c(C(=O)O)[nH]c12]

Example 74: 3-(4-(dimethylcarbamoyl)phenyl)-7-isopropyl-1H-indole-2-carboxylic acid

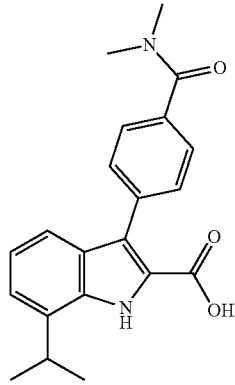 [SMILES: CC(C)c1cccc2c(-c3ccc(C(=O)N(C)C)cc3)c(C(=O)O)[nH]c12]

Example 75: 3-(1H-indazol-5-yl)-7-isopropyl-1H-indole-2-carboxylic acid

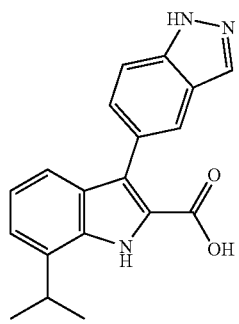 [SMILES: CC(C)c1cccc2c(-c3ccc4[nH]ncc4c3)c(C(=O)O)[nH]c12]

Example 76: 3-(3,5-dichlorophenyl)-7-isopropyl-1H-indole-2-carboxylic acid

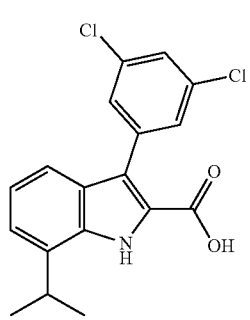 [SMILES: CC(C)c1cccc2c(-c3cc(Cl)cc(Cl)c3)c(C(=O)O)[nH]c12]

Example 77: 3-(2,3-dimethoxyphenyl)-7-isopropyl-1H-indole-2-carboxylic acid

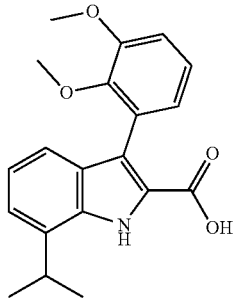 [SMILES: COc1cccc(-c2c(C(=O)O)[nH]c3c(C(C)C)cccc23)c1OC]

Example 78: 3-(3,5-difluorophenyl)-7-isopropyl-1H-indole-2-carboxylic acid

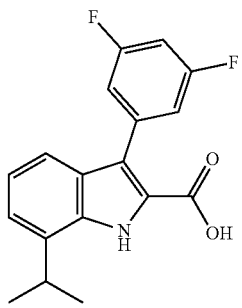 [SMILES: CC(C)c1cccc2c(-c3cc(F)cc(F)c3)c(C(=O)O)[nH]c12]

Example 79: 3-(4-((1H-pyrazol-1-yl)methyl)phenyl)-7-isopropyl-1H-indole-2-carboxylic acid

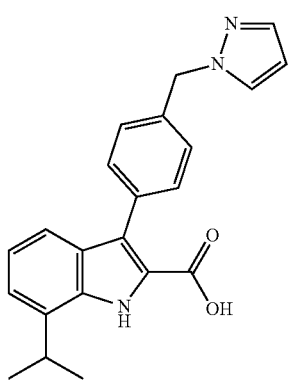 [SMILES: CC(C)c1cccc2c(-c3ccc(Cn4cccn4)cc3)c(C(=O)O)[nH]c12]

Example 80: 3-(4-((1H-1,2,4-triazol-1-yl)methyl)phenyl)-7-isopropyl-1H-indole-2-carboxylic acid

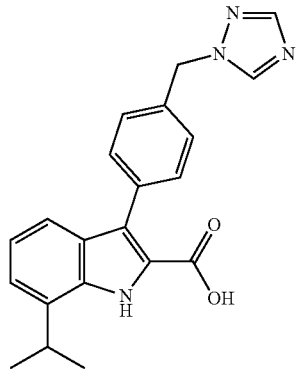 [SMILES: CC(C)c1cccc2c(-c3ccc(Cn4cncn4)cc3)c(C(=O)O)[nH]c12]

Example 81: 3-(4-(N,N-dimethylsulfamoyl)phenyl)-7-(2-phenoxyethyl)-1H-indole-2-carboxylic acid

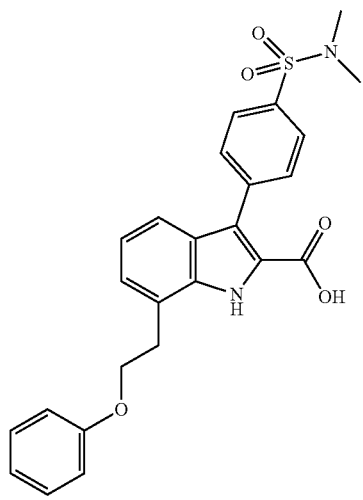 [SMILES: CN(C)S(=O)(=O)c1ccc(-c2c(C(=O)O)[nH]c3c(CCOc4ccccc4)cccc23)cc1]

Example 82: 3-(4-(N,N-dimethylsulfamoyl)phenyl)-7-methyl-6-phenoxy-1H-indole-2-carboxylic acid

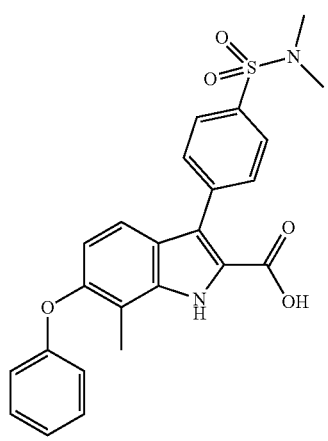 [SMILES: Cc1c(Oc2ccccc2)ccc2c(-c3ccc(S(=O)(=O)N(C)C)cc3)c(C(=O)O)[nH]c12]

Example 83: 3-(4-(dimethylcarbamoyl)phenyl)-7-(2-phenoxyethyl)-1H-indole-2-carboxylic acid

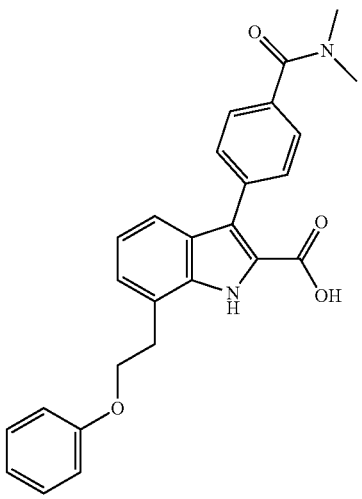 [SMILES: CN(C)C(=O)c1ccc(-c2c(C(=O)O)[nH]c3c(CCOc4ccccc4)cccc23)cc1]

Example 84: 3-(4-chlorophenyl)-7-(2-phenoxyethyl)-1H-indole-2-carboxylic acid

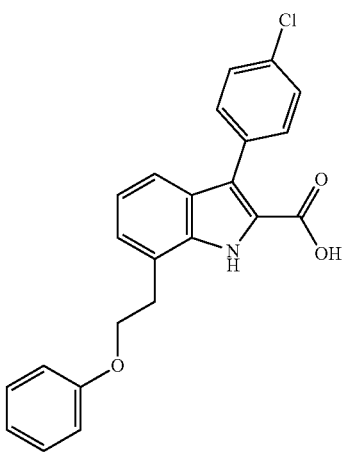 [SMILES: O=C(O)c1[nH]c2c(CCOc3ccccc3)cccc2c1-c1ccc(Cl)cc1]

Example 85: 3-(4-chlorophenyl)-7-methyl-6-phenoxy-1H-indole-2-carboxylic acid

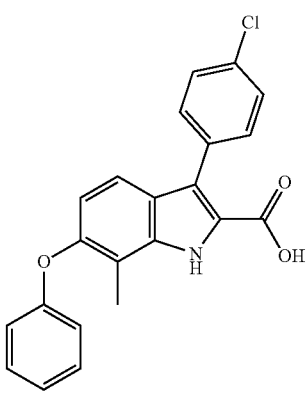

Example 86: 3-(4-(dimethylcarbamoyl)phenyl)-7-methyl-6-phenoxy-1H-indole-2-carboxylic acid

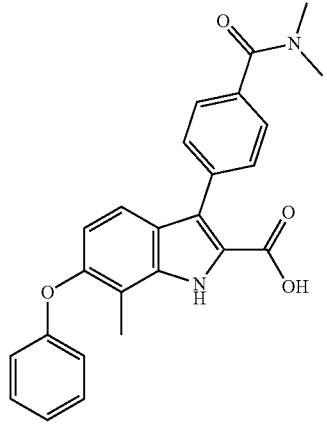 [SMILES: Cc1c(Oc2ccccc2)ccc2c(-c3ccc(C(=O)N(C)C)cc3)c(C(=O)O)[nH]c12]

Example 87: 7-isopropyl-3-(4-(methylcarbamoyl)phenyl)-1H-indole-2-carboxylic acid

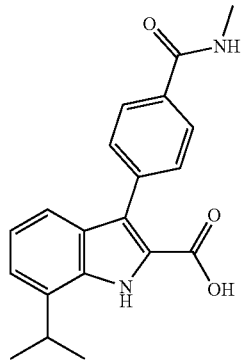 [SMILES: CNC(=O)c1ccc(-c2c(C(=O)O)[nH]c3c(C(C)C)cccc23)cc1]

Example 88: 7-isopropyl-3-(4-(N-methylsulfamoyl)phenyl)-1H-indole-2-carboxylic acid

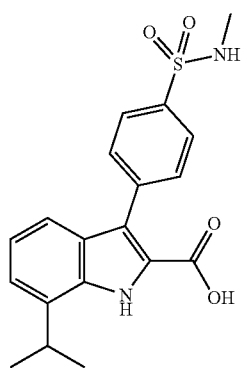 [SMILES: CNS(=O)(=O)c1ccc(-c2c(C(=O)O)[nH]c3c(C(C)C)cccc23)cc1]

Example 89: 7-isopropyl-3-(5-methylthiophen-2-yl)-1H-indole-2-carboxylic acid

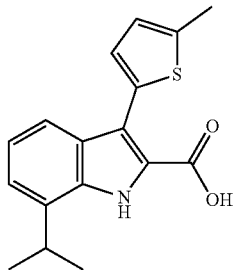

Example 90: 3-(4-(acetamidomethyl)phenyl)-7-isopropyl-1H-indole-2-carboxylic acid

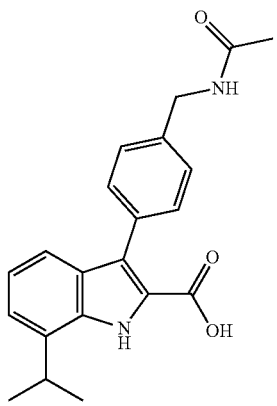 [SMILES: CC(=O)NCc1ccc(-c2c(C(=O)O)[nH]c3c(C(C)C)cccc23)cc1]

Example 91: 3-(4-carboxyphenyl)-7-isopropyl-1H-indole-2-carboxylic acid

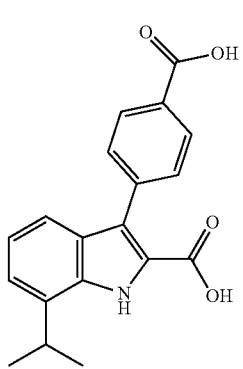 [SMILES: CC(C)c1cccc2c(-c3ccc(C(=O)O)cc3)c(C(=O)O)[nH]c12]

Example 92: 7-(tert-butyl)-3-(4-(dimethylcarbamoyl)phenyl)-1H-indole-2-carboxylic acid

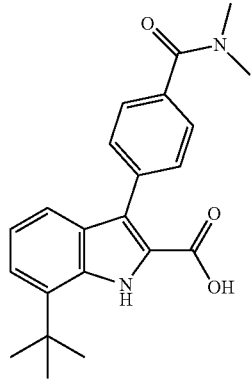 [SMILES: CN(C)C(=O)c1ccc(-c2c(C(=O)O)[nH]c3c(C(C)(C)C)cccc23)cc1]

Example 95: 7-isopropyl-3-(4-(morpholinosulfonyl)phenyl)-1H-indole-2-carboxylicacid

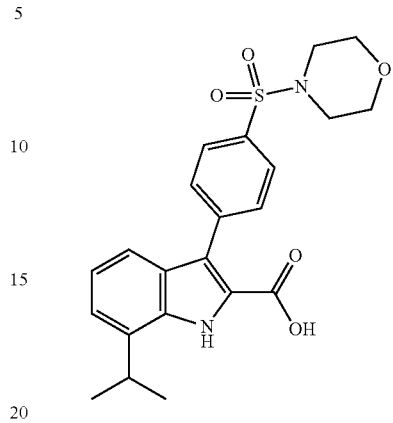

Example 93: 7-(tert-butyl)-3-(4-(N,N-dimethylsulfamoyl)phenyl)-1H-indole-2-carboxylic acid

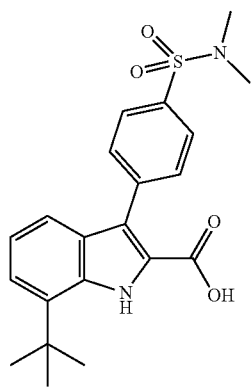 [SMILES: CN(C)S(=O)(=O)c1ccc(-c2c(C(=O)O)[nH]c3c(C(C)(C)C)cccc23)cc1]

Example 96: 7-isopropyl-3-(4-(methylsulfonamidomethyl)phenyl)-1H-indole-2-carboxylic acid

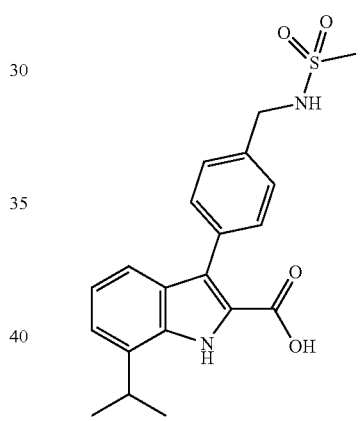

Example 94: 7-isopropyl-3-(4-(morpholinomethyl)phenyl)-1H-indole-2-carboxylic acid

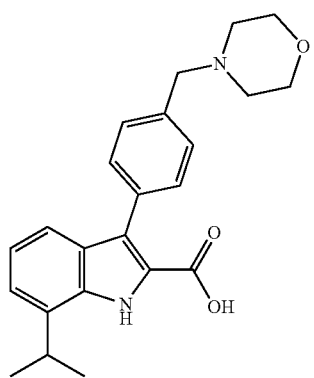 [SMILES: CC(C)c1cccc2c(-c3ccc(CN4CCOCC4)cc3)c(C(=O)O)[nH]c12]

Example 97: 3-(4-((dimethylamino)methyl)phenyl)-7-isopropyl-1H-indole-2-carboxylicacid

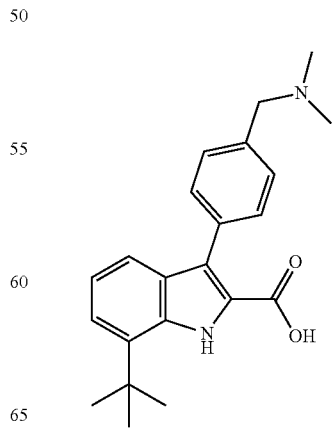

Example 98: 7-isopropyl-3-(6-morpholinopyridin-3-yl)-1H-indole-2-carboxylic acid

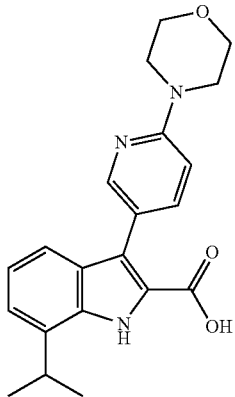 [SMILES: CC(C)c1cccc2c(-c3ccc(N4CCOCC4)nc3)c(C(=O)O)[nH]c12]

Example 99: 7-isopropyl-3-(4-(pyrrolidin-1-ylsulfonyl)phenyl)-1H-indole-2-carboxylic acid

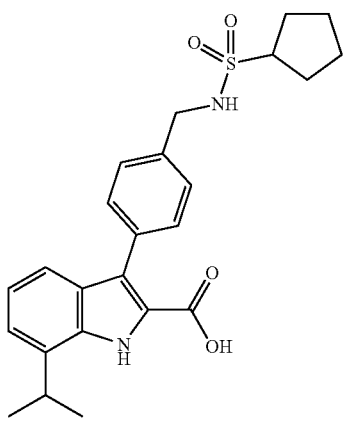 [SMILES: CC(C)c1cccc2c(-c3ccc(CNS(=O)(=O)C4CCCC4)cc3)c(C(=O)O)[nH]c12]

Example 100: 3-(4-((1H-tetrazol-1-yl)methyl)phenyl)-7-isopropyl-1H-indole-2-carboxylic acid

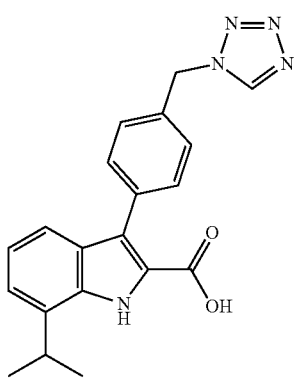 [SMILES: CC(C)c1cccc2c(-c3ccc(Cn4cnnn4)cc3)c(C(=O)O)[nH]c12]

Example 101: 3-(2-chloro-4-(dimethylcarbamoyl)phenyl)-7-isopropyl-1H-indole-2-carboxylic acid

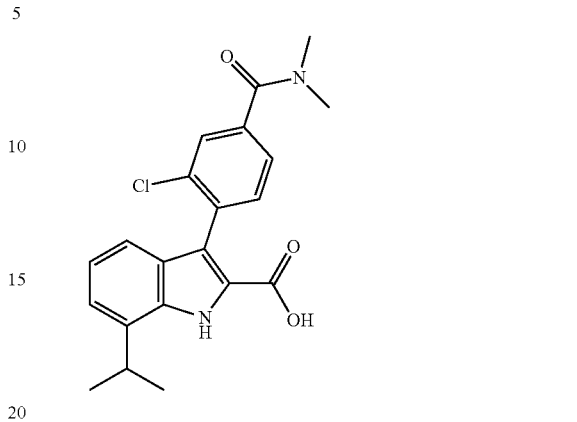

Example 102: 4-(7-isopropyl-2-(1H-tetrazol-5-yl)-1H-indol-3-yl)-N,N-dimethylbenzenesulfonamide Example 103: 3-cyclohexyl-7-methyl-1H-indole-2-carboxylic acid

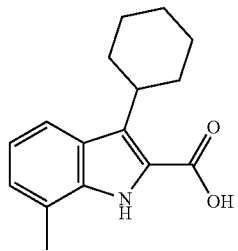 [SMILES: Cc1cccc2c(C3CCCCC3)c(C(=O)O)[nH]c12]

Example 104:
3-cyclopentyl-7-methyl-1H-indole-2-carboxylic acid

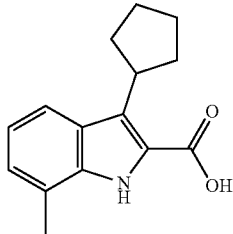 [SMILES: Cc1cccc2c(C3CCCC3)c(C(=O)O)[nH]c12]

Example 105: 3-(1-(tert-butoxycarbonyl)piperidin-4-yl)-7-methyl-1H-indole-2-carboxylic acid

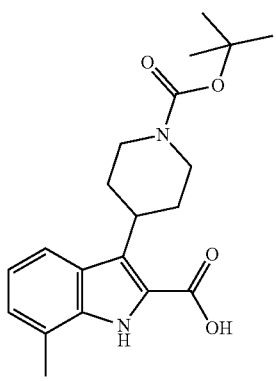 [SMILES: Cc1cccc2c(C3CCN(C(=O)OC(C)(C)C)CC3)c(C(=O)O)[nH]c12]

Example 106: 7-cyclopropyl-3-(4-fluorophenyl)-1H-indole-2-carboxylic acid

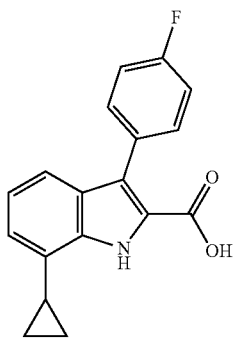 [SMILES: O=C(O)c1[nH]c2c(C3CC3)cccc2c1-c1ccc(F)cc1]

Example 107:
3-(4-chlorobenzyl)-7-methyl-1H-indole-2-carboxylic acid

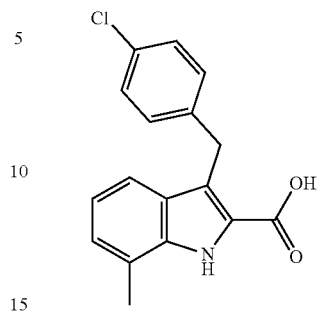

Example 108: 3-(4-fluorophenyl)-7-(2-hydroxyethyl)-1H-indole-2-carboxylic acid

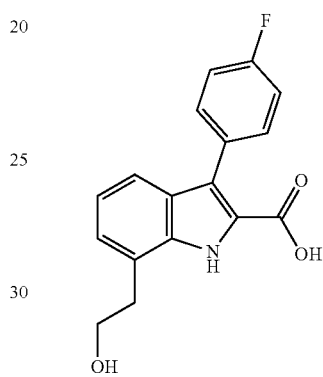

Example 109: 3-phenyl-1H-indole-2-carboxylic acid

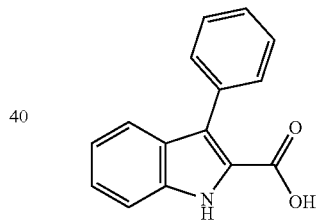

Example 110: 3-(4-fluorophenyl)-7-methyl-N'-(4-(methylsulfonyl)phenyl)-1H-indole-2-carbohydrazide

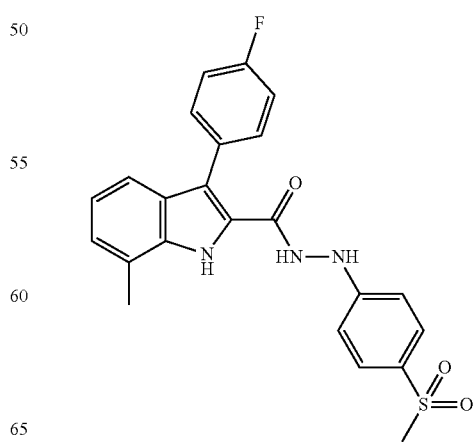

Example 111:
1-methyl-3-phenyl-1H-indole-2-carboxylic acid

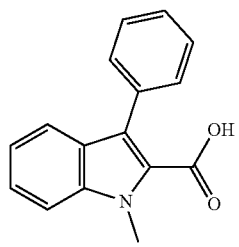 [SMILES: Cn1c(C(=O)O)c(-c2ccccc2)c2ccccc21]

Example 112:
7-fluoro-3-(4-fluorophenyl)-1H-indole-2-carboxylic acid

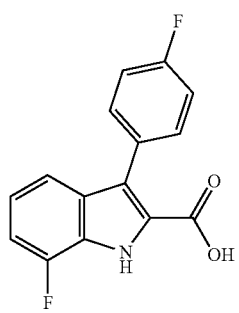 [SMILES: O=C(O)c1[nH]c2c(F)cccc2c1-c1ccc(F)cc1]

Example 113: N'-(4-(methylsulfonyl)phenyl)-3-phenyl-1H-indole-2-carbohydrazide

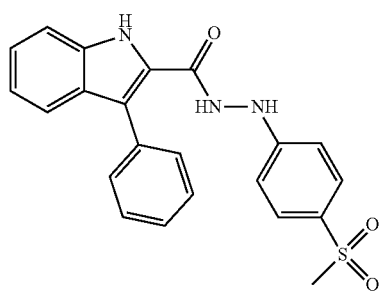 [SMILES: CS(=O)(=O)c1ccc(NNC(=O)c2[nH]c3ccccc3c2-c2ccccc2)cc1]

Example 114: 7-methyl-1H-indole-2-carboxylic acid

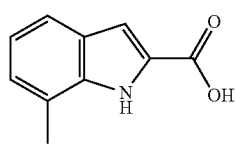

Example 115:
3-bromo-7-methyl-1H-indole-2-carboxylic acid

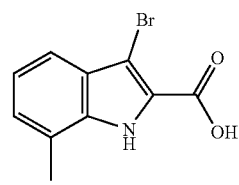

Example 116: 3-(2,3-dimethoxyphenyl)-7-methyl-1H-indole-2-carboxylic acid

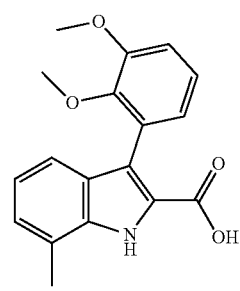 [SMILES: COc1cccc(-c2c(C(=O)O)[nH]c3c(C)cccc23)c1OC]

Example 117: 3-(3,5-dimethylisoxazol-4-yl)-7-methyl-1H-indole-2-carboxylic acid

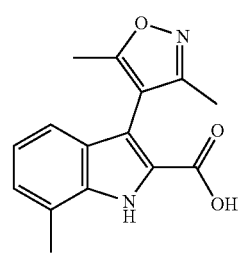 [SMILES: Cc1noc(C)c1-c1c(C(=O)O)[nH]c2c(C)cccc12]

Example 118: 7-methyl-3-(piperidin-4-yl)-1H-indole-2-carboxylic acid

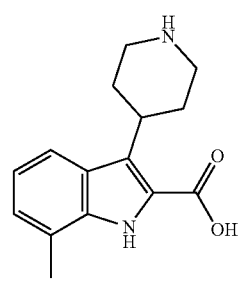 [SMILES: Cc1cccc2c(C3CCNCC3)c(C(=O)O)[nH]c12]

Example 119:
3-(4-fluorophenyl)-6-methyl-1H-indole-2-carboxylic acid

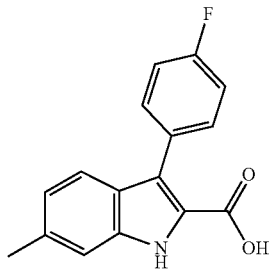 [SMILES: Cc1ccc2c(-c3ccc(F)cc3)c(C(=O)O)[nH]c2c1]

Example 120:
1-(4-fluorophenyl)-4-methyl-1H-indole-2-carboxylic acid

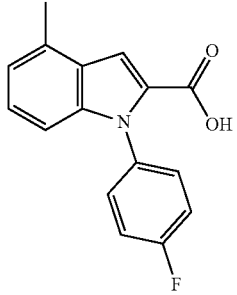 [SMILES: Cc1cccc2c1cc(C(=O)O)n2-c1ccc(F)cc1]

Example 121:
3-(4-fluorophenyl)-5-methyl-1H-indole-2-carboxylic acid

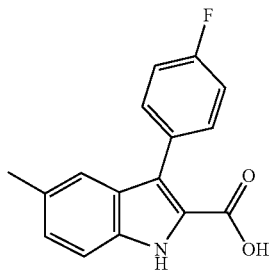 [SMILES: Cc1ccc2[nH]c(C(=O)O)c(-c3ccc(F)cc3)c2c1]

Example 122: 3-(4-(N,N-dimethylsulfamoyl)phenyl)-7-isopropyl-N-methyl-1H-indole-2-carboxamide

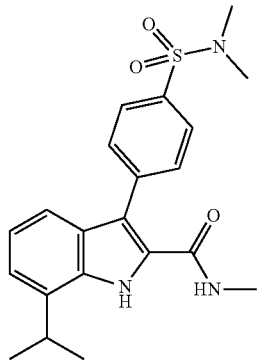 [SMILES: CNC(=O)c1[nH]c2c(C(C)C)cccc2c1-c1ccc(S(=O)(=O)N(C)C)cc1]

Example 123: 3-(4-(N,N-dimethylsulfamoyl)phenyl)-N,7-diisopropyl-1H-indole-2-carboxamide

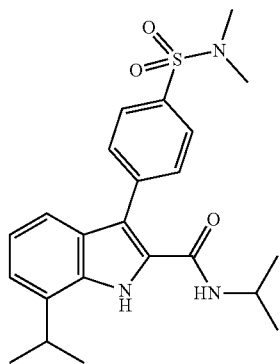 [SMILES: CC(C)NC(=O)c1[nH]c2c(C(C)C)cccc2c1-c1ccc(S(=O)(=O)N(C)C)cc1]

Example 124: 3-(4-(N,N-dimethylsulfamoyl)phenyl)-7-isopropyl-N-(thiazol-2-yl)-1H-indole-2-carboxamide

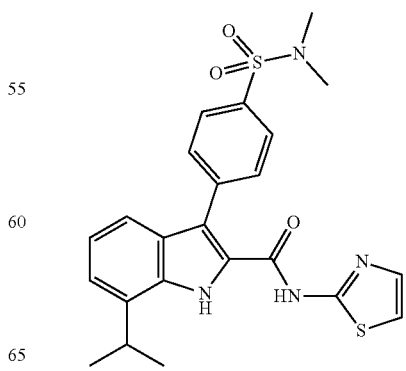

Example 125: 3-(4-(N,N-dimethylsulfamoyl)phe-
nyl)-7-isopropyl-1H-indole-2-carboxamide

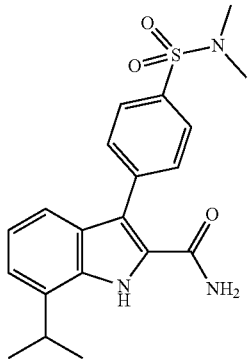 [SMILES: CC(C)c1cccc2c(-c3ccc(S(=O)(=O)N(C)C)cc3)c(C(N)=O)[nH]c12]

Example 126: 4-(2-cyano-7-isopropyl-1H-indol-3-yl)-N,N-dimethylbenzenesulfonamide

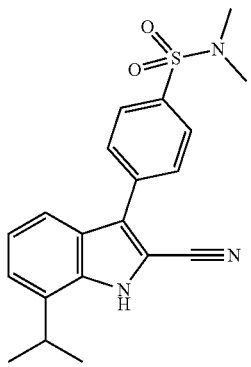 [SMILES: CC(C)c1cccc2c(-c3ccc(S(=O)(=O)N(C)C)cc3)c(C#N)[nH]c12]

Example 127: 3-(4-(N,N-dimethylsulfamoyl)phe-
nyl)-7-isopropyl-N-phenyl-1H-indole-2-carboxam-
ide

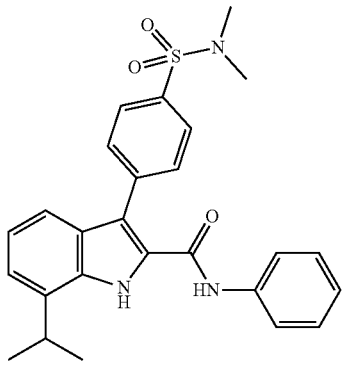 [SMILES: CC(C)c1cccc2c(-c3ccc(S(=O)(=O)N(C)C)cc3)c(C(=O)Nc3ccccc3)[nH]c12]

Example 128: 3-(4-(N,N-dimethylsulfamoyl)phe-
nyl)-7-isopropyl-N-(oxazol-2-yl)-1H-indole-2-car-
boxamide

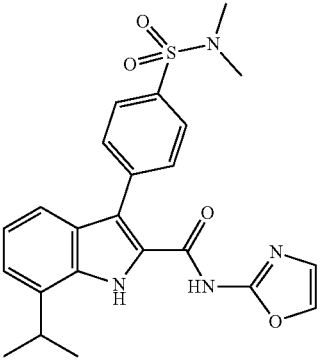 [SMILES: CC(C)c1cccc2c(-c3ccc(S(=O)(=O)N(C)C)cc3)c(C(=O)Nc3ncco3)[nH]c12]

The various functional groups and substituents making up the compounds of the formula I are typically chosen such that the molecular weight of the compound of the formula I does not exceed 1000. More usually, the molecular weight of the compound will be less than 900, for example less than 800, or less than 700, or less than 650, or less than 600. More preferably, the molecular weight is less than 550 and, for example, is 500 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn-Ingold-Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the formula I may exist in solvated as well as unsolvated forms such as, for example, hydrated forms. It is to be understood that the invention encompasses all such solvated forms that possess antiproliferative activity.

It is also to be understood that certain compounds of the formula I may exhibit polymorphism, and that the invention encompasses all such forms that possess antiproliferative activity.

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

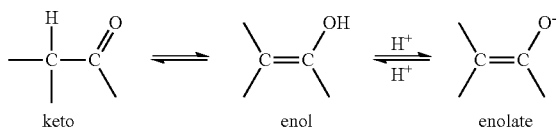

Compounds of the formula I containing an amine function may also form N-oxides.

A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);

b) Design of Pro-drugs, edited by H. Bundgaard, (Elsevier, 1985);

c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, *Advanced Drug Delivery Reviews*, 8, 1-38 (1992);

e) H. Bundgaard, et al., *Journal of Pharmaceutical Sciences*, 77, 285 (1988);

f) N. Kakeya, et al., *Chem. Pharm. Bull.*, 32, 692 (1984);

g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethylesters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula I will vary depending on the nature of $A_1$, $A_2$, $A_3$, $A_4$, $R_1$, $R_2$, $R_3$, $R_4$, $R_5$, $R_6$, $R_7$ and any substituent groups associated therewith. Suitable processes for their preparation are described further in the accompanying Examples.

Once a compound of formula I has been synthesised by any one of the processes defined herein, the processes may then further comprise the additional steps of:
(i) removing any protecting groups present;
(ii) converting the compound formula I into another compound of formula I;
(iii) forming a pharmaceutically acceptable salt, hydrate or solvate thereof; and/or
(iv) forming a prodrug thereof.

An example of (ii) above is when a compound of formula I is synthesised and then one or more of the groups $A_1$, $A_2$, $A_3$, $A_4$, $R_1$, $R_2$, $R_3$, $R_4$, $R_5$, $R_6$ and $R_7$, may be further reacted to change the nature of the group and provide an alternative compound of formula I. For example, the compound can be reacted to covert $R_1$ into a substituent group other than hydrogen.

The resultant compounds of formula I can be isolated and purified using techniques well known in the art.

Biological Activity

The enzyme and in-vitro cell-based assays described in accompanying Example section, or elsewhere in the literature, may be used to measure the pharmacological effects of the compounds of the present invention.

Although the pharmacological properties of the compounds of formula I vary with structural change, as expected, the compounds of the invention were found to be active in these enzyme assays.

The compounds of the invention demonstrate a $pIC_{50}$ of 4 or more in the enzyme assays described herein, with preferred compounds of the invention demonstrating an $pIC_{50}$ of 4.5 or more and the most preferred compounds of the invention demonstrating an $pIC_{50}$ of 5 or more.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier. For example, solid oral forms may contain, together with the active compound, diluents, such as, for example, lactose, dextrose, saccharose, cellulose, corn starch or potato starch; lubricants, such as, for example, silica, talc, stearic acid, magnesium or calcium stearate, and/or polyethylene glycols; binding agents; such as, for example, starches, arabic gums, gelatin, methylcellulose, carboxymethylcellulose or polyvinyl pyrrolidone; disaggregating agents, such as, for example, starch, alginic acid, alginates or sodium starch glycolate; effervescing mixtures; dyestuffs; sweeteners; wetting agents, such as, for example, lecithin, polysorbates, laurylsulphates; and, in general, non toxic and pharmacologically inactive substances used in pharmaceutical formulations. Such pharmaceutical compositions may be manufactured in by conventional methods known in the art, such as, for example, by mixing, granulating, tableting, sugar coating, or film coating processes.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). Suitably, oral or parenteral administration is preferred. Most suitably, oral administration is preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the condition, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the present invention are inhibitors of metallo-beta-lactamases (MBLs). Many bacteria have developed resistance to β-lactam antibacterials (BLAs) and one of the main resistance mechanisms is the hydrolysis of BLAs by MBLs. Thus, the inhibition of bacterial MBLs by the compounds of the present invention can significantly enhance the activity of BLAs, when administered with a compound of the present invention.

The present invention provides compounds that function as inhibitors of metallo-beta-lactamases.

The present invention therefore provides a method of inhibiting bacterial metallo-beta-lactamase activity in vitro or in vivo, said method comprising contacting a cell with an effective amount of a compound, or a pharmaceutically acceptable salt, hydrate or solvate thereof, or a pharmaceutical composition as defined herein.

The present invention also provides a method for the prevention or treatment of bacterial infection in a patient in need of such treatment, said method comprising administering to said patient a therapeutically effective amount of a compound, or a pharmaceutically acceptable salt, hydrate or solvate thereof, or a pharmaceutical composition as defined herein, in combination with a suitable antibacterial agent.

In a preferred embodiment, the antibacterial agent is a β-lactam antibacterial agent, or analogue thereof. Non limiting examples of suitable β-lactam antibacterial agents include carbapenems (e.g. meropenem, faropenem, imipenem, ertapenem, doripenem, panipenem/betamipron and biapenem as well as razupenem, tebipenem, lenapenem and tomopenem), ureidopenicillins (e.g. piperacillin), carbacephems (e.g. loracarbef) and cephalosporins (e.g. cefpodoxime, ceftazidime, cefotaxime, ceftriaxone, ceftobiprole, and ceftaroline). Specific examples of suitable β-lactam antibacterial agents include, for example, temocillin, piperacillin, cefpodoxime, ceftazidime, cefotaxime, ceftriaxone, meropenem, faropenem, imipenem, loracarbef, ceftobiprole and ceftaroline.

The present invention also provides a method of inhibiting bacterial infection, in vitro or in vivo, said method comprising contacting a cell with an effective amount of a compound, or a pharmaceutically acceptable salt, hydrate or solvate thereof, as defined herein, in combination with a suitable antibacterial agent.

The present invention also provides a compound, or a pharmaceutically acceptable salt, hydrate or solvate thereof, or a pharmaceutical composition as defined herein for use in therapy.

The present invention also provides a compound, or a pharmaceutically acceptable salt, hydrate or solvate thereof, or a pharmaceutical composition as defined herein for use in the treatment of a bacterial infection. In one embodiment, the treatment may be prophylactic (i.e. intended to prevent disease).

The present invention provides a compound, or a pharmaceutically acceptable salt, hydrate or solvate thereof, as defined herein for use in the inhibition of metallo-beta-lactamase activity.

Furthermore, the present invention provides a compound, or a pharmaceutically acceptable salt, hydrate or solvate thereof, as defined herein for use in the treatment of a disease or disorder in which metallo-beta-lactamase activity is implicated.

The present invention also provides a kit of parts comprising a compound, or a pharmaceutically acceptable salt, hydrate or solvate thereof, or a pharmaceutical composition as defined herein, and a BLA and/or a BLA linked to a formula (I) compound.

The term "bacterial infection" will be understood to refer to the invasion of bodily tissue by any pathogenic microorganisms that proliferate, resulting in tissue injury that can progress to disease. Suitably, the pathogenic microorganism is a bacteria.

The bacterial infection may be caused by Gram-negative or Gram-positive bacteria.

For example, the bacterial infection may be caused by bacteria from one or more of the following families; *Clostridium, Pseudomonas, Escherichia, Klebsiella, Enterococcus, Enterobacter, Serratia, Stenotrophomonas, Aeromonas, Morganella, Yersinia, Salmonella, Proteus, Pasteurella, Haemophilus, Citrobacter, Burkholderia, Brucella, Moraxella, Mycobacterium, Streptococcus* or *Staphylococcus*. Particular examples include *Clostridium, Pseudomonas, Escherichia, Klebsiella, Enterococcus, Enterobacter,* *Streptococcus* and *Staphylococcus*. The bacterial infection may, for example, be caused by one or more bacteria selected from *Moraxella catarrhalis, Brucella abortus, Burkholderia cepacia, Citrobacter species, Escherichia coli, Haemophilus pneumonia, Klebsiella Pneumonia, Pasteurella multocida, Proteus mirabilis, Salmonella typhimurium, Clostridium difficile, Yersinia enterocolitica Mycobacterium tuberculosis, Staphylococcus aureus*, group B streptococci, *Streptococcus Pneumonia*, and *Streptococcus pyogenes*, e.g. from *E. coli* and *K. pneumoniae*.

It will be understood by a person skilled in the art that the patient in need thereof is suitably a human, but may also include, but is not limited to, primates (e.g. monkeys), commercially farmed animals (e.g. horses, cows, sheep or pigs) and domestic pets (e.g. dogs, cats, guinea pigs, rabbits, hamsters or gerbils). Thus the patient in need thereof may be any mammal that is capable of being infected by a bacterium.

Routes of Administration

The compounds of the present invention, or pharmaceutical compositions comprising these compounds, may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Diagnostic Uses

The compounds of the present invention, or pharmaceutical compositions comprising these compounds in combination with a suitable antibacterial agent, may also be used in methods for the detection of metallo-beta-lactamases. It will be appreciated that the compounds of formula (I) may be modified to enable various types of assays known is the literature, such as those using spectroscopic such as fluorescence or luminescence based methods. Thus, in one variation a sample containing bacteria which is suspected of expressing MBLs can be cultured (a) in the presence of a beta-lactam antibiotic agent; and (b) in the presence of the antibiotic combination of the invention. If the bacteria are seen to grow under conditions (a), this suggests that a beta-lactamase, able to hydrolyse the antibiotic agent, is causing resistance of the bacteria to the antibiotic agent. However, if the bacteria do not grow under condition (b), i.e. in the presence of compound of the present invention and a suitable antibacterial agent, then the beta-lactamases present have been inhibited. Such a result suggests that the beta-lactamases are metallo-beta-lactamases. The method can be used to determine whether bacteria express metallo-beta-lactamase enzymes.

EXAMPLES

Abbreviations

BLA β-Lactam antibacterials
ca. circa (about)
DCM Dichloromethane
DIAD Diisopropyl azodicarboxylate DMF Dimethylformamide
DMSO Dimethylsulfoxide
dppf 1,1'-Bis(diphenylphosphino)ferrocene
EDC 1-Ethyl-3-(3-dimethylaminopropyl)carbodiimide
ESI Electrospray ionization
HOBt Hydroxybenzotriazole
HPLC High performance liquid chromatography
IMP-1 Imipenemase-1
LCMS Liquid chromatography-mass spectrometry
MBL Metallo-beta-lactamase
MIC Minimum inhibitory concentration
MS Molecular sieves
m/z Mass/charge
NDM-1 New Delhi Metallo-beta-lactamase-1
NIS N-Iodosuccinimide
NMR Nuclear Magnetic Resonance
PTSA p-Toluenesulfonic acid
ppm parts per million
RT Retention time
rt Room temperature
SCX-2 Strong cation exchange (Si-Propylsulfonic acid)
TEA Triethylamine
THF Tetrahydrofuran
UV Ultraviolet
VIM Veronese metallo-β-lactamase
NDM New Delhi metallo-β-lactamase
IMP-1 Imipenemase-1
Materials and Methods Standard experimental procedures were followed for synthesis; some of these are defined below.

Chemicals and solvents were from commonly used suppliers and were used without further purification. Silica gel 60 F254 analytical thin layer chromatography (TLC) plates were from Merck (Darmstadt, Germany) and visualized under UV light and/or with potassium permanganate stain. Chromatographic purifications were performed using Merck Geduran 60 silica (40-63 μm) or prepacked SNAP columns using a Biotage SP1 Purification system (Uppsala, Sweden). Microwave assisted reactions were performed using a Biotage Initiator™ microwave synthesizer in sealed vials. Deuterated solvents were obtained from Cambridge Isotopes, Sigma-Aldrich, Goss Scientific Instruments Ltd. and Apollo Scientific Ltd. All $^1$H and $^{13}$C NMR spectra were recorded using a Bruker Avance 400 MHz spectrometer. All chemical shifts are given in ppm relative to the solvent peak, and coupling constants (J) are reported in Hz. High Resolution (HR) mass spectrometry data (m/z) were obtained from a Bruker MicroTOF instrument using an ESI source and Time of Flight (TOF) analyzer. Low Resolution (LR) mass spectrometry data (m/z) were obtained from a Waters LCT Premier instrument using an ESI source and Time of Flight (TOF) analyzer or an Agilent 6140 series Quadrupole Mass Spectrometer with a multimode source attached to an Agilent 1200 series HPLC. Melting points were obtained using a Stuart SMP-40 automatic melting point apparatus.

LCMS Analytical Methods

Analytical Method A

LCMS was performed using an Agilent 6140 Series Quadrupole Mass Spectrometer with a multimode source. Analysis was performed using either a Phenomenex Luna® C18 (2)-HST column (2.5 μm, 50×2.0 mm) or a Waters X-select® CSH™ C18 column (2.5 μm, 50×2.1 mm). Mobile phase A contained 0.1% formic acid in 18 MO water and mobile phase B contained 0.1% formic acid in HPLC grade acetonitrile. A flow rate of 1.00 ml min$^{-1}$ was used over a 3.75 min gradient starting with 99% mobile phase A gradually increasing to 100% mobile phase B. The samples were monitored at 254 nm.

Analytical Method B

LCMS was performed using an Agilent 6140 Series Quadrupole Mass Spectrometer with a multimode source. Analysis was performed using either a Phenomenex Luna® C18 (2)-HST column (2.5 μm, 50×2.0 mm) or a Waters X-select® CSH™ C18 column (2.5 μm, 50×2.1 mm). Mobile phase A contained 0.1% formic acid in 18 MO water and mobile phase B contained 0.1% formic acid in HPLC grade acetonitrile. A flow rate of 1.00 ml min$^{-1}$ was used over a 5.5 min gradient starting with 99% mobile phase A gradually increasing to 100% mobile phase B. The samples were monitored at 254 nm.

Preparative HPLC Method

Preparative HPLC was carried out on Waters HPLC comprising of a Waters 2767 Sample Manager, Waters 2545 Binary Gradient Module, Waters Systems Fluidics Organiser, Waters 515 ACD pump, Waters 2998 Photodiode Array Detector, using a Waters XBridge Prep OBD C18, 5 μm, 19 mm×50 mm i.d. column and a flow rate of 20 mL/minute. The general method that may be used to purify compounds are: acidic reverse phase HPLC (water/acetonitrile/0.1% trifluoroacetic acid) using a standard gradient of 5% acetonitrile/95% water to 100% acetonitrile or basic reverse phase HPLC (water/acetonitrile/0.01 M ammonia solution) using a standard gradient of 10% acetonitrile/90% water to 100% acetonitrile. UV detection e.g. 254 nM is used for the collection of fractions from HPLC. This description gives general methods and variations in types of equipment, columns, mobile phase, detection wavelength, solvent gradient and run time may also be used to purify compounds.

Procedures for Synthesis

General Procedure A

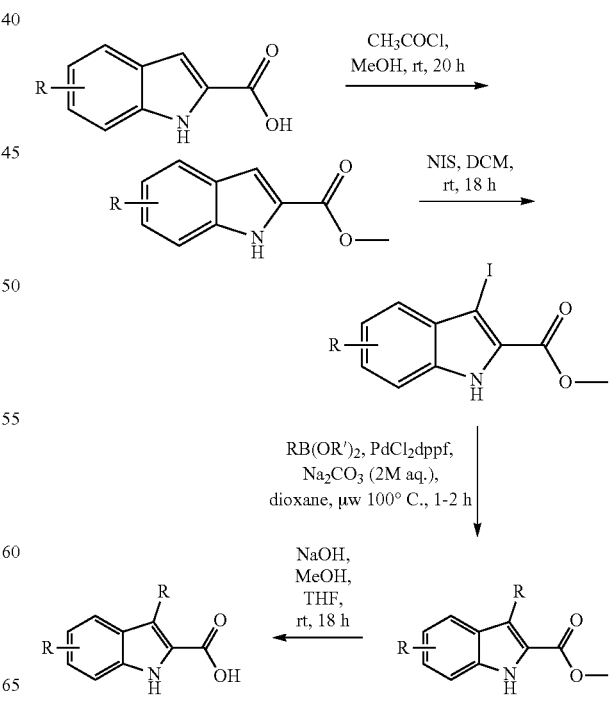

Example 1—3-(3-chlorophenyl)-7-methyl-1H-indole-2-carboxylic acid

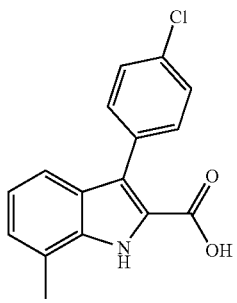 [SMILES: Cc1cccc2c(-c3ccc(Cl)cc3)c(C(=O)O)[nH]c12]

i) Preparation of 7-methyl-1H-indole-2-carboxylate

To a cooled (0° C.) flask of methanol (3 mL) under argon was added dropwise acetyl chloride (1.14 ml, 15.98 mmol). 7-methyl-1H-indole-2-carboxylic acid (1 g, 5.71 mmol) was treated with the resulting HCl in methanol solution at room temperature for 20 h. After this time, the mixture had become a thick suspension and was concentrated under reduced pressure, azeotroping with toluene and used without any further purification.

$^1$H NMR (400 MHz, METHANOL-d4) δ ppm 7.42-7.48 (1H, m) 7.14-7.19 (1H, m) 7.02-7.07 (1H, m) 6.95-7.01 (1H, m) 3.92 (3H, s) 2.52 (3H, s).

ii) Preparation of methyl 3-iodo-7-methyl-1H-indole-2-carboxylate

To a solution of methyl 7-methyl-1H-indole-2-carboxylate (1 g, 5.29 mmol) in DCM (16 mL) was added N-Iodosuccinimide (1.19 g, 5.29 mmol). The resulting mixture was stirred at room temperature for 64 h then partitioned between DCM and NaHCO₃. The aqueous phase was further washed with DCM and the combined organic extracts washed with brine, dried over Na₂SO₄, filtered and concentrated under reduced pressure. The resulting material was subjected to flash chromatography (SNAP-50g, EtOAc in heptane, 0-20%) to give a yellow solid consistent with the title compound.

$^1$H NMR (400 MHz, CHLOROFORM-d) δ ppm 9.08 (1H, br. s.) 7.40-7.48 (1H, m) 7.11-7.24 (2H, m) 3.99-4.06 (3H, m) 2.55 (3H, s).

(iii) Preparation of methyl 3-(4-chlorophenyl)-7-methyl-1H-indole-2-carboxylate

A mixture of methyl 3-iodo-7-methyl-1H-indole-2-carboxylate (100 mg, 0.32 mmol), (4-chlorophenyl)boronic acid (49.63 mg, 0.32 mmol), 2M Na₂CO₃ (0.63 ml) and Pd(dppf)Cl₂ (11.61 mg, 0.02 mmol) in dioxane (2.8 mL) was purged with argon then subjected to microwave irradiation at 100° C. for 1 h. The resulting mixture was filtered over celite, rinsing with EtOAc and water. The filtrate was partitioned between 1M HCl and EtOAc. The organic extracts were washed with brine, dried over Na₂SO₄, filtered and concentrated under reduced pressure. The residue was taken up in DCM, adsorbed onto silica and subjected to flash chromatography (SNAP-10g, DCM in heptane, 0-50%) to give the title compound.

$^1$H NMR (400 MHz, CHLOROFORM-d) δ ppm 8.90 (1H, br. s.) 7.42-7.54 (4H, m) 7.05-7.23 (2H, m) 3.80-3.91 (3H, m) 2.54-2.62 (3H, m).

iv) Preparation of 3-(4-chlorophenyl)-7-methyl-1H-indole-2-carboxylic acid

To a mixture of methyl 3-(4-chlorophenyl)-7-methyl-1H-indole-2-carboxylate (86 mg, 0.29 mmol) in THF (2 mL) and methanol (0.9 mL) was added 2M NaOH (0.72 ml). The resulting mixture was stirred at room temperature for 24 h. The mixture was treated with 1M HCl (ca. 2 mL) then concentrated to remove organic solvent. The resulting suspension was filtered and dried under vacuum at 55° C. to give the title compound.

LCMS Method B: RT=3.22 min, m/z 284.00.

Using the above general procedure the following compounds were prepared:

| Example Number | Structure | Analytical Method | Retention Time (mins) | m/z |
|---|---|---|---|---|
| 1 | 3-(3-chlorophenyl)-7-methyl-1H-indole-2-carboxylic acid | B | 3.25 | 284.00 |
| 2 | 7-methyl-3-(4-(trifluoromethoxy)phenyl)-1H-indole-2-carboxylic acid | B | 3.37 | 334.00 |
| 3 | 3-(3,5-dichlorophenyl)-7-methyl-1H-indole-2-carboxylic acid | B | 3.45 | 318.00 |

| Example Number | Structure | Analytical Method | Retention Time (mins) | m/z |
|---|---|---|---|---|
| 4 | 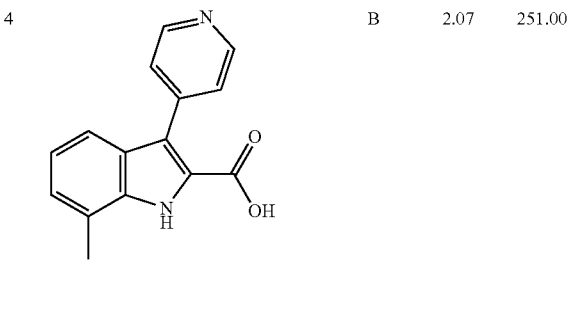 | B | 2.07 | 251.00 |
| 5 | 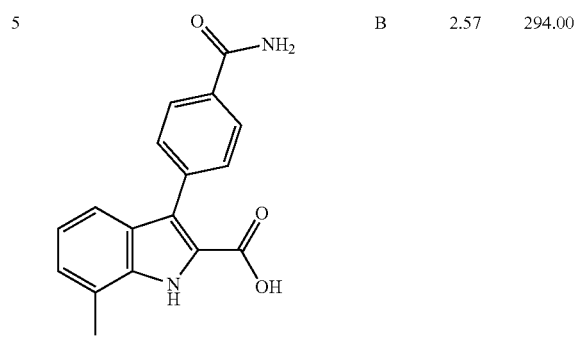 | B | 2.57 | 294.00 |
| 6 | 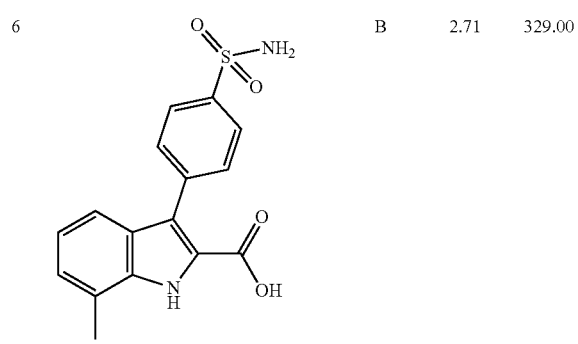 | B | 2.71 | 329.00 |
| 7 | 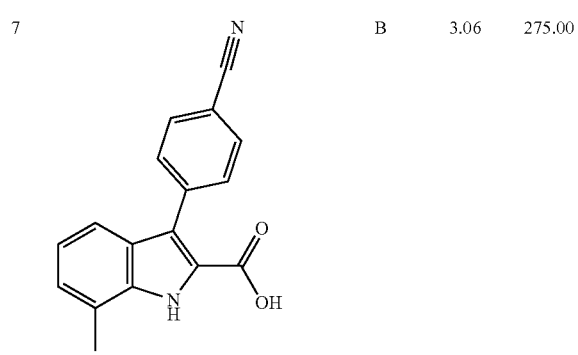 | B | 3.06 | 275.00 |
| 8 | 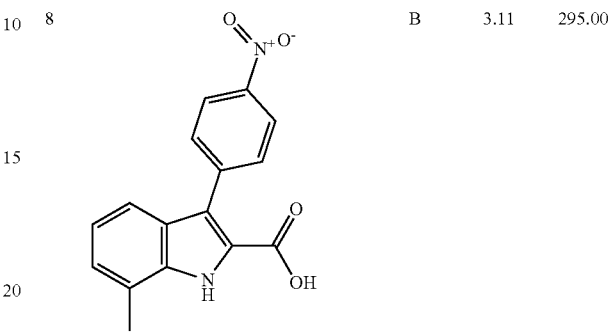 | B | 3.11 | 295.00 |
| 9 | 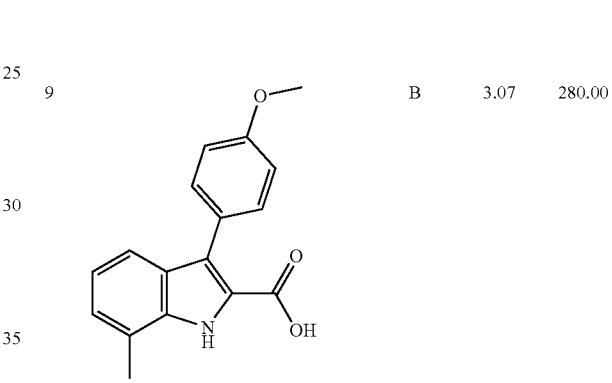 | B | 3.07 | 280.00 |
| 10 | 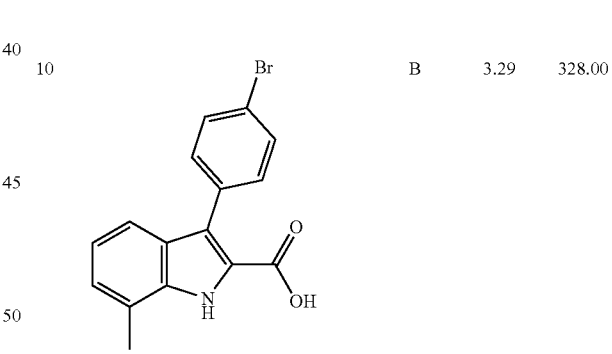 | B | 3.29 | 328.00 |
| 11 | 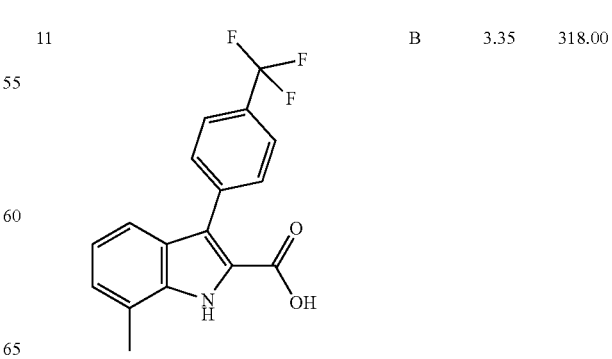 | B | 3.35 | 318.00 |

| Example Number | Structure | Analytical Method | Retention Time (mins) | m/z |
|---|---|---|---|---|
| 12 | 3-(4-methylsulfonylphenyl)-7-methyl-1H-indole-2-carboxylic acid | B | 2.79 | 328.00 |
| 13 | 3-(4-morpholinophenyl)-7-methyl-1H-indole-2-carboxylic acid | B | 2.93 | 337.05 |
| 14 | 3-(3-sulfamoylphenyl)-7-methyl-1H-indole-2-carboxylic acid | B | 2.74 | 329.00 |
| 15 | 3-(3-nitrophenyl)-7-methyl-1H-indole-2-carboxylic acid | B | 3.09 | 295.00 |
| 16 | 3-(3-methylsulfonylphenyl)-7-methyl-1H-indole-2-carboxylic acid | B | 2.8 | 328.00 |
| 17 | 3-(3-dimethylaminophenyl)-7-methyl-1H-indole-2-carboxylic acid | B | 2.45 | 295.05 |
| 18 | 3-(3-bromophenyl)-7-methyl-1H-indole-2-carboxylic acid | B | 3.27 | 328.00 |
| 19 | 3-(1H-indazol-5-yl)-7-methyl-1H-indole-2-carboxylic acid | B | 2.79 | 290.00 |
| 20 | 3-(2-methoxyphenyl)-7-methyl-1H-indole-2-carboxylic acid | B | 3.00 | 280.00 |

-continued

| Example Number | Structure | Analytical Method | Retention Time (mins) | m/z |
|---|---|---|---|---|
| 21 | [1,2,4]triazolo[1,5-a]pyridin-6-yl substituted 7-methyl-1H-indole-2-carboxylic acid | B | 2.59 | 293.10 |
| 22 | pyrimidin-5-yl substituted 7-methyl-1H-indole-2-carboxylic acid | B | 2.50 | 254.10 |
| 23 | 3-(4-aminophenyl)-7-methyl-1H-indole-2-carboxylic acid | B | 2.29 | 267.05 |
| 24 | 7-methyl-3-(pyridin-3-yl)-1H-indole-2-carboxylic acid | B | 2.08 | 253.05 |
| 25 | tert-butyl 4-(2-carboxy-7-methyl-1H-indol-3-yl)-3,6-dihydropyridine-1(2H)-carboxylate | B | 3.24 | 355.20 |
| 26 | 7-methyl-3-(1-methyl-1H-pyrazol-4-yl)-1H-indole-2-carboxylic acid | B | 1.92 | 256.20 |
| 27 | 3-(cyclopent-1-en-1-yl)-7-methyl-1H-indole-2-carboxylic acid | B | 3.15 | 242.20 |
| 28 | 3-(2-cyanophenyl)-7-methyl-1H-indole-2-carboxylic acid | B | 2.8 | 277.20 |
| 29 | 3-(4-(N,N-dimethylsulfamoyl)phenyl)-7-methyl-1H-indole-2-carboxylic acid | B | 2.85 | 359.20 |

| Example Number | Structure | Analytical Method | Retention Time (mins) | m/z |
|---|---|---|---|---|
| 30 | 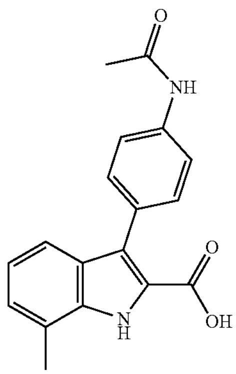 [SMILES: CC(=O)Nc1ccc(-c2c(C(=O)O)[nH]c3c(C)cccc23)cc1] | B | 2.56 | 309.20 |
| 31 | 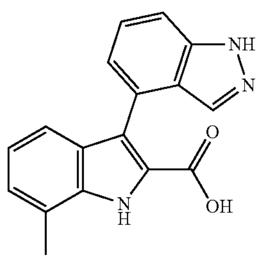 [SMILES: Cc1cccc2c(-c3cccc4[nH]ncc34)c(C(=O)O)[nH]c12] | B | 2.64 | 290.20 |
| 32 | 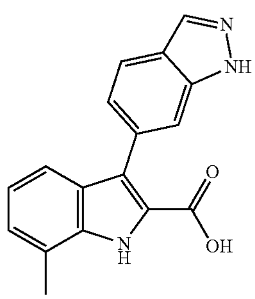 [SMILES: Cc1cccc2c(-c3ccc4cn[nH]c4c3)c(C(=O)O)[nH]c12] | B | 2.69 | 290.20 |
| 33 | 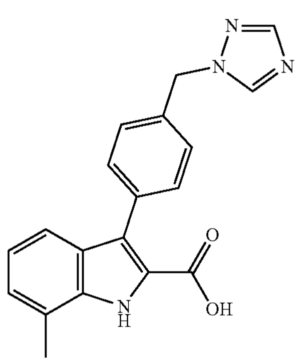 [SMILES: Cc1cccc2c(-c3ccc(Cn4cncn4)cc3)c(C(=O)O)[nH]c12] | B | 2.61 | 333.20 |
| 34 | | B | 2.85 | 332.20 |

Example 35

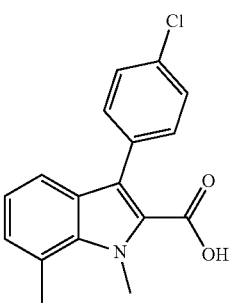 [SMILES: Cc1cccc2c(-c3ccc(Cl)cc3)c(C(=O)O)n(C)c12]

i) Preparation of 3-(4-chlorophenyl)-1,7-dimethyl-indole-2-carboxylic acid

To a solution of 3-(4-chlorophenyl)-7-methyl-1H-indole-2-carboxylic acid (31.4 mg, 0.11 mmol) in THF (1.5 mL) was added NaH (60% dispersion in mineral oil, 8.79 mg, 0.22 mmol). Effervescence occurred upon addition and the mixture was stirred at room temperature for 5 minutes, prior to addition of $CH_3I$ (8.21 µl, 0.13 mmol), added as a solution in THF (100 µL) and stirred at room temperature for 24 hours. After this time the mixture was heated to reflux for 24 h. The mixture was cooled to room temperature and additional NaH (60%, 8.79 mg, 0.22 mmol) added. After 5 minutes, $CH_3I$ was added (4.1 µl, 0.07 mmol) in THF (50 µL). The mixture was heated for a further 23 h, then allowed to cool.

The residue was partitioned between 1M HCl and EtOAc. The organic extracts were washed with brine, dried over $Na_2SO_4$, filtered and concentrated under reduced pressure. The residue was taken up in DMSO/MeOH (1:1, 1 mL) and purified by preparative HPLC to give the title compound.

LCMS Method B: RT=3.32 min, m/z 300.20.

Example 36

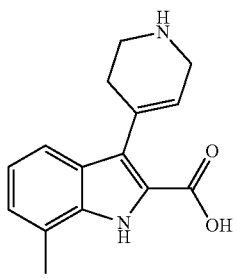 [SMILES: Cc1cccc2c(C3=CCNCC3)c(C(=O)O)[nH]c12]

i) Preparation of 7-methyl-3-(1,2,3,6-tetrahydropyridin-4-yl)-1H-indole-2-carboxylic acid To a suspension of 3-(1-tert-butoxycarbonyl-3,6-dihydro-2H-pyridin-4-yl)-7-methyl-1H-indole-2-carboxylic acid (50 mg, 0.14 mmol) in DCM (1 mL) was added TFA (0.4 mL). The mixture became a solution and was stirred at room temperature for 2 h then concentrated under reduced pressure. The residue was taken up in MeOH and loaded onto a 2 g SCX-2 cartridge. The cartridge was flushed with methanol then eluted with 2M $NH_3$ in MeOH. Basic fractions were combined and concentrated under reduced pressure and the resulting yellow glass dried under vacuum overnight at 60° C. to give the title compound.

LCMS Method B: RT=1.32 min, m/z 257.25.

General Procedure B

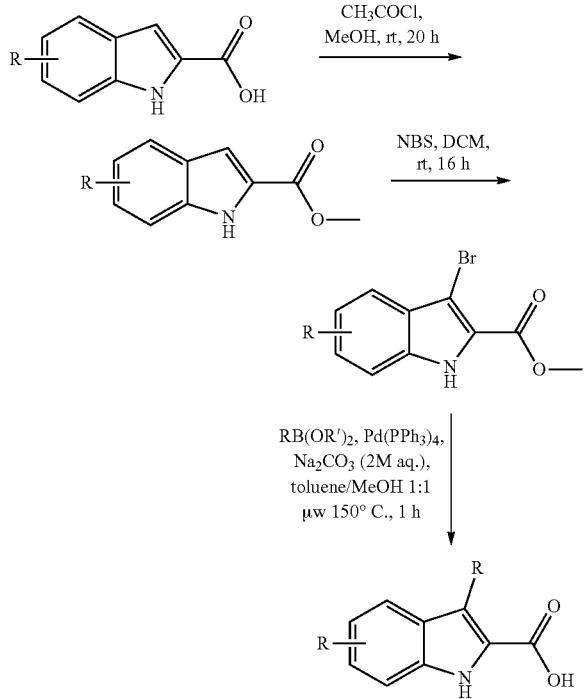

Example 37

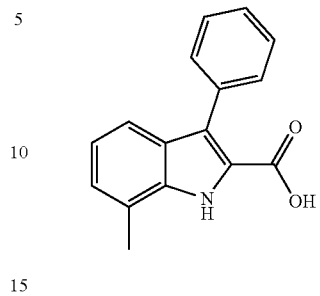

i) Preparation of methyl 3-bromo-7-methyl-1H-indole-2-carboxylate

To a solution of methyl 7-methyl-1H-indole-2-carboxylate (0.5 g, 2.64 mmol) in DCM (8 mL) was added NBS (0.52 g, 2.91 mmol). The resulting mixture was stirred at room temperature for 64 h then the mixture washed with sat. aq. $NaHCO_3$. The organic extracts were washed with brine, dried over $Na_2SO_4$, filtered and concentrated under reduced pressure to afford the title compound which was used without further purification.

1H NMR (400 MHz, CHLOROFORM-d) δ ppm 8.83-8.98 (1H, m) 7.49-7.58 (1H, m) 7.19 (2H, s) 3.96-4.08 (3H, m) 2.46-2.57 (3H, m).

ii) Preparation of 7-methyl-3-phenyl-1H-indole-2-carboxylate

A suspension of methyl 3-bromo-7-methyl-1H-indole-2-carboxylate (60 mg, 0.22 mmol), phenylboronic acid (40.93 mg, 0.34 mmol), Tetrakis(triphenylphosphine)palladium(0) (12.93 mg, 0.01 mmol) and 2M aq. $Na_2CO_3$ (0.45 ml) in methanol (1 mL) and toluene (1 mL) was subjected to microwave irradiation at 150° C. for 1 h. The mixture was filtered through Celite™, rinsing with EtOAc and water/1M HCl. The phases were separated and the aqueous phase further extracted with EtOAc. The combined organic extracts were washed with brine, dried over $Na_2SO_4$, filtered and concentrated under reduced pressure. The resulting material was subjected to flash chromatography (SNAP-10g, MeOH in DCM, 1-10%) followed by purification by preparative HPLC to give the title compound.

LCMS Method B: RT=2.30 min, m/z 252.15

Using the above general procedure the following compounds were prepared:

| Example Number | Structure | Analytical Method | Retention Time (mins) | m/z |
|---|---|---|---|---|
| 37 | 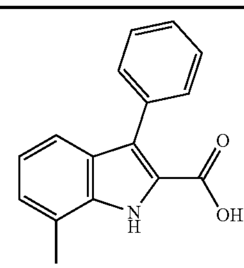 | B | 2.30 | 252.15 |

-continued
| Example Number | Structure | Analytical Method | Retention Time (mins) | m/z |
|---|---|---|---|---|
| 38 | 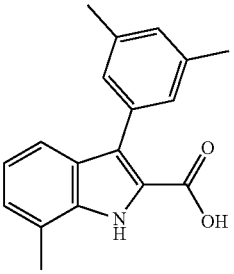 [SMILES: Cc1cc(C)cc(-c2c(C(=O)O)[nH]c3c(C)cccc23)c1] | B | 3.38 | 280.2 |
| 39 | 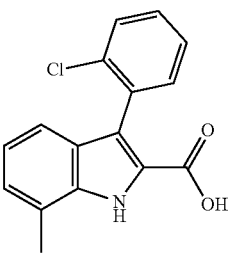 [SMILES: Cc1cccc2c(-c3ccccc3Cl)c(C(=O)O)[nH]c12] | B | 3.19 | 284.00 |
| 40 | 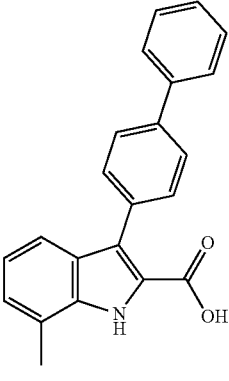 [SMILES: Cc1cccc2c(-c3ccc(-c4ccccc4)cc3)c(C(=O)O)[nH]c12] | B | 3.46 | 326.00 |
| 41 | 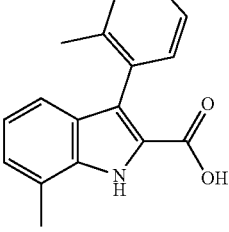 | B | 3.19 | 264.00 |
| 42 | 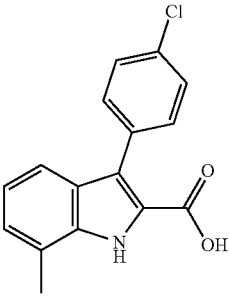 | B | 3.29 | 284.00 |
| 43 | 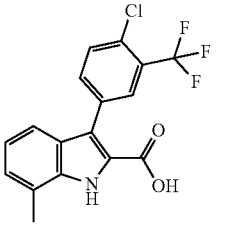 [SMILES: Cc1cccc2c(-c3ccc(Cl)c(C(F)(F)F)c3)c(C(=O)O)[nH]c12] | B | 3.44 | 352.00 |
| 44 | 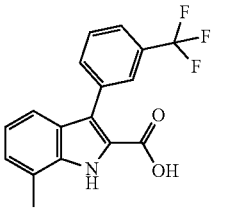 [SMILES: Cc1cccc2c(-c3cccc(C(F)(F)F)c3)c(C(=O)O)[nH]c12] | B | 3.36 | 318.00 |
| 45 | 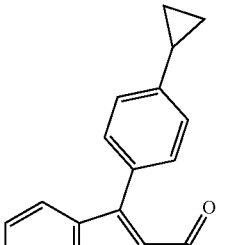 | B | 3.32 | 290.20 |
| 46 | 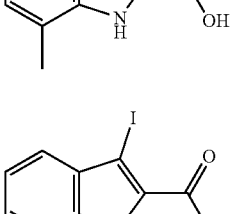 | B | 2.91 | 300.00 |
| 47 | 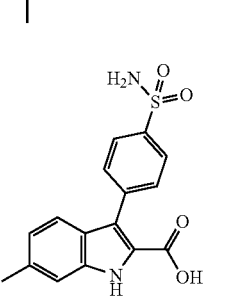 | B | 2.84 | 252.00 |
| 48 | 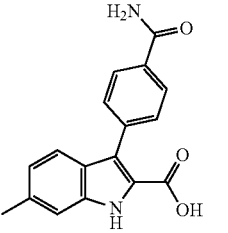 [SMILES: Cc1ccc2c(-c3ccc(C(N)=O)cc3)c(C(=O)O)[nH]c2c1] | B | 2.43 | 295.20 |

General Procedure C

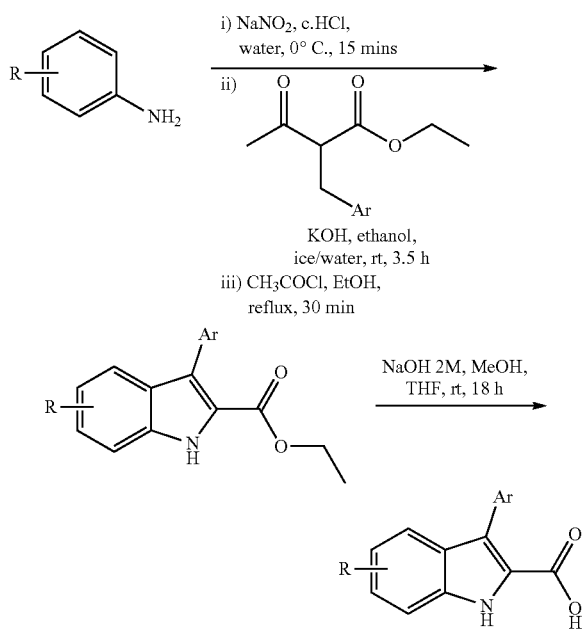

Example 49

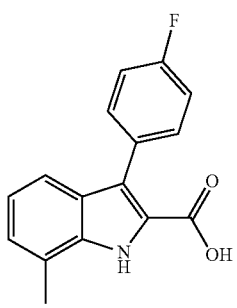 [SMILES: Cc1cccc2c(-c3ccc(F)cc3)c(C(=O)O)[nH]c12]

i) Preparation of ethyl 3-(4-fluorophenyl)-7-methyl-1H-indole-2-carboxylate

To a cooled (0° C.) suspension of 2-methylaniline (0.22 ml, 2.1 mmol) in 12M HCl (1.1 ml) (conc.) was added dropwise a solution of NaNO$_2$ (159.27 mg, 2.31 mmol) in water (0.95 mL). The resulting orange solution was stirred at 0° C. for 15 minutes then added dropwise to a prepared mixture of ethyl 2-[(4-fluorophenyl)methyl]-3-oxo-butanoate (500 mg, 2.1 mmol), KOH (412.09 mg, 7.35 mmol) and ice (2 g) in water (0.95 ml) and ethanol (2.4 mL). The resulting mixture was stirred at room temperature for 3.5 h then partitioned between EtOAc and water. The aqueous phase was further extracted with EtOAc and the combined organic extracts washed with brine, dried over Na$_2$SO$_4$, filtered and concentrated under reduced pressure. The resulting material was subjected to flash chromatography (25 g, EtOAc in heptane, 0-20%). Fractions corresponding to the main product were combined and concentrated under reduced pressure to afford a bright yellow oil. The oil was taken up in a HCl in ethanol solution (1.83 mL, prepared by adding 0.48 mL of acetyl chloride to 3.2 mL ethanol), and heated to reflux for 30 minutes. The mixture was cooled to room temperature and concentrated under reduced pressure then partitioned between water and EtOAc. The organic phase was washed with brine, dried over Na$_2$SO$_4$, filtered and concentrated under reduced pressure. The resulting material was subjected to flash chromatography (SNAP-10g, EtOAc in heptane, 0-20%) followed by repurification using (SNAP-10g, DCM in heptane, 0-50%) to give the title compound.

$^1$H NMR (400 MHz, CHLOROFORM-d) δ ppm 8.96 (1H, br. s.) 7.49-7.59 (2H, m) 7.45 (1H, d, J=8.28 Hz) 7.04-7.22 (4H, m) 4.25-4.38 (2H, m) 2.52-2.62 (3H, m) 1.21-1.31 (4H, m).

ii) Preparation of 3-(4-fluorophenyl)-7-methyl-1H-indole-2-carboxylic acid

A mixture of ethyl 3-(4-fluorophenyl)-7-methyl-1H-indole-2-carboxylate (128 mg, 0.43 mmol) and 6M NaOH (0.14 ml) was heated at 70° C. for 2.5 h. The mixture was concentrated under reduced pressure then the residue partitioned between EtOAc and water. The aqueous phase was further washed with EtOAc then acidified using 1 M HCl. The acidic aqueous phase was extracted with EtOAc (×3) and the combined organic extracts washed with brine, dried over Na$_2$SO$_4$, filtered and concentrated under reduced pressure. The resulting material was taken up in MeOH/DCM and subjected to flash chromatography (SNAP-25 g, EtOAc in DCM, 0-50%) and dried under vacuum at 50° C. to give the title compound.

LCMS Method B: RT=2.50 min, m/z 268.00.

Using the above general procedure the following compounds were prepared:

| Example Number | Structure | Analytical Method | Retention Time (mins) | m/z |
|---|---|---|---|---|
| 49 | 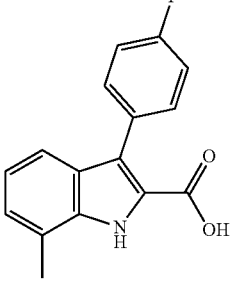 | B | 2.5 | 268.00 |
| 50 | 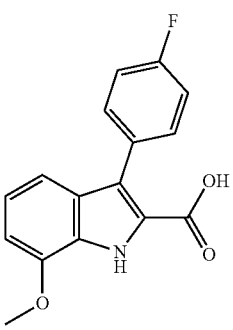 [SMILES: COc1cccc2c(-c3ccc(F)cc3)c(C(=O)O)[nH]c12] | B | 3.01 | 284.00 |

-continued

| Example Number | Structure | Analytical Method | Retention Time (mins) | m/z |
|---|---|---|---|---|
| 51 | 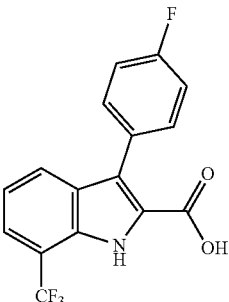 | B | 3.25 | 322.20 |
| 52 | 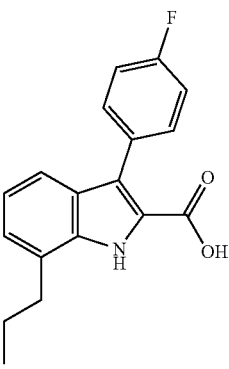 [SMILES: CCCc1cccc2c(-c3ccc(F)cc3)c(C(=O)O)[nH]c12] | B | 3.25 | 322.20 |
| 53 | 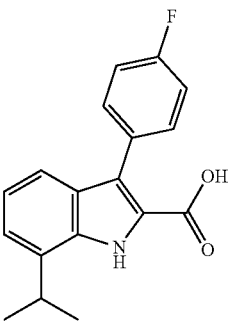 [SMILES: CC(C)c1cccc2c(-c3ccc(F)cc3)c(C(=O)O)[nH]c12] | B | 3.35 | 396.20 |
| 54 | 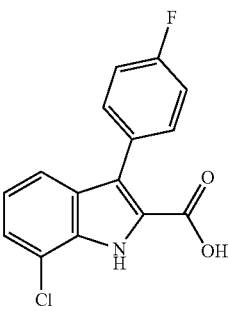 [SMILES: O=C(O)c1[nH]c2c(Cl)cccc2c1-c1ccc(F)cc1] | B | 3.15 | 288.00 |

General Procedure D

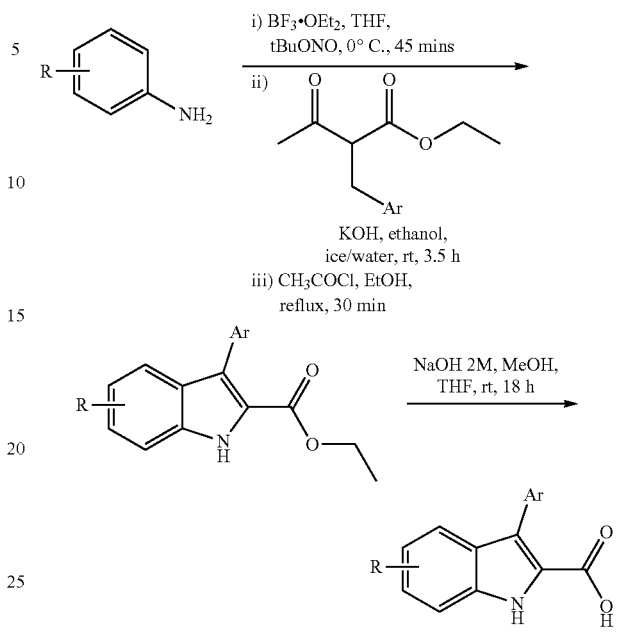

Example 55

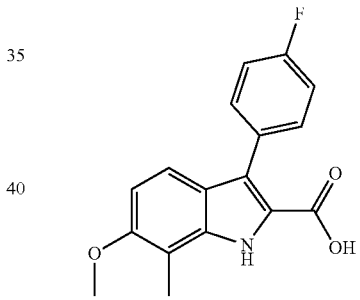

i) Preparation of ethyl 3-(4-fluorophenyl)-6-methoxy-7-methyl-1H-indole-2-carboxylate To a solution ethyl 2-[(4-fluorophenyl)methyl]-3-oxo-butanoate (500 mg, 2.1 mmol) in ethanol (5 mL) and water (1 mL) was added ice (ca. 2 g) followed by KOH (412.09 mg, 7.35 mmol). The resulting mixture was stirred at room temperature for 45 minutes then cooled to 0° C.

In a separate flask, to a cooled (0° C.) solution of 3-methoxy-2-methyl-aniline (431.83 mg, 3.15 mmol) in anhydrous THF (3 mL) was added dropwise $BF_3 \cdot OEt_2$ (0.58 ml, 4.72 mmol), followed by dropwise addition of tert-butyl nitrite (0.45 ml, 3.78 mmol). The resulting mixture was stirred at 0° C. for 45 minutes and then the thick red-brown suspension diluted with THF (2 mL) and added dropwise to the prepared enolate solution. The resulting mixture was stirred at room temperature for 2 h. The mixture was concentrated to remove organic solvent then partitioned between EtOAc and water. The aqueous phase was further extracted with EtOAc (×2) and the combined organic extracts washed with brine, dried over $Na_2SO_4$, filtered and concentrated under reduced pressure.

The resulting intermediate was taken up in a solution of ethanolic HCl (2:1 EtOH/AcCl, 9 ml) and then heated to reflux for 1.5 h. The mixture was concentrated under reduced pressure and the residue partitioned between EtOAc and sat. aq. NaHCO$_3$. The organic extracts were washed with brine, dried over Na$_2$SO$_4$, filtered and concentrated under reduced pressure. The residue was taken up in DCM, adsorbed onto silica and subjected to flash chromatography (Telos 12 g, DCM in heptane, 0-75%) followed by trituration in methanol to give the title compound.

$^1$H NMR (400 MHz, CHLOROFORM-d) δ ppm 8.68 (1H, br. s.) 7.48-7.58 (2H, m) 7.39 (1H, d, J=9.03 Hz) 7.10-7.21 (2H, m) 6.91 (1H, d, J=9.03 Hz) 4.24-4.36 (2H, m) 3.93 (3H, s) 2.42 (3H, s) 1.21-1.32 (3H, m).

ii) Preparation of 3-(4-fluorophenyl)-6-methoxy-7-methyl-1H-indole-2-carboxylic acid To a solution of ethyl 3-(4-fluorophenyl)-6-methoxy-7-methyl-1H-indole-2-carboxylate (180 mg, 0.55 mmol) in THF (3.7 mL) and ethanol (1.8 mL) was added 2M NaOH (2.75 ml). The resulting mixture was stirred at room temperature for 4 days. The mixture was treated with 5M HCl (ca. 2 mL) and concentrated to remove organic solvent. The resulting suspension was filtered to collect a white solid, rinsing with further water and then dried under vacuum at 50° C. to give the title compound.

LCMS Method B: RT=2.99 min, m/z 300.20

Using the above general procedure the following compounds were prepared:

| Example Number | Structure | Analytical Method | Retention Time (mins) | m/z |
|---|---|---|---|---|
| 56 | 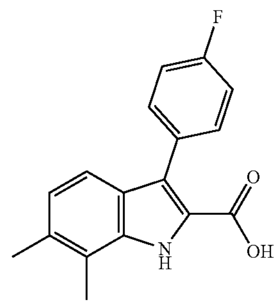 [SMILES: Cc1ccc2c(-c3ccc(F)cc3)c(C(=O)O)[nH]c2c1C] | B | 3.14 | 284.20 |
| 57 | 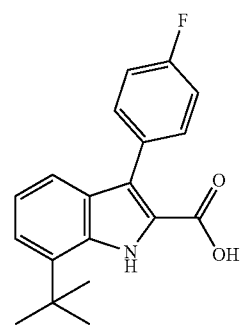 [SMILES: CC(C)(C)c1cccc2c(-c3ccc(F)cc3)c(C(=O)O)[nH]c12] | B | 3.40 | 312.2 |
| 58 | 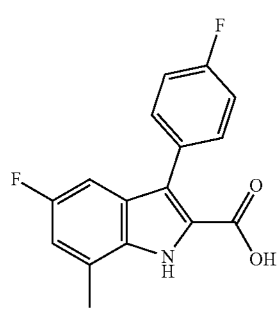 [SMILES: Cc1cc(F)cc2c(-c3ccc(F)cc3)c(C(=O)O)[nH]c12] | B | 3.08 | 286.20 |

-continued
| Example Number | Structure | Analytical Method | Retention Time (mins) | m/z |
|---|---|---|---|---|
| 59 | 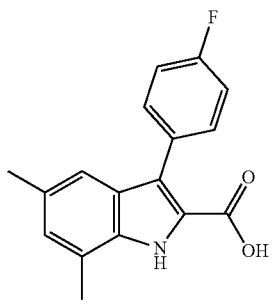 [SMILES: Cc1cc(C)c2[nH]c(C(=O)O)c(-c3ccc(F)cc3)c2c1] | B | 2.37 | 282.20 |
| 60 | 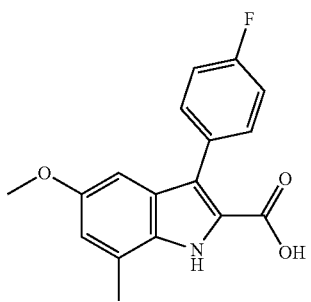 [SMILES: COc1cc(C)c2[nH]c(C(=O)O)c(-c3ccc(F)cc3)c2c1] | B | 2.20 | 300.15 |
| 61 | 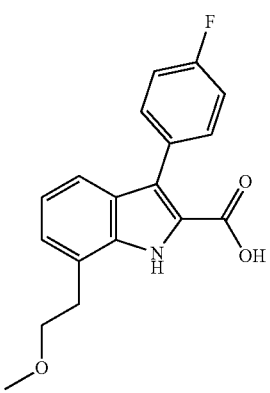 [SMILES: COCCc1cccc2c(-c3ccc(F)cc3)c(C(=O)O)[nH]c12] | B | 3.05 | 314.20 |
| 62 | 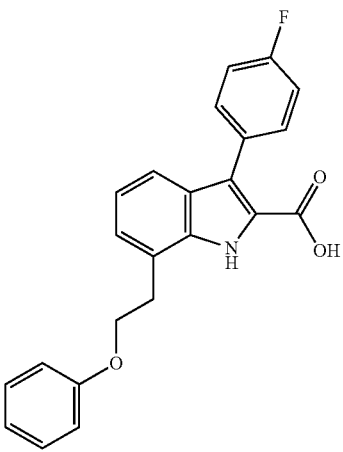 [SMILES: O=C(O)c1[nH]c2c(CCOc3ccccc3)cccc2c1-c1ccc(F)cc1] | B | 3.44 | 374.00 |

-continued
| Example Number | Structure | Analytical Method | Retention Time (mins) | m/z |
|---|---|---|---|---|
| 63 | 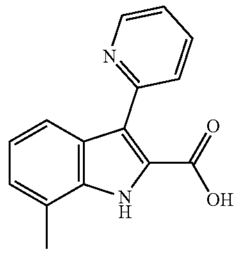 [SMILES: Cc1cccc2c(-c3ccccn3)c(C(=O)O)[nH]c12] | B | 2.32 | 253.20 |
| 64 | 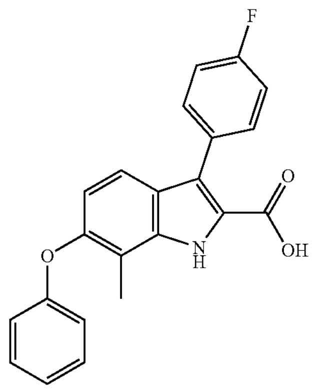 [SMILES: Cc1c(Oc2ccccc2)ccc2c(-c3ccc(F)cc3)c(C(=O)O)[nH]c12] | B | 3.40 | 362.20 |
General Procedure E
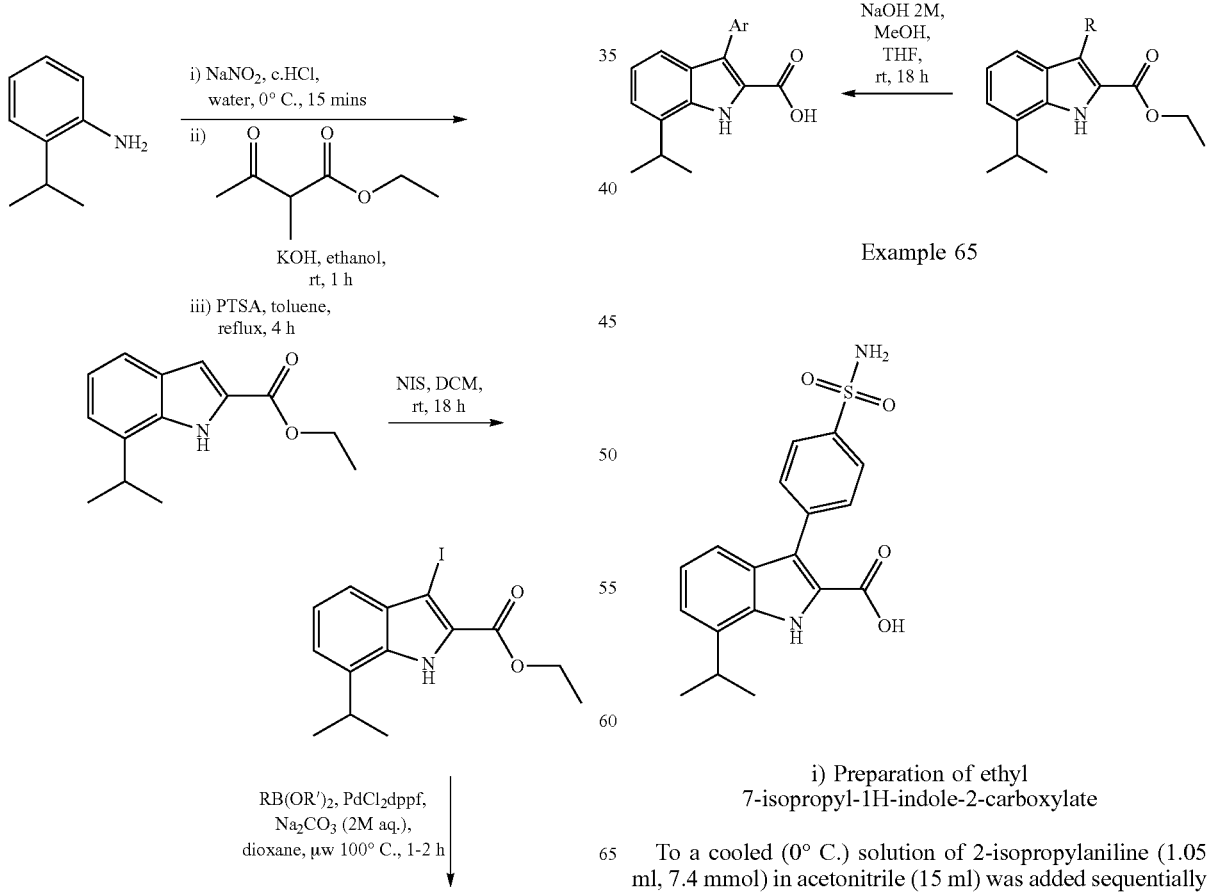
Example 65
i) Preparation of ethyl 7-isopropyl-1H-indole-2-carboxylate
To a cooled (0° C.) solution of 2-isopropylaniline (1.05 ml, 7.4 mmol) in acetonitrile (15 ml) was added sequentially 12M HCl (2.96 ml), water (7.5 mL) and a solution of NaNO$_2$ (0.54 g, 7.77 mmol) in water (7.5 mL). The resulting mixture was stirred for 10 minutes then added to a cooled (0° C.) solution of ethyl 2-methyl-3-oxo-butanoate (1.05 ml, 7.4 mmol) and 8.8M KOH (3.11 ml) in ethanol (10 mL). After 5 minutes, cooling was removed and the mixture allowed to warm to room temperature and stirred for 1 h. The mixture was then concentrated to remove organic solvent and the residue partitioned between EtOAc and water. The organic extracts were washed with brine, dried over $Na_2SO_4$, filtered and concentrated under reduced pressure.

PTSA (2.81 g, 14.79 mmol) in toluene (16 mL) was refluxed under Dean-Stark apparatus for 1 h then a solution of the above residue in toluene (8 mL) added. The resulting mixture was heated for 4 h then cooled to room temperature and partitioned between EtOAc and water. The aqueous phase was further extracted with EtOAc and the combined organic extracts washed with $NaHCO_3$. The combined aqueous phases were further extracted with EtOAc and the total combined organics washed with brine, dried over $Na_2SO_4$, filtered and concentrated under reduced pressure. The residue was subjected to flash chromatography (SNAP-50g, EtOAc in heptane, 0-15%) to give the title compound.

$^1$H NMR (400 MHz, CHLOROFORM-d) δ ppm 8.83 (1H, br. s.) 7.78 (1H, d, J=8.28 Hz) 7.56 (1H, d, J=8.03 Hz) 7.35 (1H, d, J=8.28 Hz) 7.20-7.27 (2H, m) 7.13-7.18 (1H, m) 6.91-6.96 (1H, m) 6.77 (1H, dd, J=8.03, 1.00 Hz) 4.38-4.49 (2H, m) 3.30 (1H, dt, J=13.80, 6.90 Hz) 1.37-1.49 (9H, m).

ii) Preparation of ethyl 3-iodo-7-isopropyl-1H-indole-2-carboxylate

To a solution of ethyl 7-isopropyl-1H-indole-2-carboxylate (0.54 g, 2.33 mmol) in DCM (7 mL) was added N-Iodosuccinimide (0.53 g, 2.33 mmol). The resulting mixture was stirred at room temperature for 20 h then partitioned between DCM and $NaHCO_3$. The organic extracts were washed with brine, dried over $Na_2SO_4$, filtered and concentrated under reduced pressure. The resulting material was taken up in DCM (7 mL) and N-Iodosuccinimide (260 mg, 1.16 mmol) added. The resulting mixture was stirred at room temperature for 20 h. The mixture was partitioned between DCM and $NaHCO_3$. The organic extracts were washed with brine, dried over $Na_2SO_4$, filtered and concentrated under reduced pressure. The residue was taken up in DCM, adsorbed onto silica and subjected to flash chromatography (SNAP-50g, EtOAc in heptane, 0-10%) to give the title compound.

$^1$H NMR (400 MHz, CHLOROFORM-d) δ ppm 9.11 (1H, br. s.) 7.39-7.49 (1H, m) 7.18-7.34 (3H, m) 4.44-4.57 (2H, m) 3.29 (1H, dquin, J=13.71, 6.80, 6.80, 6.80, 6.80 Hz) 1.47-1.55 (3H, m) 1.35-1.45 (6H, m).

iii) Preparation of ethyl 7-isopropyl-3-(4-sulfamoylphenyl)-1H-indole-2-carboxylate A mixture of ethyl 3-iodo-7-isopropyl-1H-indole-2-carboxylate (70 mg, 0.2 mmol), (4-sulfamoylphenyl)boronic acid (39.39 mg, 0.2 mmol), 2M $Na_2CO_3$ (0.39 ml) and Pd(dppf)Cl$_2$ (7.17 mg, 0.01 mmol) was purged with argon then subjected to microwave irradiation at 100° C. for 1 h. The resulting mixture was filtered over celite, rinsing with EtOAc and water. The filtrate was partitioned between 1M HCl and EtOAc. The organic extracts were washed with brine, dried over $Na_2SO_4$, filtered and concentrated under reduced pressure. The residue was subjected to flash chromatography (SNAP-10g, EtOAc in heptane, 0-50%) to give the title compound.

$^1$H NMR (400 MHz, DMSO-d6) δ ppm 11.76 (1H, s) 7.89 (2H, d, J=8.53 Hz) 7.66 (2H, d, J=8.28 Hz) 7.30 (1H, d, J=8.03 Hz) 7.23 (1H, d, J=7.03 Hz) 7.05-7.14 (1H, m) 4.24 (2H, q, J=7.11 Hz) 3.77 (1H, dt, J=13.55, 6.78 Hz) 1.26-1.34 (5H, m) 1.12-1.24 (3H, m).

iv) Preparation of 7-isopropyl-3-(4-sulfamoylphenyl)-1H-indole-2-carboxylic acid To a solution of ethyl 7-isopropyl-3-(4-methylsulfonylphenyl)-1H-indole-2-carboxylate (45 mg, 0.12 mmol) in THF (0.8 mL) and ethanol (0.4 mL) was added 2M NaOH (0.29 ml). The resulting mixture was stirred at room temperature for 24 h. An additional 0.1 mL of 2M NaOH was added to the mixture and stirring continued for a further 4 h. The mixture was concentrated to remove organic solvent then partitioned between EtOAc and water. The organic phase was further washed with 2M NaOH and the combined aqueous phases acidified to pH 1 and re-extracted with EtOAc. The resulting organic phase was dried over $Na_2SO_4$, filtered and concentrated under reduced pressure then dried under vacuum at 55° C. to give the title compound.

LCMS Method B: RT=2.78 min, m/z 357.00.

Using the above general procedure the following compounds were prepared:

| Example Number | Structure | Analytical Method | Retention Time (mins) | m/z |
|---|---|---|---|---|
| 65 | 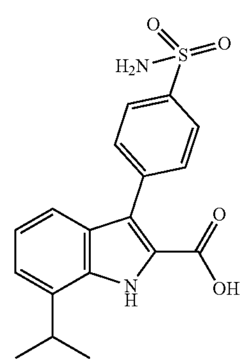 [SMILES: CC(C)c1cccc2c(-c3ccc(S(N)(=O)=O)cc3)c(C(=O)O)[nH]c12] | B | 2.78 | 357.00 |
| 66 | 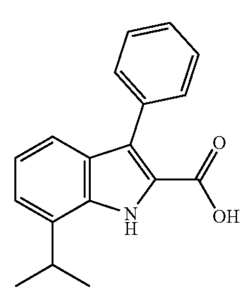 [SMILES: CC(C)c1cccc2c(-c3ccccc3)c(C(=O)O)[nH]c12] | B | 3.19 | 280.20 |

-continued
| Example Number | Structure | Analytical Method | Retention Time (mins) | m/z |
|---|---|---|---|---|
| 67 | 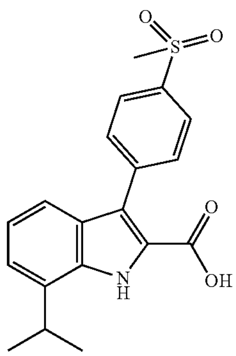 [SMILES: CC(C)c1cccc2c(-c3ccc(S(C)(=O)=O)cc3)c(C(=O)O)[nH]c12] | B | 2.89 | 356.00 |
| 68 | 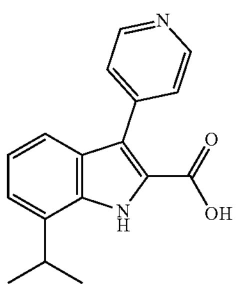 [SMILES: CC(C)c1cccc2c(-c3ccncc3)c(C(=O)O)[nH]c12] | B | 2.14 | 281.20 |
| 69 | 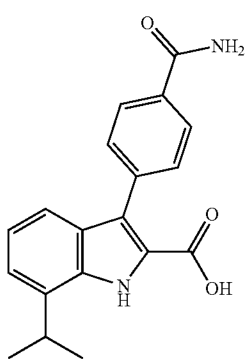 [SMILES: CC(C)c1cccc2c(-c3ccc(C(N)=O)cc3)c(C(=O)O)[nH]c12] | B | 2.66 | 323.20 |
| 70 | 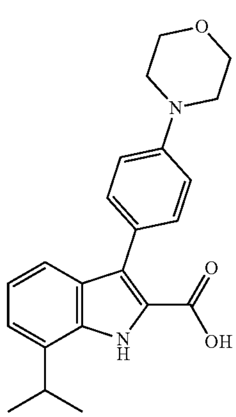 [SMILES: CC(C)c1cccc2c(-c3ccc(N4CCOCC4)cc3)c(C(=O)O)[nH]c12] | B | 3.06 | 365.20 |
-continued
| Example Number | Structure | Analytical Method | Retention Time (mins) | m/z |
|---|---|---|---|---|
| 71 | 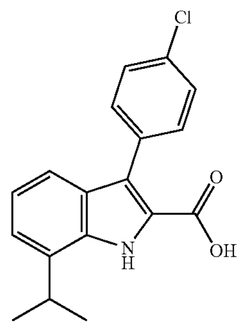 [SMILES: CC(C)c1cccc2c(-c3ccc(Cl)cc3)c(C(=O)O)[nH]c12] | B | 3.38 | 314.20 |
| 72 | 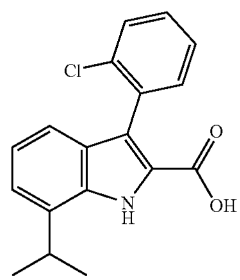 [SMILES: CC(C)c1cccc2c(-c3ccccc3Cl)c(C(=O)O)[nH]c12] | B | 3.22 | 314.00 |
General Procedure F
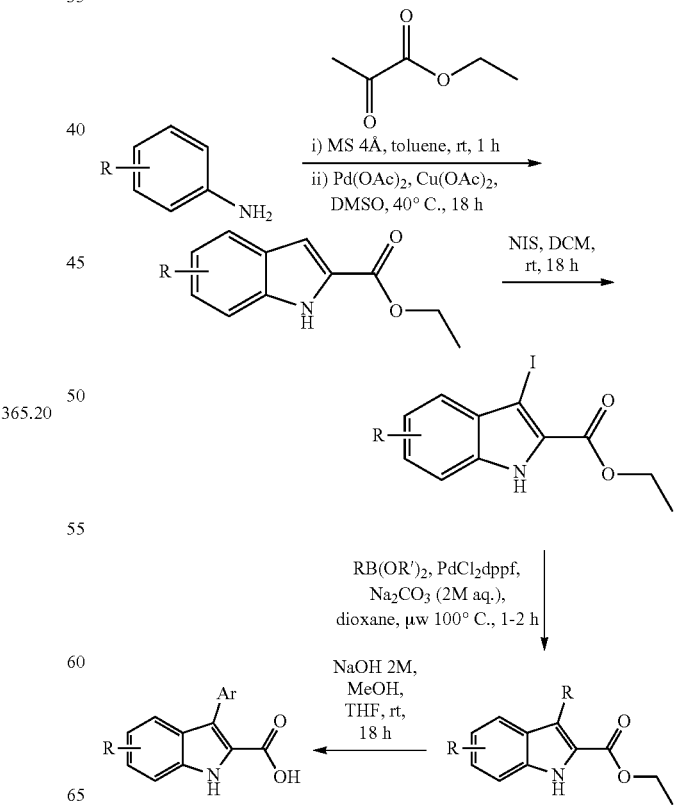

Example 73

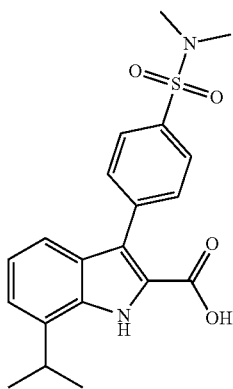 [SMILES: CC(C)c1cccc2c(-c3ccc(S(=O)(=O)N(C)C)cc3)c(C(=O)O)[nH]c12]

i) Preparation of ethyl 7-isopropyl-1H-indole-2-carboxylate

To a flask charged with molecular sieves (4 Å, 1.5 g) under argon was added toluene (3.5 mL) followed by 2-isopropylaniline (0.79 ml, 5.55 mmol) and ethyl 2-oxopropanoate (1.23 ml, 11.09 mmol). The resulting mixture was stirred at room temperature. The mixture was filtered through cotton wool to remove sieves, rinsing with EtOAc and the filtrate concentrated under reduced pressure. The residue was placed under argon, taken up in DMSO (25 ml) and Copper (II) acetate (1.51 g, 8.32 mmol) and Pd(OAc)$_2$ (0.12 g, 0.55 mmol) added. The resulting mixture was heated to 40° C. for 18 h. The mixture was filtered over celite, rinsing with EtOAc and 1M HCl. The filtrate was separated and the aqueous phase further extracted with EtOAc then the combined organic extracts washed with brine (×2), dried over Na$_2$SO$_4$, filtered and concentrated under reduced pressure. The material was taken up in DCM, adsorbed onto silica and purified by flash chromatography (SNAP-50g, EtOAc in heptane, 0-20%) to give the title compound.

$^1$H NMR (400 MHz, CHLOROFORM-d) δ ppm 8.82 (2H, br. s.) 7.56 (2H, d, J=7.78 Hz) 7.25 (2H, d, J=2.01 Hz) 7.18-7.24 (2H, m) 7.12-7.18 (2H, m) 4.44 (4H, q, J=7.03 Hz) 3.29 (2H, dquin, J=13.80, 6.90, 6.90, 6.90, 6.90 Hz) 1.36-1.50 (15H, m).

ii) Preparation of ethyl 3-iodo-7-isopropyl-1H-indole-2-carboxylate

To a solution of ethyl 7-isopropyl-1H-indole-2-carboxylate (875 mg, 3.78 mmol) in DCM (11.3 mL) was added N-Iodosuccinimide (893.68 mg, 3.97 mmol). The resulting mixture was stirred at room temperature for 16 h then partitioned between DCM and sat. aq. NaHCO$_3$. The organic extracts were washed with brine, dried over Na$_2$SO$_4$, filtered and concentrated under reduced pressure. The residue was taken up in DCM, adsorbed onto silica and purified by flash chromatography (SNAP-50g, EtOAc in heptane, 0-15%) to give the title compound.

$^1$H NMR (400 MHz, CHLOROFORM-d) δ ppm 9.11 (1H, br. s.) 7.44 (1H, d, J=7.78 Hz) 7.20-7.30 (3H, m) 4.50 (2H, q, J=7.03 Hz) 3.29 (1H, dquin, J=13.71, 6.86, 6.86, 6.86, 6.86 Hz) 1.51 (3H, t, J=7.03 Hz) 1.35-1.45 (6H, m).

iii) Preparation of ethyl 3-[4-(dimethylsulfamoyl)phenyl]-7-isopropyl-1H-indole-2-carboxylate A mixture of ethyl 3-iodo-7-isopropyl-1H-indole-2-carboxylate (250 mg, 0.7 mmol), [4-(dimethylsulfamoyl)phenyl]boronic acid (192.39 mg, 0.84 mmol), 2M Na$_2$CO$_3$ (1.4 ml) and Pd(dppf)Cl$_2$ (25.61 mg, 0.03 mmol) in dioxane (6.2 mL) was purged with argon then subjected to microwave irradiation at 100° C. for 2 h. The resulting mixture was filtered over celite, rinsing with EtOAc and water. The filtrate was partitioned between EtOAc and 1M HCl and the aqueous phase further extracted with EtOAc. The combined organic extracts were washed with brine, dried over Na$_2$SO$_4$, filtered and concentrated under reduced pressure. The residue was purified by flash chromatography (Telos 12 g, EtOAc in heptane, 0-50%) to give the title compound.

$^1$H NMR (400 MHz, CHLOROFORM-d) δ ppm 9.01 (1H, br. s.) 7.88 (2H, d, J=8.28 Hz) 7.75 (2H, d, J=8.28 Hz) 7.44 (1H, d, J=8.03 Hz) 7.26-7.33 (3H, m) 7.14-7.24 (1H, m) 4.33 (2H, q, J=7.19 Hz) 3.35 (1H, dquin, J=13.74, 6.92, 6.92, 6.92, 6.92 Hz) 2.70-2.88 (6H, m) 1.41-1.53 (6H, m) 1.18-1.32 (3H, m).

iv) Preparation of 7-isopropyl-3-[4-(methylsulfamoyl)phenyl]-1H-indole-2-carboxylic acid To a solution of ethyl 3-[4-(dimethylsulfamoyl)phenyl]-7-isopropyl-1H-indole-2-carboxylate (240 mg, 0.58 mmol) in THF (3.9 mL) and ethanol (1.9 mL) was added 2M NaOH (2.32 ml). The resulting mixture was stirred at room temperature for 16 h. The mixture was quenched with 5M HCl (ca. 3 mL) and concentrated to remove organic solvent. The precipitated off-white solid was collected by filtration, washed with water and dried to give the title compound.

LCMS Method B: RT=3.09 min, m/z 387.20

Using the above general procedure the following compounds were prepared:

| Example Number | Structure | Analytical Method | Retention Time (mins) | m/z |
|---|---|---|---|---|
| 73 | 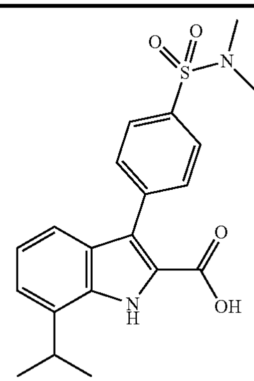 | B | 3.09 | 387.20 |

-continued
| Example Number | Structure | Analytical Method | Retention Time (mins) | m/z |
|---|---|---|---|---|
| 74 | 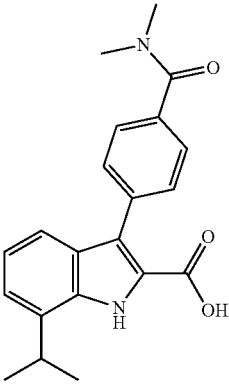 [SMILES: CC(C)c1cccc2c(-c3ccc(C(=O)N(C)C)cc3)c(C(=O)O)[nH]c12] | B | 2.91 | 351.20 |
| 75 | 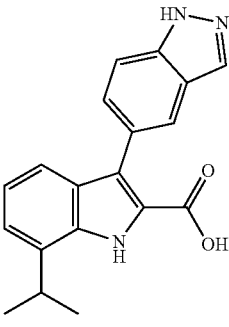 [SMILES: CC(C)c1cccc2c(-c3ccc4[nH]ncc4c3)c(C(=O)O)[nH]c12] | B | 2.86 | 320.20 |
| 76 | 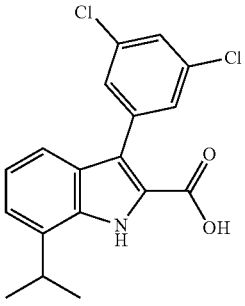 [SMILES: CC(C)c1cccc2c(-c3cc(Cl)cc(Cl)c3)c(C(=O)O)[nH]c12] | B | 3.66 | 346.00 |
| 77 | 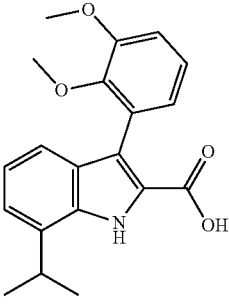 [SMILES: COc1cccc(-c2c(C(=O)O)[nH]c3c(C(C)C)cccc23)c1OC] | B | 3.13 | 338.20 |

-continued

| Example Number | Structure | Analytical Method | Retention Time (mins) | m/z |
|---|---|---|---|---|
| 78 | 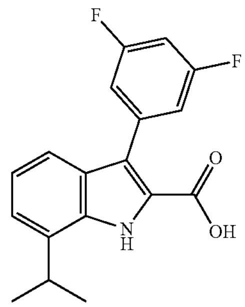 [SMILES: CC(C)c1cccc2c(-c3cc(F)cc(F)c3)c(C(=O)O)[nH]c12] | B | 3.36 | 315.20 |
| 79 | 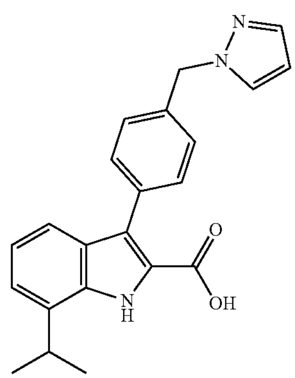 [SMILES: CC(C)c1cccc2c(-c3ccc(Cn4cccn4)cc3)c(C(=O)O)[nH]c12] | B | 3.10 | 360.20 |
| 80 | 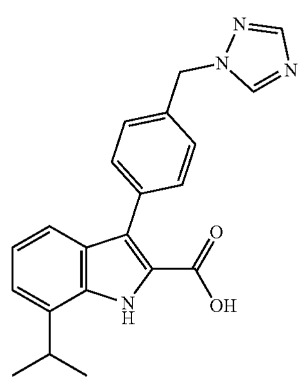 [SMILES: CC(C)c1cccc2c(-c3ccc(Cn4cncn4)cc3)c(C(=O)O)[nH]c12] | B | 2.88 | 361.20 |
| 81 | 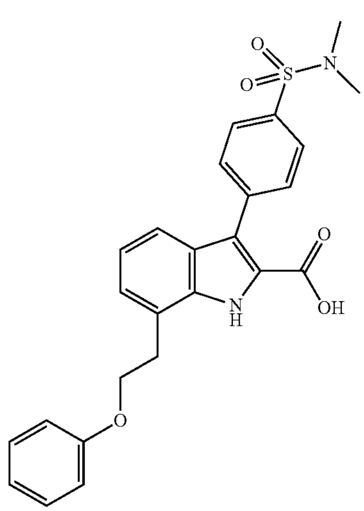 [SMILES: CN(C)S(=O)(=O)c1ccc(-c2c(C(=O)O)[nH]c3c(CCOc4ccccc4)cccc23)cc1] | B | 3.26 | 465.00 |

| Example Number | Structure | Analytical Method | Retention Time (mins) | m/z |
|---|---|---|---|---|
| 82 | 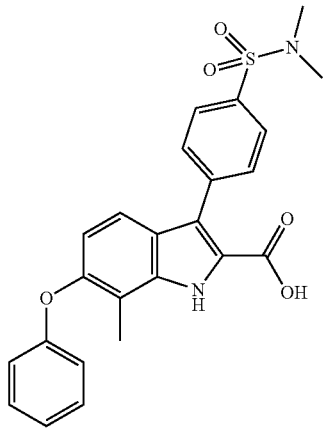 [SMILES: Cc1c(Oc2ccccc2)ccc2c(-c3ccc(S(=O)(=O)N(C)C)cc3)c(C(=O)O)[nH]c12] | B | 3.27 | 451.00 |
| 83 | 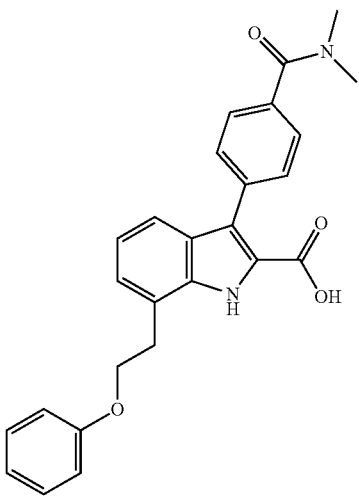 [SMILES: CN(C)C(=O)c1ccc(-c2c(C(=O)O)[nH]c3c(CCOc4ccccc4)cccc23)cc1] | B | 3.10 | 429.20 |
| 84 | 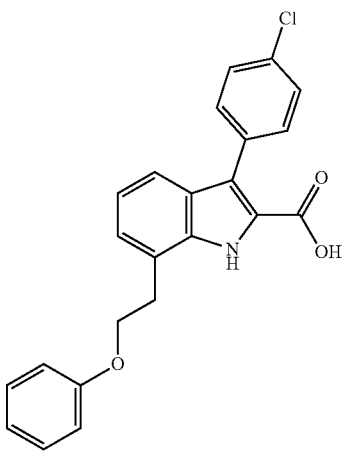 | B | 3.55 | 392.00 |

-continued

| Example Number | Structure | Analytical Method | Retention Time (mins) | m/z |
|---|---|---|---|---|
| 85 | 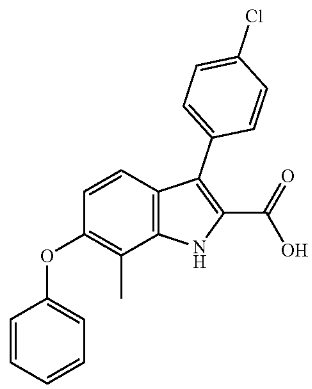 [SMILES: Cc1c(Oc2ccccc2)ccc2c(-c3ccc(Cl)cc3)c(C(=O)O)[nH]c12] | B | 3.54 | 376.00 |
| 86 | 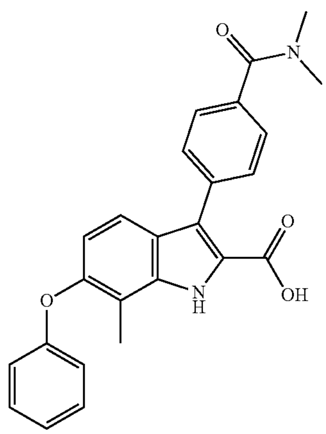 [SMILES: Cc1c(Oc2ccccc2)ccc2c(-c3ccc(C(=O)N(C)C)cc3)c(C(=O)O)[nH]c12] | B | 3.07 | 415.20 |
| 87 | 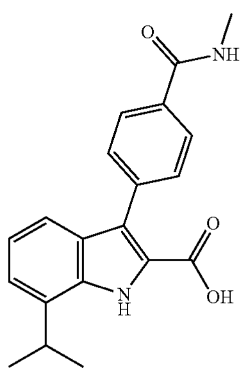 [SMILES: CNC(=O)c1ccc(-c2c(C(=O)O)[nH]c3c(C(C)C)cccc23)cc1] | B | 2.14 | 337.20 |
| 88 | 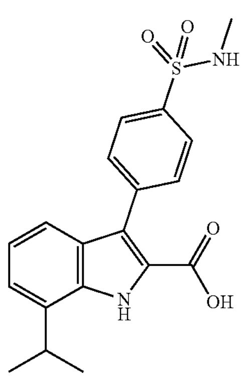 [SMILES: CNS(=O)(=O)c1ccc(-c2c(C(=O)O)[nH]c3c(C(C)C)cccc23)cc1] | B | 2.26 | 373.20 |

-continued

| Example Number | Structure | Analytical Method | Retention Time (mins) | m/z |
|---|---|---|---|---|
| 89 | 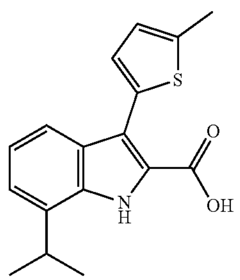 [SMILES: Cc1ccc(-c2c(C(=O)O)[nH]c3c(C(C)C)cccc23)s1] | B | 3.50 | 300.00 |
| 90 | 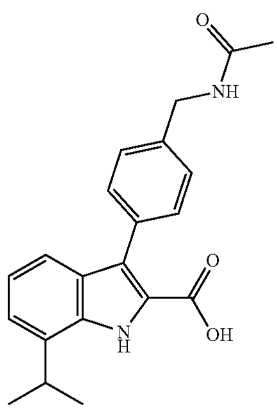 [SMILES: CC(=O)NCc1ccc(-c2c(C(=O)O)[nH]c3c(C(C)C)cccc23)cc1] | B | 2.98 | 351.20 |
| 91 | 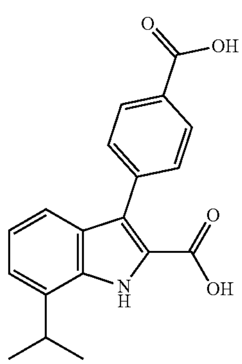 [SMILES: CC(C)c1cccc2c(-c3ccc(C(=O)O)cc3)c(C(=O)O)[nH]c12] | B | 3.12 | 322.20 |
| 92 | 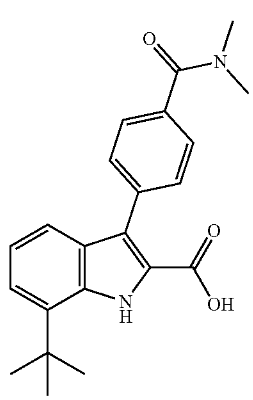 [SMILES: CN(C)C(=O)c1ccc(-c2c(C(=O)O)[nH]c3c(C(C)(C)C)cccc23)cc1] | B | 3.15 | 365.20 |

-continued

| Example Number | Structure | Analytical Method | Retention Time (mins) | m/z |
|---|---|---|---|---|
| 93 | 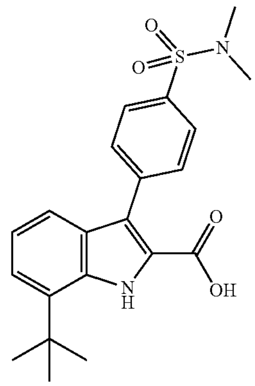 [SMILES: CN(C)S(=O)(=O)c1ccc(-c2c(C(=O)O)[nH]c3c(C(C)(C)C)cccc23)cc1] | B | 3.35 | 401.20 |
| 94 | 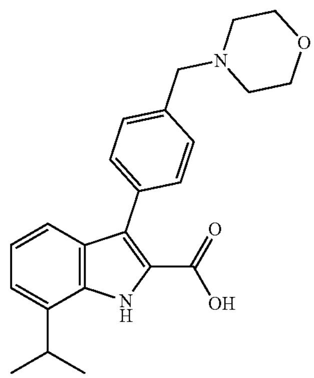 [SMILES: CC(C)c1cccc2c(-c3ccc(CN4CCOCC4)cc3)c(C(=O)O)[nH]c12] | B | 2.31 | 377.20 |
| 95 | 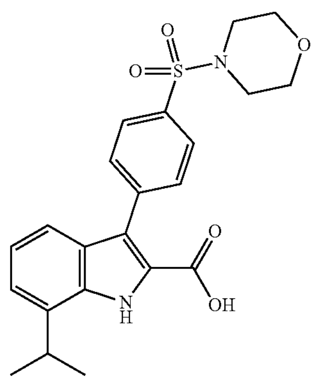 [SMILES: CC(C)c1cccc2c(-c3ccc(S(=O)(=O)N4CCOCC4)cc3)c(C(=O)O)[nH]c12] | B | 3.06 | 427.00 |
| 96 | 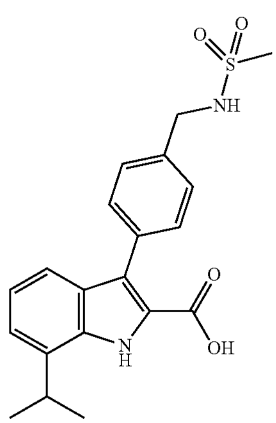 [SMILES: CC(C)c1cccc2c(-c3ccc(CNS(C)(=O)=O)cc3)c(C(=O)O)[nH]c12] | B | 2.89 | 385.00 |

-continued
| Example Number | Structure | Analytical Method | Retention Time (mins) | m/z |
|---|---|---|---|---|
| 97 | 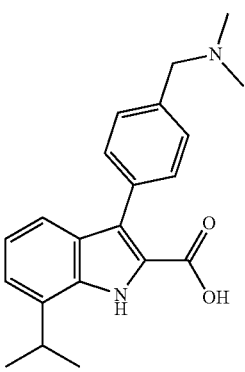 [SMILES: CC(C)c1cccc2c(-c3ccc(CN(C)C)cc3)c(C(=O)O)[nH]c12] | B | 2.30 | 337.20 |
| 98 | 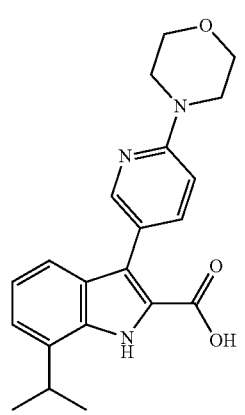 [SMILES: CC(C)c1cccc2c(-c3ccc(N4CCOCC4)nc3)c(C(=O)O)[nH]c12] | B | 2.39 | 366.20 |
| 99 | 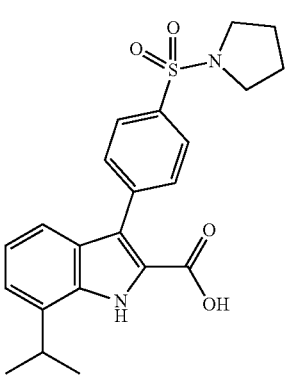 [SMILES: CC(C)c1cccc2c(-c3ccc(S(=O)(=O)N4CCCC4)cc3)c(C(=O)O)[nH]c12] | B | 3.15 | 413.20 |
| 100 | 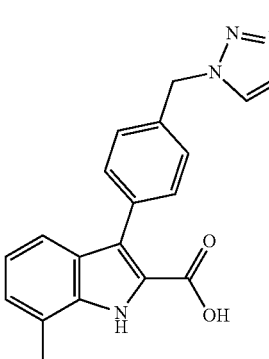 | B | 3.02 | 360.20 |

| Example Number | Structure | Analytical Method | Retention Time (mins) | m/z |
|---|---|---|---|---|
| 101 | 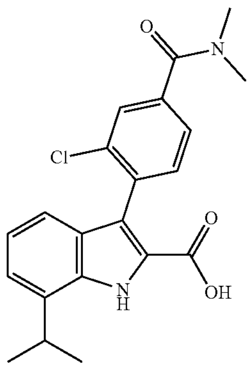 [SMILES: CC(C)c1cccc2c(-c3ccc(C(=O)N(C)C)cc3Cl)c(C(=O)O)[nH]c12] | B | 2.91 | 385.00 |

Example 102

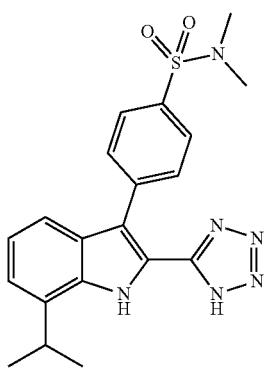 [SMILES: CC(C)c1cccc2c(-c3ccc(S(=O)(=O)N(C)C)cc3)c(-c3nnn[nH]3)[nH]c12]

i) Preparation of 3-[4-(dimethylsulfamoyl)phenyl]-7-isopropyl-1H-indole-2-carboxamide A solution of ethyl 3-[4-(dimethylsulfamoyl)phenyl]-7-isopropyl-1H-indole-2-carboxylate (100 mg, 0.24 mmol) in 7M $NH_3$ (2.41 ml) was subjected to microwave irradiation at 50° C. for 2 h. The mixture was further irradiated at 100° C. for 1 h 40 minutes. The mixture was concentrated under reduced pressure then taken up in 7M $NH_3$ (2.41 ml) and transferred to a microwave vial and heated at 50° C. for 22 h then 70° C. for 72 h. The mixture was concentrated under reduced pressure to give a 5:1 mixture of methyl 3-(4-(N,N-dimethylsulfamoyl)phenyl)-7-isopropyl-1H-indole-2-carboxylate to the title compound and was used directly in the next step.

ii) Preparation of 4-(2-cyano-7-isopropyl-1H-indol-3-yl)-N,N-dimethyl-benzenesulfonamide To a cooled (0° C.) suspension of the mixture obtained above (109 mg) and TEA (0.09 ml, 0.62 mmol) in Tetrahydrofuran (2.8 ml) was added dropwise trifluoroacetic anhydride (0.15 ml, 1.07 mmol). The reaction mixture was stirred at room temperature for 3 h. After this time an additional aliquot of trifluoroacetic anhydride (0.1 ml) and TEA (0.2 ml) was added. The mixture was stirred for a further 18.5 h. The mixture was partitioned between EtOAc and sat. aq. $NaHCO_3$. The aqueous phase was further extracted with EtOAc and the combined organic extracts washed with brine, dried over $Na_2SO_4$, filtered and concentrated under reduced pressure. The residue was taken up in DCM, adsorbed onto silica and purified by flash chromatography (Telos 4 g, EtOAc in heptane, 0-30% then flush up to 100%) to give the title compound.

$^1$H NMR (400 MHz, CHLOROFORM-d) δ ppm 9.28 (1H, s) 7.77-7.94 (4H, m) 7.54-7.64 (1H, m) 7.13-7.31 (2H, m) 3.13-3.30 (1H, m) 2.63-2.79 (6H, m) 1.26-1.41 (6H, m).

iii) Preparation of 4-[7-isopropyl-2-(1H-tetrazol-5-yl)-1H-indol-3-yl]-N,N-dimethyl-benzenesulfonamide To a solution of 4-(2-cyano-7-isopropyl-1H-indol-3-yl)-N,N-dimethyl-benzenesulfonamide (49 mg, 0.13 mmol) in DMF (1.3 mL) was added $NaN_3$ (17.34 mg, 0.27 mmol) and $NH_4Cl$ (7.13 mg, 0.13 mmol). The resulting mixture was heated at 120° C. under argon for 16 h, after. Additional $NaN_3$ (17.34 mg, 0.27 mmol) and $NH_4Cl$ (7.13 mg, 0.13 mmol) were added and heating continued for a further 23 h. The resulting mixture was cooled to room temperature and treated with 1M HCl (ca. 4 mL). The mixture was partitioned between EtOAc and brine. The aqueous phase was further extracted with EtOAc and the combined organic extracts washed with brine (×2), dried over $Na_2SO_4$, filtered and concentrated under reduced pressure. The residue was taken up in DMSO/MeOH (1:1, 1 mL) and purified by preparative HPLC. Fractions corresponding to the desired product were combined and concentrated under reduced pressure then further dried under vacuum at 50° C. to give the title compound.

LCMS Method B: RT=3.07 min, m/z 411.20

General Procedure G

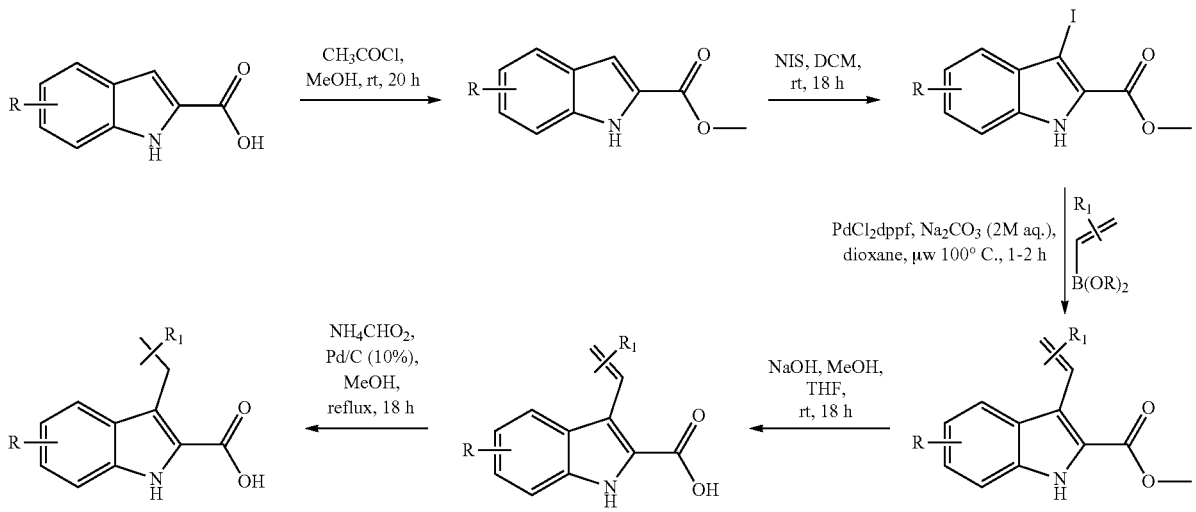

Example 103

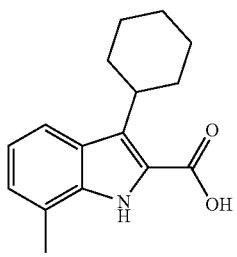 [SMILES: Cc1cccc2c(C3CCCCC3)c(C(=O)O)[nH]c12]

i) Preparation of methyl 3-(cyclohexen-1-yl)-7-methyl-1H-indole-2-carboxylate A mixture of methyl 3-iodo-7-methyl-1H-indole-2-carboxylate (160 mg, 0.51 mmol), 2-(cyclohexen-1-yl)-4,4,5,5-tetramethyl-1,3,2-dioxaborolane (126.8 mg, 0.61 mmol), 2M Na$_2$CO$_3$ (1.02 ml) and Pd(dppf)Cl$_2$ (18.58 mg, 0.03 mmol) in dioxane (4.4 mL) was purged with argon then subjected to microwave irradiation at 100° C. for 2.5 h. The mixture was filtered over celite, rinsing with EtOAc and water. The filtrate was partitioned between EtOAc and 1M HCl and the organic extracts washed with brine, dried over Na$_2$SO$_4$, filtered and concentrated under reduced pressure. The residue was taken up in DCM/MeOH, adsorbed onto silica and subjected to flash chromatography (SNAP-10g, EtOAc in heptane, 0-15%) to give the title compound.

$^1$H NMR (400 MHz, CHLOROFORM-d) δ ppm 8.44-8.61 (1H, m) 7.45 (1H, d, J=8.03 Hz) 6.94-7.09 (2H, m) 5.73 (1H, dt, J=3.58, 1.85 Hz) 3.81-3.91 (3H, m) 2.39-2.47 (3H, m) 2.24-2.33 (2H, m) 2.15-2.23 (2H, m) 1.63-1.80 (4H, m).

ii) Preparation of 3-(cyclohexen-1-yl)-7-methyl-1H-indole-2-carboxylic acid To a solution of methyl 3-(cyclohexen-1-yl)-7-methyl-1H-indole-2-carboxylate (49 mg, 0.18 mmol) in THF (1.2 mL) and methanol (0.6 mL) was added 2M NaOH (0.45 ml).

The resulting mixture was stirred for 24 h then treated with ca. 2 mL 1M HCl and concentrated under reduced pressure. The resulting aqueous suspension was filtered to collect a yellow solid. The material was taken up in DCM/MeOH, adsorbed onto silica and subjected to flash chromatography (SNAP-10g, MeOH in DCM, 0-50%) to give the title compound with other unknown impurities. The material was used in the next step without further purification.

iii) Preparation of methyl 3-cyclohexyl-7-methyl-1H-indole-2-carboxylate

The material obtained above (33 mg) and ammonium formate (100.43 mg, 1.59 mmol) in methanol (3 mL) was purged with argon then Pd/C (10%, 9.13 mg, 0.01 mmol) added and the mixture heated to reflux for 18 h. The resulting mixture was filtered over celite, rinsing with further methanol. The filtrate was concentrated under reduced pressure and the residue partitioned between EtOAc and water. The organic extracts were washed with brine, dried over Na$_2$SO$_4$, filtered and concentrated under reduced pressure. The material was taken up in DMSO/MeOH (1:1, 1 mL) and purified by preparative HPLC to give the title compound.

LCMS Method B RT=3.36 min, m/z 256.20.

Using the above general procedure the following compounds were prepared:

| Example Number | Structure | Analytical Method | Retention Time (mins) | m/z |
|---|---|---|---|---|
| 104 | ![structure] | B | 3.13 | 244.20 |

Example 105

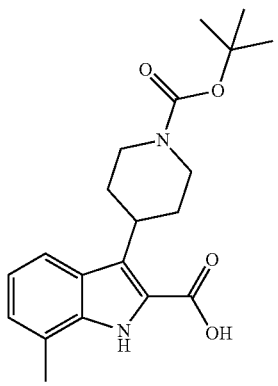 [SMILES: Cc1cccc2c(C3CCN(C(=O)OC(C)(C)C)CC3)c(C(=O)O)[nH]c12]

i) Preparation of methyl 3-(1-tert-butoxycarbonyl-3,6-dihydro-2H-pyridin-4-yl)-7-methyl-1H-indole-2-carboxylate A mixture of methyl 3-iodo-7-methyl-1H-indole-2-carboxylate (160 mg, 0.51 mmol), tert-butyl 4-(4,4,5,5-tetramethyl-1,3,2-dioxaborolan-2-yl)-3,6-dihydro-2H-pyridine-1-carboxylate (188.41 mg, 0.61 mmol), 2M $Na_2CO_3$ (1.02 ml) and $Pd(dppf)Cl_2$ (18.58 mg, 0.03 mmol) in dioxane (4.4 mL) was subjected to microwave irradiation at 100° C. for 1 h. The resulting mixture was filtered over celite, rinsing with EtOAc and water. The filtrate was partitioned between EtOAc and 1M HCl and the organic extracts washed with brine, dried over $Na_2SO_4$, filtered and concentrated under reduced pressure. The residue was subjected to flash chromatography (SNAP-10g, EtOAc in heptane, 0-25%) to give the title compound.
$^1$H NMR (400 MHz, CHLOROFORM-d) δ ppm 8.65-8.77 (1H, m) 7.53 (1H, d, J=8.03 Hz) 7.05-7.20 (2H, m) 5.81 (1H, br. s.) 4.16 (2H, br. s.) 3.89-4.04 (3H, m) 3.65-3.77 (2H, m) 2.47-2.60 (5H, m) 1.58 (5H, s) 1.54 (9H, s).

ii) Preparation of methyl 3-(1-tert-butoxycarbonyl-4-piperidyl)-7-methyl-1H-indole-2-carboxylate A mixture of methyl 3-(1-tert-butoxycarbonyl-3,6-dihydro-2H-pyridin-4-yl)-7-methyl-1H-indole-2-carboxylate (150 mg, 0.4 mmol), Ammonium formate (331.92 mg, 5.26 mmol) and Pd/C (10%, 30.16 mg, 0.03 mmol) in methanol (30 mL) was purged with argon then heated to reflux for 20 h. The mixture was filtered over Celite™, rinsing with methanol and the filtrate concentrated under reduced pressure. The residue was partitioned between EtOAc and water and the organic extracts washed with brine, dried over $Na_2SO_4$, filtered and concentrated under reduced pressure and used directly without further purification.

iii) Preparation of 3-(1-tert-butoxycarbonyl-4-piperidyl)-7-methyl-1H-indole-2-carboxylic acid To a mixture of methyl 3-(1-tert-butoxycarbonyl-4-piperidyl)-7-methyl-1H-indole-2-carboxylate (151 mg, 0.41 mmol) in THF (3 mL) and MeOH (1 mL) was added 2M NaOH (1.01 ml). The resulting mixture was stirred at room temperature for 16 h then concentrated under reduced pressure. The residue was treated with 1M HCl (ca. 2.5 mL) and filtered to collect a white solid. The solid was washed with water, air dried for 30 minutes then further dried under vacuum at 50° C. The filtrate was concentrated to low volume and further white solid collected by filtration, air dried then dried under vacuum at 50° C. and combined with the previously obtained solid to afford the title compound
LCMS Method B: RT=3.23 min, m/z 357.20

Example 106

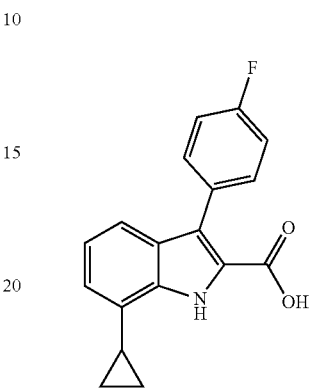

i) Preparation of ethyl 7-cyclopropyl-1H-indole-2-carboxylate

A mixture of ethyl 7-bromo-1H-indole-2-carboxylate (300 mg, 1.12 mmol), cyclopropylboronic acid (192.23 mg, 2.24 mmol), 2M $Na_2CO_3$ (2.8 ml) and $Pd(dppf)Cl_2$ (40.94 mg, 0.06 mmol) in dioxane (9.7 mL) was purged with argon then subjected to microwave irradiation at 100° C. for 2 h. The resulting mixture was filtered over celite, rinsing with EtOAc and water. The filtrate was partitioned between EtOAc and 1M HC. The aqueous phase was extracted with EtOAc and the combined organic extracts washed with brine, dried over $Na_2SO_4$, filtered and concentrated under reduced pressure. The residue was taken up in DCM, adsorbed onto silica and purified by flash chromatography (Telos 12 g, EtOAc in heptane, 0-15%) to give the title compound contaminated with an unknown related impurity. The material was used in the next step without further purification.

ii) Preparation of ethyl 7-cyclopropyl-3-iodo-1H-indole-2-carboxylate

To the mixture obtained above (130 mg, 0.57 mmol) in DCM (1.5 mL) was added N-Iodosuccinimide (133.94 mg, 0.6 mmol). The resulting mixture was stirred at room temperature for 16 h. The mixture was partitioned between EtOAc and $NaHCO_3$. The organic extracts were washed with brine, dried over $Na_2SO_4$, filtered and concentrated under reduced pressure. The residue was taken up in DCM, adsorbed onto silica and purified by flash chromatography (Telos 12 g, EtOAc in heptane, 0-10%) to give the title compound.
$^1$H NMR (400 MHz, CHLOROFORM-d) δ ppm 9.30 (1H, br. s.) 7.43 (1H, d, J=8.03 Hz) 7.14-7.23 (1H, m) 7.08-7.13 (1H, m) 4.51 (2H, q, J=7.19 Hz) 2.01-2.15 (1H, m) 1.46-1.55 (3H, m) 1.01-1.13 (2H, m) 0.75-0.84 (2H, m).

iii) Preparation of ethyl 7-cyclopropyl-3-(4-fluorophenyl)-1H-indole-2-carboxylate A mixture of ethyl 3-iodo-7-isopropyl-1H-indole-2-carboxylate (90 mg, 0.25 mmol), (3,5-dichlorophenyl)boronic acid (48.08 mg, 0.25 mmol), 2M Na$_2$CO$_3$ (0.5 ml) and Pd(dppf)Cl$_2$ (9.22 mg, 0.01 mmol) in dioxane (2.2 mL) was purged with argon then subjected to microwave irradiation at 100° C. for 1 h. The resulting mixture was filtered over celite, rinsing with EtOAc and water. The filtrate was partitioned between EtOAc and 1M HCl. The organic extracts were washed with brine, dried over Na$_2$SO$_4$, filtered and concentrated under reduced pressure. The residue was taken up in DCM, adsorbed onto silica and purified by flash chromatography (Telos 12 g, EtOAc in heptane, 0-10%) to give the title compound.

$^1$H NMR (400 MHz, CHLOROFORM-d) δ ppm 9.10 (1H, br. s.) 7.47-7.58 (2H, m) 7.39-7.47 (1H, m) 7.05-7.18 (4H, m) 4.32 (2H, q, J=7.19 Hz) 2.07-2.18 (1H, m) 1.19-1.34 (3H, m) 0.99-1.12 (2H, m) 0.76-0.88 (2H, m).

iv) Preparation of 7-cyclopropyl-3-(4-fluorophenyl)-1H-indole-2-carboxylic acid

A solution of ethyl 7-cyclopropyl-3-(4-fluorophenyl)-1H-indole-2-carboxylate (47.5 mg, 0.15 mmol) and 2M NaOH (0.59 ml) in THF (1 mL) and ethanol (0.5 mL) was heated at 50° C. for 3 h then treated with 1M HCl (ca. 2 mL) and concentrated to remove organic solvent. The resulting precipitate was collected by filtration, washed with water, air dried for ca. 30 minutes then further dried under vacuum at 50° C. to give the title compound.

LCMS Method B: RT=3.21 min, m/z 294.00.

Example 107

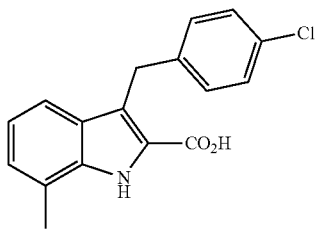 [SMILES: Cc1cccc2c(Cc3ccc(Cl)cc3)c(C(=O)O)[nH]c12]

i) Preparation of ethyl 4-(4-chlorophenyl)-2-oxo-butanoate

To a mixture of Mg turnings (221.5 mg, 9.11 mmol) in dry THF (10 ml) was added a small piece of iodine. The dark brown colour faded away after a few minutes to a pale yellow. After 60 minutes a clear colourless solution formed. 1-(Bromomethyl)-4-chloro-benzene (1.43 ml, 9.11 mmol) was added and the mixture subjected to ultrasound radiation for 2 minutes to initiate the reaction. The solution was stirred for 60 minutes at RT to give a clear yellow solution (Mg fully dissolved) that was added dropwise to a −78° C. cold solution of diethyl oxalate (1.17 ml, 8.66 mmol) in THF (15 ml) over 30 minutes. After stirring for 16 h at −78° C. to room temperature, the reaction was quenched with aq. NH$_4$Cl (30 ml) and the product extracted into EtOAc (2×50 ml). The combined organic extracts were dried with Na$_2$SO$_4$, evaporated to dryness to give a brown oil. The material was purified by chromatography (0-10% EtOAc/heptane) to give the title compound contaminated with a small amount of diethyl oxalate, used directly in the next step without further purification.

ii) Preparation of 3-[(4-chlorophenyl)methyl]-7-methyl-1H-indole-2-carboxylate

A mixture of o-Tolylhydrazine hydrochloride (408.63 mg, 2.58 mmol), the material obtained above (620 mg) and PTSA (980 mg, 5.15 mmol) was stirred in toluene (10 ml) at rt for 1 hour. PTSA (980 mg, 5.15 mmol) was added and the reaction heated to reflux for 2 h and then cooled. EtOAc (30 ml) was added and partitioned with saturated aq. NaHCO$_3$ solution (2×20 ml). The organic layer was separated, dried over Na$_2$SO$_4$, filtered and concentrated. The material was purified by chromatography (0-10% EtOAc/heptane) to afford the title compound.

$^1$H NMR (400 MHz, CHLOROFORM-d) b ppm: 8.68 (br s, 1H), 7.44 (d, J=8.0 Hz, 1H), 7.19 (s, 4H), 7.13 (m, 1H), 7.05 (m, 1H), 4.47 (s, 2H), 4.20 (q, J=7.0 Hz, 2H), 2.52 (s, 3H), 1.39 (t, J=7.0 Hz).

iii) Preparation of 3-[(4-chlorophenyl)methyl]-7-methyl-1H-indole-2-carboxylic acid To a solution of ethyl 3-[(4-chlorophenyl)methyl]-7-methyl-1H-indole-2-carboxylate (250 mg, 0.76 mmol) in THF (5.0 mL) and methanol (2.5 mL) was added 2M aq. NaOH (1.90 ml, 3.81 mmol). The reaction was stirred for 16 h at room temperature. The reaction was concentrated at reduced pressure and the residue dissolved in water, acidified with 1M aq. HCl and extracted into EtOAc (2×30 ml). The organic extracts were combined, dried over Na$_2$SO$_4$, filtered and concentrated at reduced pressure. This material was purified by chromatography (0-50% EtOAc/heptane) followed by preparative HPLC to give the title compound.

LCMS Method B: RT=2.21 min, m/z 299.00.

Example 108

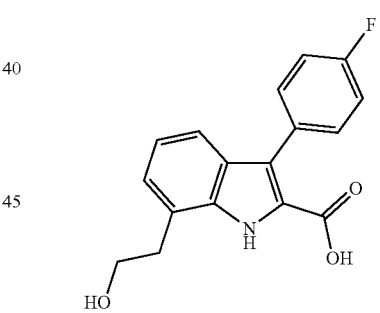

i) Preparation of 2-(2-nitrophenyl)ethyl 2,2-dimethylpropanoate

To a cooled (0° C.) solution of 2-(2-nitrophenyl)ethanol (0.42 ml, 2.99 mmol) and Pyridine (0.48 ml, 5.98 mmol) in DCM (6 mL) under argon was added dropwise trimethylacetyl chloride (0.55 ml, 4.49 mmol). The resulting mixture was stirred at room temperature for 4 h then the mixture partitioned between EtOAc and 1M HCl. The organic extracts were washed with brine, dried over Na$_2$SO$_4$, filtered and concentrated under reduced pressure to give the title compound.

$^1$H NMR (400 MHz, CHLOROFORM-d) δ ppm 7.94-8.05 (1H, m) 7.51-7.62 (1H, m) 7.35-7.48 (2H, m) 4.40 (2H, t, J=6.53 Hz) 3.29 (2H, t, J=6.53 Hz) 1.23-1.32 (1H, m) 1.11-1.20 (9H, m).

ii) Preparation of 2-(2-aminophenyl)ethyl 2,2-dimethylpropanoate

A solution of 2-(2-nitrophenyl)ethyl 2,2-dimethylpropanoate (752 mg, 2.99 mmol) in methanol (60 mL) was hydrogenated using an H-Cube apparatus at 1 mL/min with hydrogen pressure at 20 bar and temperature at 25° C. The resulting solution was concentrated under reduced pressure to afford the title compound.

$^1$H NMR (400 MHz, CHLOROFORM-d) δ ppm 7.01-7.15 (2H, m) 6.65-6.79 (2H, m) 4.20-4.32 (2H, m) 3.87-4.13 (2H, m) 2.79-2.91 (2H, m) 1.16-1.31 (9H, m).

iii) Preparation of ethyl 7-[2-(2,2-dimethylpropanoyloxy)ethyl]-3-(4-fluorophenyl)-1H-indole-2-carboxylate To a solution of ethyl 2-[(4-fluorophenyl)methyl]-3-oxobutanoate (250 mg, 1.05 mmol) in ethanol (2.5 mL) and water (0.5 mL) was added ice (ca. 1 g) followed by KOH (206.05 mg, 3.67 mmol). The resulting mixture was stirred at room temperature for 45 minutes then cooled to 0° C.

In a separate flask, to a cooled (0° C.) solution of 2-(2-aminophenyl)ethyl 2,2-dimethylpropanoate (255.43 mg, 1.15 mmol) in anhydrous THF (2.5 mL) was added dropwise BF$_3$.OEt$_2$ (0.21 ml, 1.73 mmol), followed by dropwise addition of tert-Butyl nitrite (0.16 ml, 1.39 mmol). The resulting mixture was stirred at 0° C. for 45 minutes then the yellow suspension diluted with 1 mL THF and the suspension added dropwise to the prepared enolate solution. The mixture was stirred at room temperature for 1 h concentrated to remove organic solvent then partitioned between EtOAc and water. The aqueous phase was further extracted with EtOAc and the combined organic extracts washed with brine, dried over Na$_2$SO$_4$, filtered and concentrated under reduced pressure.

The residue was taken up HCl in ethanol (prepared from 1.67 mL acetyl chloride added to 3.33 mL cooled ethanol) and heated to reflux for 1.5 h. The mixture was concentrated to low volume and the residue partitioned between EtOAc and sat. aq. NaHCO$_3$. The aqueous phase was further extracted with EtOAc and the combined organic extracts washed with brine, dried over Na$_2$SO$_4$, filtered and concentrated under reduced pressure. The residue was taken up in DCM, adsorbed onto silica and subjected to flash chromatography (Telos 12 g, DCM in heptane, 0-100%) followed by flash chromatography (Telos 12 g, EtOAc in heptane, 0-20%) to give the title compound contaminated with an unknown impurity. The material was used directly in the next step.

iv) Preparation of 3-(4-fluorophenyl)-7-(2-hydroxyethyl)-1H-indole-2-carboxylic acid To a solution of the material obtained above (117 mg) in THF (1.8 mL) and ethanol (0.9 mL) was added 2M NaOH (1.42 ml). The resulting mixture was stirred at room temperature for 48 h and then the mixture treated with 5M HCl (ca. 2 mL) and concentrated to remove organic solvent. The resulting suspension was filtered to collect a crystalline pale yellow solid and the solid washed with water, air dried then further dried under vacuum at 50° C. to give the title compound.

LCMS Method B: =2.73 min, m/z 300.20.

Preparation of Intermediates

Preparation of 1-(4-(4,4,5,5-tetramethyl-1,3,2-dioxaborolan-2-yl)benzyl)-1H-1,2,4-triazole

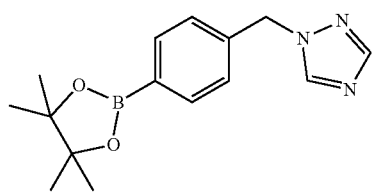 [SMILES: CC1(C)OB(c2ccc(Cn3cncn3)cc2)OC1(C)C]

A mixture of 1-[(4-bromophenyl)methyl]-1,2,4-triazole (177 mg, 0.74 mmol), Bis(pinacolato)diboron (245.42 mg, 0.97 mmol), Pd(dppf)Cl$_2$ (27.2 mg, 0.04 mmol) and Acetic acid, potassium salt (226.18 mg, 2.3 mmol) in dioxane (2.8 mL) and DMSO (0.3 mL) was subjected to microwave irradiation at 150° C. for 30 minutes. The resulting mixture was diluted with water and filtered over celite. The filtrate was extracted with EtOAc (×2) and the combined organic extracts washed with brine (×2), dried over Na$_2$SO$_4$, filtered and concentrated under reduced pressure to give the title compound.

$^1$H NMR (400 MHz, CHLOROFORM-d) δ ppm 8.06 (1H, s) 7.99 (1H, s) 7.84 (2H, d, J=8.03 Hz) 7.24-7.32 (3H, m) 5.32-5.41 (2H, m) 1.34-1.38 (11H, m) 1.27-1.30 (9H, m) 1.26 (4H, s).

Preparation of 1-(4-(4,4,5,5-tetramethyl-1,3,2-dioxaborolan-2-yl)benzyl)-1H-tetrazole

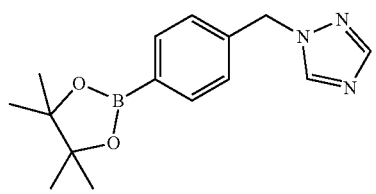 [SMILES: CC1(C)OB(c2ccc(Cn3cncn3)cc2)OC1(C)C]

A mixture of 1-[(4-bromophenyl)methyl]tetrazole (270 mg, 1.13 mmol), Bis(pinacolato)diboron (372.82 mg, 1.47 mmol), Pd(dppf)Cl$_2$ (41.32 mg, 0.06 mmol) and Acetic acid, potassium salt (343.59 mg, 3.5 mmol) in dioxane (6 mL) and DMSO (0.6 mL) was subjected to microwave irradiation at 150° C. for 30 minutes. The resulting mixture was diluted with water and filtered over celite. The filtrate was extracted with EtOAc and the combined organic extracts washed with brine (×2), dried over Na$_2$SO$_4$, filtered and concentrated under reduced pressure to give the title compound with some unidentified impurities. The material was used without further purification.

$^1$H NMR (400 MHz, CHLOROFORM-d) δ ppm 8.49 (1H, s) 7.87 (2H, d, J=8.03 Hz) 7.31 (2H, d, J=7.78 Hz) 5.62 (2H, s) 1.37 (13H, s) 1.27-1.30 (16H, m) 1.26 (6H, s).

Preparation of 2-(2-phenoxyethyl)aniline

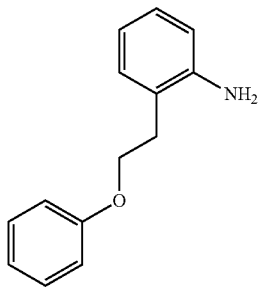 [SMILES: Nc1ccccc1CCOc1ccccc1]

i) Preparation of 1-nitro-2-(2-phenoxyethyl)benzene

To a cooled (0° C.) solution of 2-(2-nitrophenyl)ethanol (0.58 ml, 4.12 mmol), Phenol (310 mg, 3.29 mmol) and Triphenyl phosphine (1295.95 mg, 4.94 mmol) in THF (7.5 mL) was added dropwise DIAD (0.97 ml, 4.94 mmol). The resulting mixture was stirred at room temperature for 64 h. The mixture was concentrated under reduced pressure. The material was subjected to flash chromatography (Biotage 25 g, EtOAc in heptane, 0-20 then 20-50%) to give the title compound.

$^1$H NMR (400 MHz, CHLOROFORM-d) δ ppm 7.97 (1H, dd, J=8.16, 0.88 Hz) 7.54-7.60 (1H, m) 7.48-7.54 (1H, m) 7.39-7.46 (1H, m) 7.24-7.33 (3H, m) 6.96 (1H, t, J=7.28 Hz) 6.90 (2H, d, J=7.78 Hz) 4.24-4.35 (2H, m) 3.42 (2H, t, J=6.27 Hz).

ii) Preparation of 2-(2-phenoxyethyl)aniline

A solution of 1-nitro-2-(2-phenoxyethyl)benzene (836 mg, 3.44 mmol) in methanol (69 mL) was hydrogenated using the H-Cube apparatus with a Pd/C 10% cartridge at 1 mL/min with hydrogen pressure at 20 bar and temperature at 40° C. after 15 minutes the temperature was raised to 50° C. and recycled until starting material had been consumed. The resulting solution was concentrated under reduced pressure to give the title compound.

$^1$H NMR (400 MHz, CHLOROFORM-d) δ ppm 7.23-7.34 (3H, m) 7.05-7.15 (2H, m) 6.96 (1H, t, J=7.40 Hz) 6.91 (2H, d, J=8.03 Hz) 6.71-6.82 (2H, m) 4.23 (2H, t, J=6.65 Hz) 3.80-4.09 (2H, m) 2.99-3.08 (2H, m).

Preparation of 3-chloro-N,N-dimethyl-4-(4,4,5,5-tetramethyl-1,3,2-dioxaborolan-2-yl)benzamide

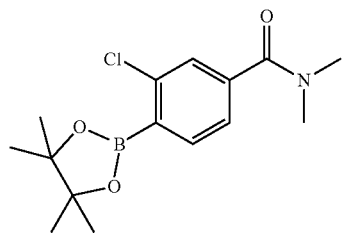

i) Preparation of 4-bromo-3-chloro-N,N-dimethyl-benzamide

A mixture of 4-bromo-3-chloro-benzoic acid (250 mg, 1.06 mmol), TEA (0.64 ml, 4.57 mmol), EDC HCl (264.6 mg, 1.38 mmol) and HOBT (211.37 mg, 1.38 mmol) in DCM (4 mL) was stirred at room temperature for 30 minutes prior to addition of 2M Dimethylamine (0.9 ml). The resulting mixture was stirred at room temperature for 20 h. The mixture was heated to 50° C. for 24 h (additional 2M Dimethylamine (0.9 ml) added after 7 h). The mixture was partitioned between brine and DCM and the aqueous phase further extracted with EtOAc. The combined organic extracts were dried over $Na_2SO_4$, filtered and concentrated under reduced pressure. The residue was subjected to flash chromatography (Telos 12 g, EtOAc in heptane, 0-50%) to give the title compound.

$^1$H NMR (400 MHz, CHLOROFORM-d) δ ppm 7.64-7.69 (1H, m) 7.54 (1H, d, J=1.76 Hz) 7.19 (1H, dd, J=8.03, 2.01 Hz) 3.11 (3H, br. s.) 3.00 (3H, br. s.).

ii) Preparation of 3-chloro-N,N-dimethyl-4-(4,4,5,5-tetramethyl-1,3,2-dioxaborolan-2-yl)benzamide A mixture of 4-bromo-3-chloro-N,N-dimethyl-benzamide (69 mg, 0.26 mmol), Bis(pinacolato)diboron (76.75 mg, 0.3 mmol), Pd(dppf)Cl$_2$ (9.62 mg, 0.01 mmol) and Acetic acid, potassium salt (77.38 mg, 0.79 mmol) in dioxane (1.8 mL) and DMSO (0.2 mL) was purged with argon then subjected to microwave irradiation at 150° C. for 30 minutes. The mixture was filtered over Celite™, rinsing with EtOAc and the filtrate partitioned between EtOAc and brine. The aqueous phase was further extracted with EtOAc and the combined organic extracts washed with brine (×2), dried over $Na_2SO_4$, filtered and concentrated under reduced pressure to give the title compound.

$^1$H NMR (400 MHz, CHLOROFORM-d) δ ppm 7.71 (1H, d, J=7.53 Hz) 7.39 (1H, d, J=1.00 Hz) 7.23-7.28 (1H, m) 3.09 (3H, s) 2.89-2.98 (3H, m) 1.31-1.41 (12H, m) 1.20-1.30 (25H, m).

Biological Activity

The biological activity of the compounds of the present invention was tested using standard assay protocols.[7] The following representative enzymes NDM-1 (New Delhi metallo-β-lactamase-1), IMP-1 (Imipenemase-1) and VIM-2 (Veronese metallo-β-lactamase-2) were selected from different clinically relevant B1 metallo-β-lactamases.

TABLE 1 pIC$_{50}$ values of Indole carboxylates and derivatives against NDM-1, VIM-2 and IMP-1.

| Example | pIC$_{50}$ VIM-2 | pIC$_{50}$ IMP-1 | pIC$_{50}$ NDM-1 |
|---|---|---|---|
| 1 | 7 | 5.7 | 7.6 |
| 2 | 6.4 | 5.1 | 7.3 |
| 3 | >8.3 | 5.3 | 7.4 |
| 4 | 6.2 | 4.9 | 7.2 |
| 5 | 7 | 5.1 | 7.5 |
| 6 | 6.5 | 5 | 7.8 |
| 7 | 6.7 | 5.1 | 7.4 |
| 8 | 6.6 | 4.6 | 7.1 |
| 9 | 6.6 | 5.1 | 7.3 |
| 10 | 6.7 | 5.1 | 7.6 |
| 11 | 6.5 | 4.9 | 7.5 |
| 12 | 6.5 | 4.9 | 7.9 |
| 13 | 5.8 | 5 | 7.9 |
| 14 | 6.1 | 4.7 | 7.3 |

TABLE 1-continued pIC$_{50}$ values of Indole carboxylates and derivatives against NDM-1, VIM-2 and IMP-1.

| Example | pIC$_{50}$ VIM-2 | pIC$_{50}$ IMP-1 | pIC$_{50}$ NDM-1 |
|---|---|---|---|
| 15 | 6.9 | 4.8 | 7.6 |
| 16 | 6.1 | 4.9 | 7.3 |
| 17 | 6.3 | <4 | 6.7 |
| 18 | 7.3 | 5.7 | 7.7 |
| 19 | 7 | 5.3 | 7.5 |
| 20 | 6.7 | 4.1 | 6.9 |
| 21 | 6.9 | <4 | 6.9 |
| 22 | 5.9 | <4 | 6.9 |
| 23 | 6 | 5.1 | 7.5 |
| 24 | 6.2 | 4.9 | 7 |
| 25 | 5.7 | 5.3 | 7.5 |
| 26 | 5.6 | 4.4 | 7 |
| 27 | | | 7.1 |
| 28 | 6.5 | 4.6 | 7.2 |
| 29 | 6.6 | 6.1 | 8.3 |
| 30 | 6.8 | 5.6 | 7.7 |
| 31 | 7.4 | 4.2 | 7.2 |
| 32 | 7.1 | 4.9 | 7.6 |
| 33 | 6.6 | 5.7 | 8.3 |
| 34 | 6.7 | 7.3 | 5 |
| 35 | 4.7 | 4.7 | 6.3 |
| 36 | 4.4 | <4 | 6.4 |
| 37 | 6.4 | 5 | 7.5 |
| 38 | 6.8 | 4.7 | 7.4 |
| 39 | 6.9 | N.R. | 6.9 |
| 40 | 6.6 | 5.8 | 7.8 |
| 41 | 6.6 | 5.8 | 6.5 |
| 42 | 6.6 | 5 | 7.8 |
| 43 | 6.8 | 4.9 | 7.5 |
| 44 | 6.7 | 5.4 | 7.5 |
| 45 | 6.5 | 5.4 | 7.5 |
| 46 | N.R. | N.R. | 6.2 |
| 47 | 5.1 | 4.3 | 6.4 |
| 48 | 5.4 | <4 | 6.2 |
| 49 | 6.3 | 4.8 | 7.5 |
| 50 | 6 | 4.6 | 6.6 |
| 51 | | 5.7 | 6.6 |
| 52 | 6.5 | 6.5 | 7.7 |
| 53 | 7.5 | 6.3 | 7.9 |
| 54 | 6.1 | 4.5 | 6.6 |
| 55 | 6.4 | 5.7 | 7.6 |
| 56 | 6.4 | 5.1 | 7.5 |
| 57 | 7 | 7 | 7.1 |
| 58 | 6.1 | 4.8 | 7.5 |
| 59 | 6.3 | 4.6 | 6.9 |
| 60 | 6.2 | <4 | 6.9 |
| 61 | 6.5 | 5.9 | 7.5 |
| 62 | 6.8 | 6.5 | 8.3 |
| 63 | 6 | <4 | 6.5 |
| 64 | 6.3 | 5.8 | 7.8 |
| 65 | 7.9 | 7.5 | 8.8 |
| 66 | 7.5 | 7.5 | 8.3 |
| 67 | 7.7 | 7.4 | 8.6 |
| 68 | 7.5 | 7.4 | 8.2 |
| 69 | 8.1 | 7.9 | 8.6 |
| 70 | 7.1 | 8 | 8.6 |
| 71 | 7.7 | 7.4 | 8.4 |
| 72 | 7.9 | 5.6 | 7.3 |
| 73 | 7.5 | 7.5 | 9.45 |
| 74 | 7.1 | 7.7 | 9.25 |
| 75 | 8 | 7.6 | 8.7 |
| 76 | 8.4 | 7.8 | 8.1 |
| 77 | 8.2 | 4.9 | 6.7 |
| 78 | 8.4 | 6.9 | 8 |
| 79 | 8.4 | 7.8 | 9.3 |
| 80 | 8 | 7.7 | 9.2 |
| 81 | 7.2 | 7 | 8.8 |
| 82 | 6.8 | 6.3 | 8.4 |
| 83 | 7 | 7.2 | 8.4 |
| 84 | 7.7 | 6.2 | 7.43 |
| 85 | 6.8 | 6 | 7 |
| 86 | 6.24 | 6.19 | 8.13 |
| 87 | NA | 7.11 | 7.9 |
| 88 | 7.99 | 7.27 | 8.37 |
| 89 | NA | 7.67 | 7.57 |
| 90 | NA | 7.21 | 7.9 |
| 91 | 8.14 | 7.35 | 8.47 |
| 92 | NA | 7.1 | 7.27 |
| 93 | NA | 7.07 | 7.1 |
| 94 | 6.98 | 6.98 | 8.23 |
| 95 | NA | 7.62 | 8.57 |
| 96 | NA | 8.11 | 8.4 |
| 97 | NA | 6.36 | 8 |
| 98 | NA | 6.66 | 8.17 |
| 99 | NA | 8.08 | 9.07 |
| 100 | NA | 7.65 | 7.8 |
| 101 | NA | 5.81 | 7.8 |
| 102 | 6.39 | 4.88 | 8 |
| 103 | 5.5 | 4.1 | 7.1 |
| 104 | 4.9 | 4.3 | 6.6 |
| 105 | 5.6 | 4.5 | 6.8 |
| 106 | 7.3 | 6.3 | 7.9 |
| 107 | 5.8 | 5.4 | 6.2 |
| 108 | 6.1 | 5.5 | 7.3 |
| 109 | N.R. | N.R. | 5.5 |
| 110 | N.R. | N.R. | 5.7 |
| 111 | N.R. | N.R. | 4.7 |
| 112 | 5.1 | 4 | 5.8 |
| 113 | N.R. | N.R. | 5.1 |
| 114 | | | 5.5 |
| 115 | N.R. | N.R. | 5.8 |
| 116 | 7.4 | <4 | 5.9 |
| 117 | 6.7 | <4 | 5.9 |
| 118 | | <4 | 4.8 |
| 119 | 4.8 | 4.1 | 5.7 |
| 120 | 4.5 | <4 | <4.7 |
| 121 | 4.4 | 4.7 | 5.2 |
| 122 | <4.7 | <4.7 | 4.7 |
| 123 | N.I. | N.I. | N.I. |
| 124 | N.I. | N.I. | N.I. |
| 125 | NF | NF | N.I. |
| 126 | NF | NF | N.I. |
| 127 | N.I. | N.I. | 6.4 |
| 128 | NF | NF | 6.67 |

In-Vitro Cell Based Work

Meropenem MICs were determined using the CLSI broth microdilution protocol (Ref: Clinical and Laboratory Standards Institute. 2012. *Methods for dilution antimicrobial susceptibility tests for bacteria that grow aerobically;* 9th ed. Approved standard M07-A9.

CLSI, Wayne, Pa.) in the absence of each inhibitor or in its presence at the concentration stated. In each case the inhibitor solution was added to broth at 0.1% v/v to achieve the required final concentration; DMSO was used to dissolve inhibitors. The MIC is defined as the concentration of meropenem required to totally inhibit growth, as evidenced by an absence of optical density at 600 nm measured spectrophotometrically (Spectra Max 190; Molecular Devices, Wokingham, United Kingdom).

For initial evaluations of the in vitro cell based activity of indole carboxylates we used well characterized bacterial strains (e.g. *K. pneumoniae* 5055; *E. coli* ATCC 25713) transformed with broad host range plasmids (e.g. pSU18 and derivatives) encoding few metallo-β-lactamases produced using their physiological (integron) promoters. We also tested a clinical strain, IR60 in the initial studies.[8]

TABLE 2

Screening of Examples 53, 6 and 12 against a panel of well characterized bacterial strains.

| | Meropenem MICs | Example 53 (10 μg/ml) | Example 6 (10 μg/ml) | Example 12 (10 μg/ml) |
|---|---|---|---|---|
| E. coli 25922 (control) | <0.25 | <0.25 | <0.25 | <0.25 |
| E. coli IR60 | 8 | <0.25 | <0.25 | <0.5 |
| K. pneumoniae 5055 (control) | <0.25 | <0.25 | <0.25 | <0.25 |
| K. pneumoniae 5055 + NDM-1 | >128 | 4 | 1 | 8 |

IR60 is a clinically strain original from India.[8] IR60 is also a multiresistant clinical strain.

The results shown in Table 2 reveal that compounds of formula (I) are active in cells, including clinically relevant bacterial strains. Further studies were carried out to determine if compound of formula (I) potentiates BLA activity in clinically derived strains containing IMP-4, VIMP-4 or NDM-1, which are the most commonly observed MBLs in clinical isolates. All strains producing MBLs were confirmed as resistant to meropenem at the Clinical and Laboratory Standards Institute (U.S.A.) defined breakpoint.

TABLE 3

Screening of Examples 53, 6 and 12 against a panel of well characterized clinically derived strains.

| | Meropenem | Example 53 (10 μg/ml) | Example 6 (10 μg/ml) | Example 12 (10 μg/ml) |
|---|---|---|---|---|
| E. coli EC10 NDM-1 | 128 | 1 | 8 | 8 |
| K. pneumoniae IR16 NDM-1 | 16 | 1 | 2 | 1 |
| K. pneumoniae 5055 IMP-1 | 16 | 2 | 8 | 8 |
| K. pneumoniae B12 IMP-4 | 16 | 2 | 16 | 8 |
| K. pneumoniae B19 IMP-4 | 16 | 1 | 8 | 8 |
| K. pneumoniae A34 VIM-4 | 64 | 4 | 16 | 16 |

Other compounds of formula (I) were also screened against on K. pneumonia strain containing most clinically significant MBLs (see Table 4.) By using of example of the utility of the compounds, example 76 shows good activity against all the MBLs.

TABLE 4

Screening of various inhibitor against K. pneumoniae (RamA version, breakpoint <= 1 mg/L) that also co-express various MBLs (inhibitor concentration 25 mg/mL)

| EXAMPLE | CONT | IMP-1 | VIM-1 | NDM-1 |
|---|---|---|---|---|
| DMSO | <= 0.0625 | 16 | 32 | 32 |
| 53 | <= 0.0625 | 1 | 2 | 0.5 |
| 6 | <= 0.0625 | 4 | 2 | 1 |
| 12 | <= 0.0625 | 16 | 8 | 4 |
| 77 | <= 0.0625 | 16 | 8 | 16 |
| 68 | <= 0.0625 | 1 | 8 | 0.5 |
| 69 | <= 0.0625 | 4 | 16 | 1 |
| 76 | <= 0.0625 | 0.25 | <=0.0625 | <=0.0625 |
| 75 | <= 0.0625 | 1 | 4 | 0.5 |
| 73 | <= 0.0625 | 4 | 8 | 1 |
| 18 | <= 0.0625 | 4 | 8 | 2 |
| 70 | <= 0.0625 | 2 | 8 | 1 |
| 33 | <= 0.0625 | 2 | 8 | 4 |
| 74 | <= 0.0625 | 2 | 8 | 0.25 |
| 62 | <= 0.0625 | 4 | 2 | 4 |
| 65 | <= 0.0625 | 4 | 2 | 0.5 |
| 34 | <= 0.0625 | 2 | 8 | 0.5 |

While specific embodiments of the invention have been described for the purpose of reference and illustration, various modifications will be apparent to a person skilled in the art without departing from the scope of the invention as defined by the appended claims.

REFERENCES

1. J. Antibiot., 2013, 66, 571-591.
2. Clin. Microbiol. Rev., 2005, 18, 306-325.
3. Antimicrob. Agents Chemother., 2010, 54, 969-976.
4. Expert Opin. Ther. Pat., 2013, 23, 1469-1481.
5. a) http://www.who.int/en/; b) https://www.gov.uk/; c) http://www.cdc.gov.
6. J. Hospit. Infect., 2015, 89, 241-247.
7. J Med Chem 56:6945-6953
8. Antimicrob. Agents Chemother., 2011, 55, 3635-3636 (http://aac.asm.org/content/55/7/3635.full.pdf)

The invention claimed is:

1. A compound of formula I, or a pharmaceutically acceptable salt or solvate thereof, as shown below:

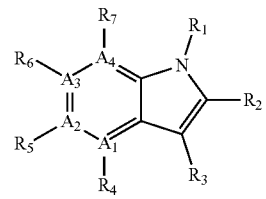

wherein
$A_1$, $A_2$, $A_3$ and $A_4$ are C;
$R_1$ is hydrogen;
$R_2$ is —C(O)OH;
$R_3$ is selected from aryl, (3-8C)cycloalkyl, heteroaryl or heterocyclyl, wherein said aryl, (3-8C)cycloalkyl, heteroaryl or heterocyclyl is substituted by one or more $R^B$;
wherein $R^B$ is halo, cyano, nitro, hydroxy or a group:

—$Y^3$—$X^3$—$Z^3$ wherein
$Y^3$ is absent or a linker group of the formula —$[CR^{B1}R^{B2}]_n$— in which n is an integer selected from 1 or 2 and $R^{B1}$ and $R^{B2}$ are each independently selected from hydrogen or methyl;
$X^3$ is absent or —O—, —C(O)—, —C(O)O—, —OC(O)—, —N($R^{B3}$)—, —N($R^{B4}$)—C(O)—, —N($R^{B4}$)—C(O)O—, —C(O)—N($R^{B3}$)—, —SO$_2$—, —S(O)$_2$N($R^{B3}$)—, or —N($R^{B4}$)SO$_2$— wherein $R^{B3}$ and $R^{B4}$ are each independently selected from hydrogen or methyl; and $Z^3$ is (1-6C)alkyl, aryl, heteroaryl or heterocyclyl; and wherein $Z^3$ is optionally further substituted by one or more substituent groups independently selected from oxo, halo, cyano, hydroxy, carboxy, NR$^{B5}$R$^{B6}$, (1-4C)alkoxy or (1-4C)alkyl;

R$_4$ is hydrogen;
R$_5$ is hydrogen;
R$_6$ is hydrogen;
R$_7$ is selected from cyano, hydroxy or a group

—Y$^7$—X$^7$—Z$^7$ wherein:
Y$^7$ is absent or a linker group of the formula —[CR$^{7A}$R$^{7B}$]$_q$— in which q is an integer selected from 1, 2 or 3, and R$^{7A}$ and R$^{7B}$ are each independently selected from hydrogen or (1-2C)alkyl;

X$^7$ is absent or —O—, —C(O)—, —C(O)O—, —OC(O)—, —N(R$^{7C}$)—, —N(R$^{7D}$)—C(O)—, —N(R$^{7D}$)—C(O)O—, —C(O)—N(R$^{7C}$)—, —S—, —SO—, —SO$_2$—, —S(O)$_2$N(R$^{7C}$)—, or —N(R$^{7D}$)SO$_2$— wherein R$^{7C}$ and R$^{7D}$ are each independently selected from hydrogen or methyl; and Z$^7$ is (2-6C)alkyl, (2-6C)alkenyl, (2-6C)alkynyl, aryl, (3-6C)cycloalkyl, (3-6C)cycloalkenyl, heteroaryl or heterocyclyl;

and wherein Z$^7$ is optionally further substituted by one or more substituent groups independently selected from oxo, halo, cyano, nitro, hydroxy, carboxy, NR$^{7E}$R$^{7F}$, (1-4C)alkoxy, (1-4C)alkyl, (3-8C)cycloalkyl, (3-8C)cycloalkyl-(1-3C)alkyl, aryl, aryl-(1-2C)alkyl, heterocyclyl, heterocyclyl-(1-2C)alkyl, heteroaryl, heteroaryl-(1-2C)alkyl, C(O)NR$^{7E}$R$^{7F}$, NR$^{7E}$C(O)R$^{7F}$, NR$^{7E}$S(O)$_2$R$^{7F}$ and S(O)$_2$NR$^{7E}$R$^{7F}$; wherein R$^{7E}$ and R$^{7F}$ are each independently selected from hydrogen or (1-4C)alkyl; or R$^{7E}$ and R$^{7F}$ can be linked such that, together with the nitrogen atom to which they are attached, they form a 4-7 membered heterocyclic ring;

and wherein any alkyl, aryl, heterocyclyl or heteroaryl group present in a substituent group on Z$^7$ is optionally further substituted by halo, cyano, nitro, hydroxy, carboxy, NR$^{7G}$R$^{7H}$, (1-2C)alkoxy, or (1-2C)alkyl; wherein R$^{7G}$ and R$^{7H}$ are selected from hydrogen or (1-2C)alkyl;

or R$^{7C}$ and Z$^7$ can be linked such that, together with the nitrogen atom to which they are attached, they form a 4-7 membered heterocyclic ring, which is optionally substituted by oxo, halo, cyano, nitro, hydroxy, carboxy, NR$^{7E}$R$^{7F}$, (1-4C)alkoxy or (1-4C)alkyl.

2. A compound according to claim 1, or a pharmaceutically acceptable salt or solvate thereof, wherein R$_3$ is selected from aryl, (3-8C)cycloalkyl, heteroaryl or heterocyclyl, wherein said aryl, (3-8C)cycloalkyl, heteroaryl or heterocyclyl is substituted by one or more R$^B$; and wherein R$^B$ is halo, cyano, nitro, hydroxy or a group:

—Y$^3$—X$^3$—Z$^3$ wherein
Y$^3$ is absent or a linker group of the formula —[CR$^{B1}$R$^{B2}$]$_n$— in which n is 1 and R$^{B1}$ and R$^{B2}$ are each hydrogen;

X$^3$ is absent or —O—, —C(O)O—, —N(R$^{B3}$)—, —N(R$^{B4}$)—C(O), —C(O)—N(R$^{B3}$)—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and Z$^3$ is (1-6C)alkyl, aryl, heteroaryl or heterocyclyl;

and wherein Z$^3$ is optionally further substituted by one or more substituent groups independently selected from oxo, halo or (1-4C)alkyl.

3. A compound according to claim 1, or a pharmaceutically acceptable salt or solvate thereof, wherein R$_3$ is selected from aryl, heteroaryl or heterocyclyl, wherein said aryl, heteroaryl or heterocyclyl is substituted by one or more R$^B$; and R$^B$ is halo, cyano, nitro, or a group:

—Y$^3$—X$^3$—Z$^3$ wherein
Y$^3$ is absent or a linker group of the formula —[CR$^{B1}$R$^{B2}$]$_n$— in which n is 1 and R$^{B1}$ and R$^{B2}$ are hydrogen;

X$^3$ is absent or —O—, —C(O)O—, —N(R$^{B3}$)—, —N(R$^{B4}$)—C(O), —C(O)—N(R$^{B3}$)—, —SO$_2$— or —S(O)$_2$N(R$^{B3}$)—, or —N(R$^{B4}$)SO$_2$—; wherein R$^{B3}$ and R$^{B4}$ are each independently selected from hydrogen or methyl; and Z$^3$ is (1-6C)alkyl, aryl, heteroaryl or heterocyclyl;

and wherein Z$^3$ is optionally further substituted by one or more substituent groups independently selected from oxo, halo or (1-4C)alkyl.

4. A compound according to claim 1, wherein R$_7$ is selected from cyano, hydroxy or a group

—Y$^7$—X$^7$—Z$^7$ wherein:
Y$^7$ is absent or a linker group of the formula —[CR$^{7A}$R$^{7B}$]$_q$— in which q is an integer selected from 1, 2 or 3, and R$^{7A}$ and R$^{7B}$ are each independently selected from hydrogen or (1-2C)alkyl;

X$^7$ is absent or —O—, —C(O)—, —C(O)O—, —OC(O)—, —N(R$^{7C}$)—, —N(R$^{7D}$)—C(O)—, —C(O)—N(R$^{7C}$)—, —SO$_2$—, —S(O)$_2$N(R$^{7C}$)—, or —N(R$^{7D}$)SO$_2$—; wherein R$^{7C}$ and R$^{7D}$ are each independently selected from hydrogen or methyl; and Z$^7$ is (2-6C)alkyl, (2-6C)alkenyl, (2-6C)alkynyl, aryl, (3-6C)cycloalkyl, (3-6C)cycloalkenyl, heteroaryl or heterocyclyl;

and wherein Z$^7$ is optionally further substituted by one or more substituent groups independently selected from oxo, halo, cyano, nitro, hydroxy, carboxy, NR$^{7E}$R$^{7F}$, (1-4C)alkoxy, (1-4C)alkyl, (3-8C)cycloalkyl, aryl, heterocyclyl, heteroaryl, C(O)NR$^{7E}$R$^{7F}$ or NR$^{7E}$C(O)R$^{7F}$; wherein R$^{7E}$ and R$^{7F}$ are each independently selected from hydrogen or (1-4C)alkyl; or R$^{7E}$ and R$^{7F}$ can be linked such that, together with the nitrogen atom to which they are attached, they form a 4-6 membered heterocyclic ring;

and wherein any alkyl, aryl, heterocyclyl or heteroaryl group present in a substituent group on Z$^7$ is optionally further substituted by halo, cyano, nitro, hydroxy, carboxy, NR$^{7G}$R$^{7H}$, (1-2C)alkoxy, or (1-2C)alkyl; wherein $R^{7G}$ and $R^{7H}$ are selected from hydrogen or (1-2C)alkyl.

5. A compound selected from any one of the following, or a pharmaceutically acceptable salt thereof:

3-(3-chlorophenyl)-7-methyl-1H-indole-2-carboxylic acid
7-methyl-3-(4-(trifluoromethoxy)phenyl)-1H-indole-2-carboxylic acid
3-(3,5-dichlorophenyl)-7-methyl-1H-indole-2-carboxylic acid
7-methyl-3-(pyridin-4-yl)-1H-indole-2-carboxylic acid
3-(4-carbamoylphenyl)-7-methyl-1H-indole-2-carboxylic acid
7-methyl-3-(4-sulfamoylphenyl)-1H-indole-2-carboxylic acid
3-(4-cyanophenyl)-7-methyl-1H-indole-2-carboxylic acid
7-methyl-3-(4-nitrophenyl)-1H-indole-2-carboxylic acid
3-(4-methoxyphenyl)-7-methyl-1H-indole-2-carboxylic acid
3-(4-bromophenyl)-7-methyl-1H-indole-2-carboxylic acid
7-methyl-3-(4-(trifluoromethyl)phenyl)-1H-indole-2-carboxylic acid
7-methyl-3-(4-(methylsulfonyl)phenyl)-1H-indole-2-carboxylic acid
7-methyl-3-(4-morpholinophenyl)-1H-indole-2-carboxylic acid
7-methyl-3-(3-sulfamoylphenyl)-1H-indole-2-carboxylic acid
7-methyl-3-(3-nitrophenyl)-1H-indole-2-carboxylic acid
7-methyl-3-(3-(methylsulfonyl)phenyl)-1H-indole-2-carboxylic acid
3-(3-(dimethylamino)phenyl)-7-methyl-1H-indole-2-carboxylic acid
3-(3-bromophenyl)-7-methyl-1H-indole-2-carboxylic acid
3-(1H-indazol-5-yl)-7-methyl-1H-indole-2-carboxylic acid
3-(2-methoxyphenyl)-7-methyl-1H-indole-2-carboxylic acid
3-([1,2,4]triazolo[1,5-a]pyridin-7-yl)-7-methyl-1H-indole-2-carboxylic acid
7-methyl-3-(pyrimidin-5-yl)-1H-indole-2-carboxylic acid
3-(4-aminophenyl)-7-methyl-1H-indole-2-carboxylic acid
7-methyl-3-(pyridin-3-yl)-1H-indole-2-carboxylic acid
3-(1-(tert-butoxycarbonyl)-1,2,3,6-tetrahydropyridin-4-yl)-7-methyl-1H-indole-2-carboxylic acid
7-methyl-3-(1-methyl-1H-pyrazol-4-yl)-1H-indole-2-carboxylic acid
3-(2-cyanophenyl)-7-methyl-1H-indole-2-carboxylic acid
3-(4-(N,N-dimethylsulfamoyl)phenyl)-7-methyl-1H-indole-2-carboxylic acid
3-(4-acetamidophenyl)-7-methyl-1H-indole-2-carboxylic acid
3-(1H-indazol-4-yl)-7-methyl-1H-indole-2-carboxylic acid
3-(1H-indazol-6-yl)-7-methyl-1H-indole-2-carboxylic acid
3-(4-((1H-1,2,4-triazol-1-yl)methyl)phenyl)-7-methyl-1H-indole-2-carboxylic acid
3-(4-((1H-pyrazol-1-yl)methyl)phenyl)-7-methyl-1H-indole-2-carboxylic acid
3-(4-chlorophenyl)-1,7-dimethyl-1H-indole-2-carboxylic acid
3-(3,5-dimethylphenyl)-7-methyl-1H-indole-2-carboxylic acid
3-(2-chlorophenyl)-7-methyl-1H-indole-2-carboxylic acid
3-([1,1'-biphenyl]-4-yl)-7-methyl-1H-indole-2-carboxylic acid
7-methyl-3-(o-tolyl)-1H-indole-2-carboxylic acid
3-(4-chlorophenyl)-7-methyl-1H-indole-2-carboxylic acid
3-(4-chloro-3-(trifluoromethyl)phenyl)-7-methyl-1H-indole-2-carboxylic acid
7-methyl-3-(3-(trifluoromethyl)phenyl)-1H-indole-2-carboxylic acid
3-(4-cyclopropylphenyl)-7-methyl-1H-indole-2-carboxylic acid
3-iodo-7-methyl-1H-indole-2-carboxylic acid
3-(4-fluorophenyl)-7-methoxy-1H-indole-2-carboxylic acid
3-(4-fluorophenyl)-7-(trifluoromethyl)-1H-indole-2-carboxylic acid
3-(4-fluorophenyl)-7-propyl-1H-indole-2-carboxylic acid
3-(4-fluorophenyl)-7-isopropyl-1H-indole-2-carboxylic acid
7-chloro-3-(4-fluorophenyl)-1H-indole-2-carboxylic acid
7-(tert-butyl)-3-(4-fluorophenyl)-1H-indole-2-carboxylic acid
3-(4-fluorophenyl)-7-(2-methoxyethyl)-1H-indole-2-carboxylic acid
3-(4-fluorophenyl)-7-(2-phenoxyethyl)-1H-indole-2-carboxylic acid
7-methyl-3-(pyridin-2-yl)-1H-indole-2-carboxylic acid
7-isopropyl-3-(4-sulfamoylphenyl)-1H-indole-2-carboxylic acid
7-isopropyl-3-phenyl-1H-indole-2-carboxylic acid
7-isopropyl-3-(4-(methylsulfonyl)phenyl)-1H-indole-2-carboxylic acid
7-isopropyl-3-(pyridin-4-yl)-1H-indole-2-carboxylic acid
3-(4-carbamoylphenyl)-7-isopropyl-1H-indole-2-carboxylic acid
7-isopropyl-3-(4-morpholinophenyl)-1H-indole-2-carboxylic acid
3-(4-chlorophenyl)-7-isopropyl-1H-indole-2-carboxylic acid
3-(2-chlorophenyl)-7-isopropyl-1H-indole-2-carboxylic acid
3-(4-(N,N-dimethylsulfamoyl)phenyl)-7-isopropyl-1H-indole-2-carboxylic acid
3-(4-(dimethylcarbamoyl)phenyl)-7-isopropyl-1H-indole-2-carboxylic acid
3-(1H-indazol-5-yl)-7-isopropyl-1H-indole-2-carboxylic acid
3-(3,5-dichlorophenyl)-7-isopropyl-1H-indole-2-carboxylic acid
3-(2,3-dimethoxyphenyl)-7-isopropyl-1H-indole-2-carboxylic acid
3-(3,5-difluorophenyl)-7-isopropyl-1H-indole-2-carboxylic acid
3-(4-((1H-pyrazol-1-yl)methyl)phenyl)-7-isopropyl-1H-indole-2-carboxylic acid
3-(4-((1H-1,2,4-triazol-1-yl)methyl)phenyl)-7-isopropyl-1H-indole-2-carboxylic acid
3-(4-(N,N-dimethylsulfamoyl)phenyl)-7-(2-phenoxyethyl)-1H-indole-2-carboxylic acid
3-(4-(dimethylcarbamoyl)phenyl)-7-(2-phenoxyethyl)-1H-indole-2-carboxylic acid
3-(4-chlorophenyl)-7-(2-phenoxyethyl)-1H-indole-2-carboxylic acid 7-isopropyl-3-(4-(methylcarbamoyl)phenyl)-1H-indole-2-carboxylic acid 7-isopropyl-3-(4-(N-methylsulfamoyl)phenyl)-1H-indole-2-carboxylic acid 7-isopropyl-3-(5-methylthiophen-2-yl)-1H-indole-2-carboxylic acid 3-(4-(acetamidomethyl)phenyl)-7-isopropyl-1H-indole-2-carboxylic acid 3-(4-carboxyphenyl)-7-isopropyl-1H-indole-2-carboxylic acid 7-(tert-butyl)-3-(4-(dimethylcarbamoyl)phenyl)-1H-indole-2-carboxylic acid 7-(tert-butyl)-3-(4-(N,N-dimethylsulfamoyl)phenyl)-1H-indole-2-carboxylic acid 7-isopropyl-3-(4-(morpholinomethyl)phenyl)-1H-indole-2-carboxylic acid 7-isopropyl-3-(4-(morpholinosulfonyl)phenyl)-1H-indole-2-carboxylic acid 7-isopropyl-3-(4-(methylsulfonamidomethyl)phenyl)-1H-indole-2-carboxylic acid 3-(4-((dimethylamino)methyl)phenyl)-7-isopropyl-1H-indole-2-carboxylic acid 7-isopropyl-3-(6-morpholinopyridin-3-yl)-1H-indole-2-carboxylic acid 7-isopropyl-3-(4-(pyrrolidin-1-ylsulfonyl)phenyl)-1H-indole-2-carboxylic acid 3-(2-chloro-4-(dimethylcarbamoyl)phenyl)-7-isopropyl-1H-indole-2-carboxylic acid 4-(7-isopropyl-2-(1H-tetrazol-5-yl)-1H-indol-3-yl)-N,N-dimethylbenzenesulfonamide 3-cyclohexyl-7-methyl-1H-indole-2-carboxylic acid 3-(1-(tert-butoxycarbonyl)piperidin-4-yl)-7-methyl-1H-indole-2-carboxylic acid 7-cyclopropyl-3-(4-fluorophenyl)-1H-indole-2-carboxylic acid 3-(4-fluorophenyl)-7-(2-hydroxyethyl)-1H-indole-2-carboxylic acid 3-(4-fluorophenyl)-7-methyl-N'-(4-(methylsulfonyl)phenyl)-1H-indole-2-carbohydrazide 1-methyl-3-phenyl-1H-indole-2-carboxylic acid 7-fluoro-3-(4-fluorophenyl)-1H-indole-2-carboxylic acid 3-(2,3-dimethoxyphenyl)-7-methyl-1H-indole-2-carboxylic acid 3-(3,5-dimethylisoxazol-4-yl)-7-methyl-1H-indole-2-carboxylic acid 3-(4-(N,N-dimethylsulfamoyl)phenyl)-7-isopropyl-N-methyl-1H-indole-2-carboxamide 3-(4-(N,N-dimethylsulfamoyl)phenyl)-7-isopropyl-N-phenyl-1H-indole-2-carboxamide, and 3-(4-(N,N-dimethylsulfamoyl)phenyl)-7-isopropyl-N-(oxazol-2-yl)-1H-indole-2-carboxamide.

6. A pharmaceutical composition comprising a compound according to claim 1, or a pharmaceutically acceptable salt or solvate thereof, in admixture with a pharmaceutically acceptable diluent or carrier.

7. The compound of claim 1, wherein $R_7$ is selected from cyano, nitro, hydroxy or a group

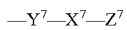

wherein:
Y$^7$ is absent or a linker group of the formula —[CR$^{7A}$R$^{7B}$]$_q$— in which q is an integer selected from 1, 2 or 3, and R$^{7A}$ and R$^{7B}$ are each independently selected from hydrogen or (1-2C)alkyl;

X$^7$ is absent or —O—, —C(O)—, —C(O)O—, —OC(O)—, —N(R$^{7C}$)—, —N(R$^{7D}$)—C(O)—, —N(R$^{7D}$)—C(O)O—, —C(O)—N(R$^{7C}$)—, —S—, —SO—, —SO$_2$—, —S(O)$_2$N(R$^{7C}$)—, or —N(R$^{7D}$)SO$_2$— wherein R$^{7C}$ and R$^{7D}$ are each independently selected from hydrogen or methyl; and Z$^7$ is (2-6C)alkenyl, (2-6C)alkynyl, aryl, (3-6C)cycloalkyl, (3-6C)cycloalkenyl, heteroaryl or heterocyclyl;

and wherein Z$^7$ is optionally further substituted by one or more substituent groups independently selected from oxo, halo, cyano, nitro, hydroxy, carboxy, NR$^{7E}$R$^{7F}$, (1-4C)alkoxy, (1-4C)alkyl, (3-8C)cycloalkyl, (3-8C)cycloalkyl-(1-3C)alkyl, aryl, aryl-(1-2C)alkyl, heterocyclyl, heterocyclyl-(1-2C)alkyl, heteroaryl, heteroaryl-(1-2C)alkyl, C(O)NR$^{7E}$R$^{7F}$, NR$^{7E}$C(O)R$^{7F}$, NR$^{7E}$S(O)$_2$R$^{7F}$ and S(O)$_2$NR$^{7E}$R$^{7F}$; wherein R$^{7E}$ and R$^{7F}$ are each independently selected from hydrogen or (1-4C)alkyl; or R$^{7E}$ and R$^{7F}$ can be linked such that, together with the nitrogen atom to which they are attached, they form a 4-7 membered heterocyclic ring;

and wherein any alkyl, aryl, heterocyclyl or heteroaryl group present in a substituent group on Z$^7$ is optionally further substituted by halo, cyano, nitro, hydroxy, carboxy, NR$^{7G}$R$^{7H}$, (1-2C)alkoxy, or (1-2C)alkyl; wherein R$^{7G}$ and R$^{7H}$ are selected from hydrogen or (1-2C)alkyl;

or R$^{7C}$ and Z$^7$ can be linked such that, together with the nitrogen atom to which they are attached, they form a 4-7 membered heterocyclic ring, which is optionally substituted by oxo, halo, cyano, nitro, hydroxy, carboxy, NR$^{7E}$R$^{7F}$, (1-4C)alkoxy or (1-4C)alkyl.

8. A compound according to claim 1, or a pharmaceutically acceptable salt or solvate thereof, wherein:
$R_3$ is aryl or heteroaryl, wherein said aryl or heteroaryl is substituted by one or more R$^B$;

wherein R$^B$ is halo, cyano, nitro, or a group:

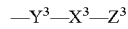

wherein
Y$^3$ is absent or a linker group of the formula —[CR$^{B1}$R$^{B2}$]$_n$— in which n is 1 and R$^{B1}$ and R$^{B2}$ are hydrogen;

X$^3$ is absent or —O—, —C(O)O—, —N(R$^{B3}$)—, —N(R$^{B4}$)—C(O), —C(O)—N(R$^{B3}$)—, —SO$_2$— or —S(O)$_2$N(R$^{B3}$)—, or —N(R$^{B4}$)SO$_2$—; wherein R$^{B3}$ and R$^{B4}$ are each independently selected from hydrogen or methyl; and Z$^3$ is (1-6C)alkyl;

and wherein Z$^3$ is optionally further substituted by one or more substituent groups independently selected from oxo, halo or (1-4C)alkyl; and $R_7$ is a group

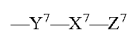

wherein:
Y$^7$ is a linker group of the formula —[CR$^{7A}$R$^{7B}$]$_q$— in which q is an integer selected from 1, 2 or 3, and R$^{7A}$ and R$^{7B}$ are each independently selected from hydrogen or (1-2C)alkyl;

X$^7$ is absent or —O—, —C(O)—, —C(O)O—, —OC(O)—, —N(R$^{7C}$)—, —N(R$^{7D}$)—C(O)—, —N(R$^{7D}$)—C(O)O—, —C(O)—N(R$^{7C}$)—, —S—, —SO—, —SO$_2$—, —S(O)$_2$N(R$^{7C}$)—, or —N(R$^{7D}$)SO$_2$— wherein R$^{7C}$ and R$^{7D}$ are each independently selected from hydrogen or methyl; and $Z^7$ is (2-6C)alkyl, aryl, (3-6C)cycloalkyl, (3-6C)cycloalkenyl, heteroaryl or heterocyclyl;

and wherein $Z^7$ is optionally further substituted by one or more substituent groups independently selected from oxo, halo, cyano, nitro, hydroxy, carboxy, $NR^{7E}R^{7F}$, (1-4C)alkoxy, (1-4C)alkyl, (3-8C)cycloalkyl, (3-8C)cycloalkyl-(1-3C)alkyl, aryl, aryl-(1-2C)alkyl, heterocyclyl, heterocyclyl-(1-2C)alkyl, heteroaryl, heteroaryl-(1-2C)alkyl, $C(O)NR^{7E}R^{7F}$, $NR^{7E}C(O)R^{7F}$, $NR^{7E}S(O)_2R^{7F}$ and $S(O)_2NR^{7E}R^{7F}$; wherein $R^{7E}$ and $R^{7F}$ are each independently selected from hydrogen or (1-4C)alkyl; or $R^{7E}$ and $R^{7F}$ can be linked such that, together with the nitrogen atom to which they are attached, they form a 4-7 membered heterocyclic ring;

and wherein any alkyl, aryl, heterocyclyl or heteroaryl group present in a substituent group on $Z^7$ is optionally further substituted by halo, cyano, nitro, hydroxy, carboxy, $NR^{7G}R^{7H}$, (1-2C)alkoxy, or (1-2C)alkyl; wherein $R^{7G}$ and $R^{7H}$ are selected from hydrogen or (1-2C)alkyl.

9. A compound according to claim 1, or a pharmaceutically acceptable salt or solvate thereof, wherein:

$R_3$ is aryl or heteroaryl, wherein said aryl or heteroaryl is substituted by one or more $R^B$;

wherein $R^B$ is halo, cyano, nitro, or a group:

—$Y^3$—$X^3$—$Z^3$ wherein $Y^3$ is absent or a linker group of the formula —$[CR^{B1}R^{B2}]_n$— in which n is 1 and $R^{B1}$ and $R^{B2}$ are hydrogen;

$X^3$ is absent or —O—, —C(O)O—, —$N(R^{B3})$—, —$N(R^{B4})$—C(O), —C(O)—$N(R^{B3})$—, —$SO_2$— or —$S(O)_2N(R^{B3})$—, or —$N(R^{B4})SO_2$—; wherein $R^{B3}$ and $R^{B4}$ are each independently selected from hydrogen or methyl; and $Z^3$ is (1-6C)alkyl;

and wherein $Z^3$ is optionally further substituted by one or more substituent groups independently selected from oxo, halo or (1-4C)alkyl; and $R_7$ is a group

—$Y^7$—$X^7$—$Z^7$ wherein:

$Y^7$ is a linker group of the formula —$[CR^{7A}R^{7B}]_q$— in which q is an integer selected from 1 or 2, and $R^{7A}$ and $R^{7B}$ are each independently selected from hydrogen or (1-2C)alkyl;

$X^7$ is absent or —O—; and $Z^7$ is aryl, (3-6C)cycloalkyl, (3-6C)cycloalkenyl, heteroaryl or heterocyclyl;

and wherein $Z^7$ is optionally further substituted by one or more substituent groups independently selected from oxo, halo, cyano, nitro, hydroxy, carboxy, $NR^{7E}R^{7F}$, (1-4C)alkoxy, (1-4C)alkyl, $C(O)NR^{7E}R^{7F}$ or $NR^{7E}C(O)R^{7F}$; wherein $R^{7E}$ and $R^{7F}$ are each independently selected from hydrogen or (1-4C)alkyl;

and wherein any alkyl group present in a substituent group on $Z^7$ is optionally further substituted by halo, cyano, nitro, hydroxy, carboxy, $NR^{7G}R^{7H}$, (1-2C)alkoxy, or (1-2C)alkyl; wherein $R^{7G}$ and $R^{7H}$ are selected from hydrogen or (1-2C)alkyl.

* * * * *